US006537987B1

(12) United States Patent
Hamanaka et al.

(10) Patent No.: US 6,537,987 B1
(45) Date of Patent: Mar. 25, 2003

(54) 4,1-BENZOXAZEPINES OR 4,1-BENZOTHIAZEPINES AND THEIR USE AS SQUALENE SYNTHETASE INHIBITORS

(75) Inventors: Ernest S. Hamanaka, Gales Ferry, CT (US); Cheryl M. Hayward, Waterford, CT (US)

(73) Assignee: Pfizer Inc., New York, NY (US)

( * ) Notice: Subject to any disclaimer, the term of this patent is extended or adjusted under 35 U.S.C. 154(b) by 382 days.

(21) Appl. No.: 09/202,106

(22) PCT Filed: May 14, 1997

(86) PCT No.: PCT/IB97/00550

§ 371 (c)(1),
(2), (4) Date: Dec. 18, 1998

(87) PCT Pub. No.: WO97/48701

PCT Pub. Date: Dec. 24, 1997

Related U.S. Application Data

(60) Provisional application No. 60/022,365, filed on Jun. 20, 1996.

(51) Int. Cl.⁷ .......................... A61K 31/55; A61P 25/28; A61P 9/10; C07D 413/06; C07D 417/06
(52) U.S. Cl. .......................... 514/211.04; 514/211.05; 514/211.09; 514/211.11; 540/488; 540/490; 540/547; 540/548; 540/552
(58) Field of Search .................. 540/488, 490, 540/547, 548, 552; 514/211.04, 211.05, 211.09, 211.11

(56) References Cited

U.S. PATENT DOCUMENTS 5,770,594 A * 6/1998 Hamanaka et al. .......... 514/211
5,965,553 A * 10/1999 Bell et al. ................... 514/211
6,110,909 A * 8/2000 Yukimasa et al. ..... 514/211.05

FOREIGN PATENT DOCUMENTS

| EP | 0 567 026 | * 10/1993 |
| WO | WO 96/09827 | * 4/1996 |
| WO | WO 96/20184 | * 7/1996 |
| WO | WO 97/10224 | * 3/1997 |

OTHER PUBLICATIONS

Bristol, James A., Annual Reports in Medicinal Chemistry, vol. 33, p. 394, 1998.*

* cited by examiner

*Primary Examiner*—Brenda Coleman
(74) *Attorney, Agent, or Firm*—Peter C. Richardson; Gregg C. Benson; A. Dean Olson

(57) ABSTRACT

This invention relates to certain benzoxazepinones and benzothiazepinones useful as hypocholesterolemic agents, hypotriglyceridemic agents, antiatherosclerosis agents, antifungal agents, anti-Alzheimer's agents or anti-acne agents.

57 Claims, No Drawings

4,1-BENZOXAZEPINES OR 4,1-BENZOTHIAZEPINES AND THEIR USE AS SQUALENE SYNTHETASE INHIBITORS

This application was filed under 35 U.S.C. §371 based on PCT/IB97/00550 which was filed May 14, 1997 which claims priority from U.S. provisional No. 60/022,365 which was filed on Jun. 20, 1996 and is now abandoned.

BACKGROUND OF THE INVENTION

This invention relates to squalene synthetase inhibitors, pharmaceutical compositions containing such inhibitors and the use of such inhibitors to treat hypercholesterolemia, hypertriglyceridemia, atherosclerosis, fungal infections, acne and Alzheimer's disease in mammals, including humans.

Plasma cholesterol levels have been positively correlated with the incidence of clinical events associated with coronary heart disease (CHD). Thus, pharmacological interventions that reduce cholesterol levels in mammals have a beneficial effect on CHD. In particular, decreased plasma low density lipoprotein (LDL) cholesterol levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and secretion of cholesterol and bile acids by the liver.

Cholesterol synthesis occurs in multiple tissues, but principally in the liver and the intestine. It is a multistep process starting from acetyl-coenzyme A catalyzed by a series of enzymes including hydroxymethylglutaryl-coenzyme A (HMG-CoA) reductase, HMG-CoA synthase, squalene synthetase, squalene epoxidase, squalene cyclase and lanosterol demethylase. Inhibition of catalysis by these enzymes or blocking HMG-CoA reductase gene expression is recognized as an effective means to reduce cholesterol biosynthesis (thus inhibitors thereof are referred to as cholesterol synthesis inhibitors) and can lead to a reduction in cholesterol levels. For example, there are known HMG-CoA reductase inhibitors (e.g., lovastatin, simvastatin, pravastatin, fluvastatin, atorvastatin, rivastatin) that are used for the treatment of hypercholesterolemia.

Recently adopted National Cholesterol Education Program guidelines recommend aggressive lipid-lowering therapy for patients with pre-existing cardiovascular disease or for those with multiple factors that place them at increased risk.

The term squalene synthetase inhibitor refers to compounds that inhibit the condensation of 2 molecules of farnesylpyrophosphate to form squalene, a reaction that is catalyzed by the enzyme squalene synthetase. Such inhibition is readily determined by those skilled in the art according to standard assays (Meth. Enzymol. 1969; 15: 393–454 and Meth. Enzymol. 1985; 110:359–373 and references contained therein). A summary of squalene synthetase inhibitors has been compiled (Curr. Op. Ther. Patents (1993) 8614). European patent publication 0 567 026 A1 discloses certain 4,1-benzoxazepine derivatives as squalene synthase inhibitors and their use in the treatment of hypercholesterolemia and as fungicides. European patent publication 0 645 378 A1 discloses certain condensed seven- or eight-membered heterocycles as squalene synthetase inhibitors and their use in treatment and prevention of hypercholesterolemia and fungal infections. European patent publication 0 645 377 A1 discloses certain benzoxazepine derivatives as squalene synthetase inhibitors useful for the treatment of hypercholesterolemia or coronary sclerosis. European patent publication 0 611 749 A1 discloses certain substituted amic acid derivatives useful for treatment of arteriosclerosis. European patent publication 0705607 A2 discloses certain condensed seven- or eight-membered heterocyclic compounds useful as antihypertriglyceridemic agents. PCT Publication WO 96/09827 discloses certain combinations of cholesterol absorption inhibitors and cholesterol synthesis inhibitors including benzoxazepin derivatives and benzothiazepinone derivatives. European patent publication 0710725 A1 discloses a process for producing certain optically active compounds, including benzoxazepine compounds, having plasma cholesterol and triglyceride lowering activities.

Thus, although there are a variety of hypercholesterolemia therapies, there is a continuing need and a continuing search in this field of art for alternative therapies.

SUMMARY OF THE INVENTION

This invention is directed to cholesterol synthesis inhibitor compounds of FORMULA I useful for the treatment of hypercholesterolemia, hypertriglyceridemia, atherosclerosis, fungal infections, Alzheimer's disease and acne.

The compounds of this invention have the Formula I

FORMULA I

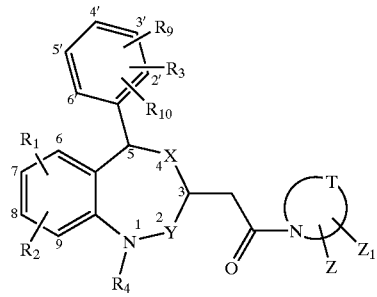

or the pharmaceutically acceptable cationic and anionic salts, prodrugs or stereoisomers thereof wherein X is oxy, thio, —S(O)— or —S(O)$_2$—;

Y is carbonyl or methylene;

$R_1$ and $R_2$ are each independently hydrogen, halo, hydroxyl, trifluoromethyl, (C$_1$–C$_4$)alkyl, fluorinated (C$_1$–C$_4$)alkyl having from 1 to 9 fluorines, (C$_1$–C$_4$) alkoxy, fluorinated (C$_1$–C$_4$)alkoxy having from 1 to 9 fluorines, (C$_1$–C$_4$)alkylthio, (C$_1$–C$_4$)alkylsulfinyl, (C$_1$–C$_4$)alkylsulfonyl, phenyl, amino, mono-N- or di-N,N-(C$_1$–C$_4$)alkylamino, carboxyl, (C$_1$–C$_4$) alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from 1 to 9 fluorines, (C$_1$–C$_4$)alkanoyl, (C$_1$–C$_6$)alkanoyl(C$_1$–C$_6$) alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_3$, $R_9$ and $R_{10}$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$alkyl, oxazolyl, thiazolyl, isoxazolyl, pyrazolyl or isothiazolyl wherein said preceding heterocycles are carbon linked or wherein $R_3$ and $R_9$ can be taken together to form a five, six or seven membered carbocyclic ring or can be taken together to form methylenedioxyl, ethylenedioxyl or propylenedioxyl and such rings formed by taking $R_3$ and $R_9$ together are fused at the 2' and 3' or 3' and 4' positions;

$R_4$ is $(C_1-C?)$alkyl, $(C_1-C_7)$alkenyl or $(C_3-C_4)$cycloalkylmethyl or said $(C_1-C_7)$alkyl, $(C_1-C_7)$alkenyl or $(C_3-C_4)$cycloalkylmethyl is optionally mono-, di-, or tri-substituted wherein the substituents are independently chosen from hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, mono-N- or di-N,N-$(C_1-C_4)$alkylamino, mono-N- or di-N,N-$(C_1-C_4)$alkylaminocarbonyl, mono-N-or di-N,N$(C_1-C_4)$alkylaminosulfonyl; or $R_4$ is $(C_1-C_7)$alkyl substituted with 1 to 15 fluorines or $(C_3-C_4)$cycloalkylmethyl substituted with 1 to 9 fluorines; or $R_4$ is het$(C_1-C_6)$alkyl wherein het is a 4–7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;

Z is carboxyl, $(C_1-C_4)$alkoxycarbonyl, mono-N- or di-N,N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$(C$_1$–C$_4$)alkyl or N(R$_{12}$)COR$_{15}$;

$Z_1$ is H, carboxyl, hydroxyl, $(C_1-C_4)$alkoxy or $(C_1-C_4)$alkoxycarbonyl;

$R_{12}$, $R_{13}$ and $R_{14}$ are each independently H or $(C_1-C_4)$alkyl;

$R_{15}$ is $(C_1-C_4)$alkyl;

$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; or $R_5$ is phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R_5$ is thiazolyl, isothiazolyl, thienyl, furyl, pyridinyl or any of said heterocycles optionally mono-substituted by carboxyl, or mono- or di-substituted with methyl; and T forms a four to seven membered mono-aza, saturated ring, said ring optionally containing thio or oxo and said ring optionally mono-substituted on carbon with hydroxyl, $(C_1-C_4)$alkoxy or carboxyl.

A preferred group of compounds, designated the "A Group", contains those compounds having the Formula I as shown above wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;

$R_3$, $R_9$ and $R_{10}$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_3$ and $R_9$ taken together form an $(C_1-C_3)$alkylenedioxy ring;

X is oxy;

Y is carbonyl;

Z is carboxyl or tetrazol-5-yl; and $Z_1$ is H or carboxyl.

A group of compounds, which is preferred among the "A Group" of compounds designated the "B Group", contains those compounds wherein Zi is H;

T forms a piperidin-1-yl ring; and $R_3$ and $R_9$ are each independently $(C_1-C_4)$alkoxy or taken together form a $(C_1-C_3)$alkylenedioxy ring.

A group of compounds, which is preferred among the "B Group" of compounds designated the "C Group", contains those compounds wherein $R_4$ is neopentyl;

$R_1$ is 7-chloro;

$R_2$ is H;

$R_{10}$ is H;

$R_3$ is 2'-methoxy;

$R_9$ is 3'-methoxy; and

Z is 4-carboxyl.

A group of compounds, which is preferred among the "B Group" of compounds designated the "D Group", contains those compounds wherein $R_4$ is neopentyl;

$R_1$ is 7-methyl;

$R_2$ is H;

$R_{10}$ is H;

$R_3$ is 2'-methoxy;

$R_9$ is 3'-methoxy; and

Z is 4-carboxyl.

A group of compounds, which is preferred among the "B Group" of compounds designated the "E Group", contains those compounds wherein R₄ is neopentyl;
R₁ is 7-methyl;
R₂ is H;
R₁₀ is H;
R₃ is 2'-methoxy;
R₉ is 3'-methoxy; and
Z is 3-carboxyl.

A group of compounds, which is preferred among the "B Group" of compounds designated the "F Group", contains those compounds wherein
R₄ is neopentyl;
R₁ is 7-chloro;
R₂ is H;
R₁₀ is H;
R₃ is 2'-methoxy;
R₉ is 3'-methoxy; and
Z is 3-carboxyl.

A group of compounds, which is preferred among the a "B Group" of compounds designated the "G Group", contains those compounds wherein
R₄ is neopentyl;
R₁ is 7-chloro;
R₂ is H;
R₁₀ is H;
R₃ and R₉ are taken together to form 2', 3'-ethylenedioxyl; and
Z is 3-carboxyl.

A group of compounds, which is preferred among the "B Group" of compounds designated the "H Group", contains those compounds wherein R₄ is neopentyl;
R₁ is 7-chloro;
R₂ is H;
R₁₀ is H;
R₃ and R₉ are taken together to form 2', 3'-ethylenedioxyl; and
Z is 4-carboxyl.

A group of compounds, which is preferred among the "A Group" of compounds designated the "I Group", contains those compounds wherein
T forms a pyrrolidin-1-yl ring;
R₄ is neopentyl;
R₁ is 7-chloro;
R₂ is H;
R₁₀ is H;
R₃ is 2'-methoxy;
R₉ is 3'-methoxy;
Z is 2-carboxyl; and
Z₁ is H.

A group of compounds, which is preferred among the "A Group" of compounds designated the "J Group", contains those compounds wherein
T forms a pyrrolidin-1-yl ring;
R₄ is neopentyl;
R₁ is 7-chloro;
R₂ is H;
R₁₀ is H;
R₃ and R₉ are taken together to form 2', 3'-ethylenedioxyl;
Z is 2-carboxyl; and
Z₁ is H.

A group of compounds, which is preferred among the "A Group" of compounds designated the "K Group", contains those compounds wherein
T forms a piperidin-1-yl ring;
R₄ is neopentyl;
R₁ is 7-chloro;
R₂ is H;
R₁ is H;
R₃ is 2'-methoxy;
R₉ is 3'-methoxy;
Z is 4-carboxyl; and
Z₁ is 2-carboxyl.

A preferred group of compounds, designated the "L Group", contains those compounds having the Formula I as shown above wherein the $C_3$ and $C^5$ substituents are trans;
R₁ and R₂ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or R₁ and R₂ taken together form an ethylenedioxy ring;
R₃, R₉ and R₁₀ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or R₃ and R₉ taken together form an $(C_1-C_3)$ alkylenedioxy ring;
X is oxy;
Y is methylene;
Z is carboxyl or tetrazol-5yl; and
Z₁ is H.

A group of compounds, which is preferred among the "L Group" of compounds designated the "M Group", contains those compounds wherein
T forms a piperidin-1-yl ring; and
R₃ and R₉ are each independently $(C_1-C_4)$alkoxy or taken together form a $(C_1-C_3)$alkylenedioxy ring.

A group of compounds, which is preferred among the "M Group" of compounds designated the "N Group", contains those compounds wherein
R₄ is neopentyl;
R₁ is 7-chloro;
R₂ is H;
R₁₀ is H;
R₃ and R₉ are taken together to form 2', 3'-ethylenedioxyl; and
Z is 3-carboxyl.

A group of compounds, which is preferred among the "M Group" of compounds designated the "O Group", contains those compounds wherein
R₄ is neopentyl;
R₁ is 7-chloro;
R₂ is H;
R₁₀ is H;
R₃ and R₉ are taken together to form 2', 3'-ethylenedioxyl; and
Z is 4-carboxyl.

A group of compounds, which is preferred among the "M Group" of compounds designated the "P Group", contains those compounds wherein R₄ is neopentyl;
R₁ is 7-chloro;
R₂ is H;
R₁₀ is H;
R₃ is 2'-methoxy;
R₉ is 3'-methoxy; and
Z is 4-carboxyl.

A preferred group of compounds, designated the "Q Group", contains those compounds having the Formula I as shown above wherein
the C³ and C⁵ substituents are trans;
R₁ and R₂ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or R₁ and R₂ taken together form an ethylenedioxy ring;
R₃, R₉ and R₁₀ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or R₃ and R₉ taken together form an $(C_1-C_3)$ alkylenedioxy ring;
X is thio;
Y is carbonyl;
Z is carboxyl or tetrazol-5-yl; and
Z₁ is H.

A group of compounds, which is preferred among the a "Q Group" of compounds designated the a "R Group", contains those compounds wherein
T forms a piperidin-1-yl ring; and
R₃ and R₉ are each independently $(C_1-C_4)$alkoxy or taken together form a $(C_1-C_3)$alkylenedioxy ring.

A group of compounds, which is preferred among the "R Group" of compounds designated the "S Group", contains those compounds wherein
R₄ is neopentyl;
R₁ is 7-methyl;
R₂ is H;
R₁₀ is H;
R₃ is 2'-methoxy;
R₉ is 3'-methoxy; and
Z is 3-carboxyl.

A group of compounds, which is preferred among the a "R Group" of compounds designated the "T Group", contains those compounds wherein
R₄ is neopentyl;
R₁ is 7-methylthio;
R₂ is H;
R₁₀ is H;
R₃ is 2'-methoxy;
R₉ is 3'-methoxy; and
Z is 4-carboxyl.

A group of compounds, which is preferred among the "R Group" of compounds designated the "U Group", contains those compounds wherein
R₄ is neopentyl;
R₁ is 7-methylthio;
R₂ is H;
R₁₀ is H;
R₃ is 2'-methoxy;
R₉ is 3'-methoxy; and
Z is 3-carboxyl.

A group of compounds, which is preferred among the "R Group" of compounds designated the "V Group", contains those compounds wherein
R₄ is neopentyl;
R₁ is 7-methyl;
R₂ is H;
R₁₀ is H;
R₃ and R₉ are taken together to form 2', 3'-ethylenedioxyl; and
Z is 3-carboxyl.

A preferred group of compounds, designated the "W Group", contains those compounds having the Formula I as shown above wherein the compounds are
(−)-N-[trans-7-chloro-5-(2,3-ethylenedioxyphenyl)-neopentyl-1,2,3,5-tetrahydro-2-oxo-4,1-benzoxazepine-3-acetyl]isonipecotic acid;
(−)-N-[Trans-7-chloro-5-(2,3-dimethoxyphenyl)-1-neopentyl-2-oxo-1,2,3,5-tetrahydro-4,1-benzoxazepin-3-acetyl]isonipecotic acid;
(−)-N-[Trans-7-chloro-5-(2,3-dimethoxyphenyl)-1-neopentyl-2-oxo-1,2,3,5-tetrahydro-4,1-benzoxazepin-3-acetyl]nipecotic acid;
(−)N-[Trans-7-chloro-5-(2,3-dimethoxyphenyl)-1-neopentyl-2-oxo-1,2,3,5-tetrahydro-4,1-benzoxazepin-3-acetyl]-L-proline;
(−)-N-[Trans-7-methyl-5-(2,3-dimethoxyphenyl)-1-neopentyl-2-oxo-1,2,3,5-tetrahydro-4,1-benzoxazepin-3-acetyl]isonipecotic acid;
(−)-N-[Trans-7-methyl-5-(2,3-dimethoxyphenyl)-1-neopentyl-2-oxo-1,2,3,5-tetrahydro-4,1-benzoxazepin-3-acetyl]nipecotic acid; and
(−)-N-[Trans-7-chloro-5-(2,3-ethylenedioxyphenyl)-1-neopentyl-2-oxo-1,2,3,5-tetrahydro-4,1-benzoxazepin-3-acetyl]nipecotic acid.

The above seven compounds are also especially preferred as individual compounds.

A group of compounds, which is preferred among the "A Group" of compounds designated the "X Group", contains those compounds wherein
Z₁ is H;
T forms a piperidin-1-yl ring; and
R₃ and R₉ are each independently H, $(C_1-C_4)$alkoxy, trifluoromethoxy, or taken together form a $(C_1-C_3)$ alkylenedioxy ring.

A group of compounds, which is preferred among the "X Group" of compounds designated the "Y Group", contains those compounds wherein
R₄ is neopentyl;
R₁ is 7-chloro;
R₂ is H;
R₁₀ is H;
R₃ is 2-methoxy;
R₉ is 4methoxy; and
Z is 4-carboxyl.

A group of compounds, which is preferred among the "X Group" of compounds designated the "Z Group", contains those compounds wherein
R₄ is neopentyl;
R₁ is 7-methyl;
R₂ is H;

$R_{10}$ is H;
$R_3$ and $R_9$ are taken together form a 2,3-ethylenedioxy ring; and
Z is 4-carboxyl.

A group of compounds, which is preferred among the "X Group" of compounds designated the "A1 Group", contains those compounds wherein
$R_4$ is neopentyl;
$R_1$ is 7-methyl;
$R_2$ is H;
$R_{10}$ is H;
$R_3$ and $R_9$ are taken together form a 2,3-ethylenedioxy ring; and
Z is 3-carboxyl.

A group of compounds, which is preferred among the "X Group" of compounds designated the "B1 Group", contains those compounds wherein
$R_4$ is neopentyl;
$R_1$ is 7-chloro;
$R_2$ is H;
$R_{10}$ is H;
$R_3$ is 2-methoxy;
$R_9$ is H; and
Z is 4-carboxyl.

A group of compounds, which is preferred among the "X Group" of compounds designated the "C1 Group", contains those compounds wherein
$R_4$ is neopentyl;
$R_1$ is 7-chloro;
$R_2$ is H;
$R_{10}$ is H;
$R_3$ is 2-trifluoromethoxy;
$R_9$ is H; and
Z is 4-carboxyl.

A group of compounds, which is preferred among the "X Group" of compounds designated the "B1 Group", contains those compounds wherein
$R_4$ is neopentyl;
$R_1$ is 7-chloro;
$R_2$ is H;
$R_{10}$ is H;
$R_3$ is 2-methoxy; and
$R_9$ is H; and
Z is 3-carboxyl.

A group of compounds, which is preferred among the "X Group" of compounds designated the "E1 Group", contains those compounds wherein
$R_4$ is neopentyl;
$R_1$ is 7-chloro;
$R_2$ is H;
$R_{10}$ is H;
$R_3$ and $R_9$ are taken together form a 2,3-methylenedioxy ring; and
Z is 4-carboxyl.

A group of compounds, which is preferred among the "X Group" of compounds designated the "F1 Group", contains those compounds wherein
$R_4$ is neopentyl;
$R_1$ is 7-chloro;
$R_2$ is H;

$R_{10}$ is H;
$R_3$ and $R_9$ are taken together form a 2,3-methylenedioxy ring; and
Z is 3-carboxyl.

A group of compounds, which is preferred among the "X Group" of compounds designated the "G1 Group", contains those compounds wherein
$R_4$ is neopentyl;
$R_1$ is 7-methyl;
$R_2$ is H;
$R_{10}$ is H;
$R_3$ and $R_9$ are taken together form a 2,3-methylenedioxy ring; and
Z is 4-carboxyl.

A group of compounds, which is preferred among the "X Group" of compounds designated the "H1 Group", contains those compounds wherein
$R_4$ is neopentyl;
$R_1$ is 7-methyl;
$R_2$ is H;
$R_{10}$ is H;
$R_3$ and $R_9$ are taken together form a 2,3-methylenedioxy ring; and
Z is 3-carboxyl.

A group of compounds, which is preferred among the "X Group" of compounds designated the "I1 Group", contains those compounds wherein
$R_4$ is neopentyl;
$R_1$ is 7-methoxy;
$R_2$ is H;
$R_{10}$ is H;
$R_3$ is 2-methoxy;
$R_9$ is 3-methoxy; and
Z is 3-carboxyl.

A group of compounds, which is preferred among the "X Group" of compounds designated the "J1 Group", contains those compounds wherein
$R_4$ is neopentyl;
$R_1$ is 7-trifluoromethoxy;
$R_2$ is H;
$R_{10}$ is H;
$R_3$ is 2-methoxy;
$R_9$ is 3-methoxy; and
Z is carboxyl.

A group of compounds, which is preferred among the "X Group" of compounds designated the "K1 Group", contains those compounds wherein
$R_4$ is neopentyl;
$R_1$ is 7-trifluoromethoxy;
$R_2$ is H;
$R_{10}$ is H;
$R_3$ is 2-methoxy;
$R_9$ is 3-methoxy; and
Z is 4-carboxyl.

A group of compounds, which is preferred among the "X Group" of compounds designated the "L1 Group", contains those compounds wherein
$R_4$ is neopentyl;
$R_1$ is 7-trifluoromethoxy;
$R_2$ is H;

$R_{10}$ is H;

$R_3$ and $R_9$ are taken together form a 2,3-ethylenedioxy ring; and

Z is 4-carboxyl.

A group of compounds, which is preferred among the "X Group" of compounds designated the "M1 Group", contains those compounds wherein $R_4$ is neopentyl;

$R_1$ is 7-trifluoromethoxy;

$R_2$ is H;

$R_{10}$ is H;

$R_3$ and $R_9$ are taken together form a 2,3-ethylenedioxy ring; and

Z is 3-carboxyl.

A group of compounds, which is preferred among the "X Group" of compounds designated the "N1 Group", contains those compounds wherein $R_4$ is neopentyl;

$R_1$ is 7-trifluoromethoxy;

$R_2$ is H;

$R_{10}$ is H;

$R_3$ and $R_9$ are taken together form a 2,3-methylenedioxy ring; and

Z is 4-carboxyl.

A group of compounds, which is preferred among the "X Group" of compounds designated the "O1 Group", contains those compounds wherein $R_4$ is neopentyl;

$R_1$ is 7-trifluoromethoxy;

$R_2$ is H;

$R_{10}$ is H;

$R_3$ and $R_9$ are taken together form a 2,3-methylenedioxy ring; and

Z is 3-carboxyl.

A group of compounds, which is preferred among the "X Group" of compounds designated the "P1 Group", are the following compounds. These compounds are also especially preferred as individual compounds.

a. (−)-N-[Trans-7-chloro-5-(2,4-dimethoxyphenyl)-1-neopentyl-2-oxo-1,2,3,5-tetrahydro-4,1-benzoxazepin-3-acetyl]isonipecotic acid;

b. (−)-N-[Trans-7-methyl-5-(2,3-ethylenedioxyphenyl)-1-neopentyl-2-oxo-1,2,3,5-tetrahydro-4,1-benzoxazepin-3-acetyl]isonipecotic acid;

c. (−)-N-[Trans-7-methyl-5-(2,3-ethylenedioxyphenyl)-1-neopentyl-2-oxo-1,2,3,5-tetrahydro-4,1-benzoxazepin-3-acetyl]nipecotic acid;

d. (−)-N-[Trans-7-chloro-5-(2-methoxyphenyl)-1-neopentyl-2-oxo-1,2,3,5-tetrahydro-4,1-benzoxazepin-3-acetyl]isonipecotc acid; and e. (−)-N-[Trans-7-chloro-5-(2-trifluoromethoxyphenyl)-1-neopentyl-2-oxo-1,2,3,5-tetrahydro-4,1-benzoxazepin-3-acetyl]isonipecotic acid.

A group of compounds, which is preferred among the "X Group" of compounds designated the "Q1 Group", are the following compounds. These compounds are also especially preferred as individual compounds.

a. (−)-N-[Trans-7-chloro-5-(2-methoxyphenyl)-1-neopentyl-2-oxo-1,2,3,5-tetrahydro-4,1-benzoxazepin-3-acetyl]nipecotic acid;

b. (−)-N-[Trans-7-chloro-5-(2,3-methylenedioxyphenyl)-1-neopentyl-2-oxo-1,2,3,5-tetrahydro-4,1-benzoxazepin-3-acetyl]isonipecotic acid;

c. (−)-N-[Trans-7-chloro-5-(2,3-methylenedioxyphenyl)-1-neopentyl-2-oxo-1,2,3,5-tetrahydro-4,1-benzoxazepin-3-acetyl]nipecotic acid;

d. (−)-N-[Trans-7-methyl-5-(2,3-methylenedioxyphenyl)-1-neopentyl-2-oxo-1,2,3,5-tetrahydro-4,1-benzoxazepin-3-acetyl]isonipecotic acid; and e. (−)-N-[Trans-7-methyl-5-(2,3-methylenedioxyphenyl)-1-neopentyl-2-oxo-1,2,3,5-tetrahydro-4,1-benzoxazepin-3-acetyl]nipecotic acid.

A group of compounds, which is preferred among the "X Group" of compounds designated the "R1 Group", are the following compounds. These compounds are also especially preferred as individual compounds.

a. (−)-N-[Trans-7-methoxy-5-(2,3-dimethoxyphenyl)-1-neopentyl-2-oxo-1,2,3,5-tetrahydro-4,1-benzoxazepin-3-acetyl]nipecotic acid;

b. (−)-N-[Trans-7-trifluoromethoxy-5-(2,3-dimethoxyphenyl)-1-neopentyl-2-oxo-1,2,3,5-tetrahydro-4,1-benzoxazepin-3-acetyl]nipecotic acid;

c. (−)-N-[Trans-7-trifluoromethoxy-5-(2,3-dimethoxyphenyl)-1-neopentyl-2-oxo-1,2,3,5-tetrahydro-4,1-benzoxazepin-3-acetyl]isonipecotic acid;

d. (-N-[Trans-7-trifluoromethoxy-5-(2,3-ethylenedioxyphenyl)-1-neopentyl-2-oxo-1,2,3,5-tetrahydro-4,1-benzoxazepin-3-acetyl]isonipecotic acid; and e. (−)-N-[Trans-7-trifluoromethoxy-5-(2,3-ethylenedioxyphenyl)-1-neopentyl-2-oxo-1,2,3,5-tetrahydro-4,1-benzoxazepin-3-acetyl]nipecotic acid.

A group of compounds, which is preferred among the "X Group" of compounds designated the "S1 Group", are the following compounds. These compounds are also especially preferred as individual compounds.

a. (−)-N-[Trans-7-trifluoromethoxy-5-(2,3-methylenedioxyphenyl)-1-neopentyl-2-oxo-1,2,3,5-tetrahydro-4,1-benzoxazepin-3-acetyl]isonipecotic acid; and b. (-N-[Trans-7-trifluoromethoxy-5-(2,3-methylenedioxyphenyl)-1-neopentyl-2-oxo-1,2,3,5-tetrahydro-4,1-benzoxazepin-3-acetyl]nipecotic acid.

A preferred group of compounds, designated the "S2 Group", contains the following compounds. These compounds are also especially preferred as individual compounds.

a. (-N-[Trans-7-chloro-5-(2,3-dimethoxyphenyl)-1-neopentyl-2-oxo-1,2,3,5-tetrahydro-4,1-benzoxazepin-3-acetyl]isonipecotic acid;

b. (−)-N-[Trans-7-methyl-5-(2,3-dimethoxyphenyl)-1-neopentyl-2-oxo-1,2,3,5-tetrahydro-4,1-benzoxazepin-3-acetyl]isonipecotic acid;

c. (-N-[Trans-7-methyl-5-(2,3-dimethoxyphenyl)-1-neopentyl-2-oxo-1,2,3,5-tetrahydro-4,1-benzoxazepin-3-acetyl]nipecotic acid;

d. (−)-N-[Trans-7-chloro-5-(2,3-dimethoxyphenyl)-1-neopentyl-2-oxo-1,2,3,5-tetrahydro-4,1-benzoxazepin-3-acetyl]nipecotic acid; and e. (−)-N-[Trans-7-chloro-5-(2,3-ethylenedioxyphenyl)-1-neopentyl-2-oxo-1,2,3,5-tetrahydro-4,1-benzoxazepin-3-acetyl]nipecotic acid.

A preferred group of compounds, designated the "S3 Group", contains the following compounds. These compounds are also especially preferred as individual compounds.

a. (−)-N-[Trans-7-chloro-5-(2,3-ethylenedioxyphenyl-1-neopentyl-2-oxo-1,2,3,5-tetrahydro-4,1-benzoxazepin-3-acetyl]isonipecotic acid;

b. (−)-N-[Trans-7-chloro-5-(2,3-dimethoxyphenyl)-1-neopentyl-2-oxo-1,2,3,5-tetrahydro-4,1-benzoxazepin-3-acetyl]-L-proline;

c. (−)-N-[Trans-7-chloro-5-(2,3-ethylenedioxyphenyl)-2-oxo-1,2,3,5-tetrahydro-4,1-benzoxazepin-3-acetyl]-L-proline;

d. (−)-N-[Trans-7-chloro-5-(2,3-dimethoxyphenyl)-1-neopentyl-2-oxo-1,2,3,5-tetrahydro-4,1-benzoxazepin-3-acetyl]-cis-2,4-piperidinedicarboxylic acid; and e. (-N-[Trans-7-methyl-5-(2,3-dimethoxyphenyl)-1-neopentyl-2-oxo-1,2,3,5-tetrahydro-4,1-benzothiazepin-3-acetyl]nipecotic acid.

A preferred group of compounds, designated the "S4 Group", contains the following compounds. These compounds are also especially preferred as individual compounds.

a. (-N-[Trans-7-methylthio-5-(2,3-dimethoxyphenyl)-1-neopentyl-2-oxo-1,2,3,5-tetrahydro-4,1-benzothiazepin-3-acetyl]isonipecotic acid;

b. (−)-N-[Trans-7-methylthio-5-(2,3-dimethoxyphenyl)-1-neopentyl-2-oxo-1,2,3,5-tetrahydro-4,1-benzothiazepin-3-acetyl]nipecotic acid; and c. (−)-N-[Trans-7-methyl-5-(2,3-ethylenedioxyphenyl)-1-neopentyl-2-oxo-1,2,3,5-tetrahydro-4,1-benzothiazepin-3-acetyl]nipecotic acid.

Alternatively, for Formula I as shown, above $R_4$ can be $(C_1-C_7)$alkyl, $(C_1-C_7)$alkenyl or $(C_3-C_4)$cycloalkylmethyl or said $(C_1-C_7)$alkyl, $(C_1-C_7)$alkenyl or $(C_3-C_4)$ cycloalkylmethyl is optionally mono-, di-, or tri-substituted wherein the substituents are independently chosen from hydroxyl, oxo, $(C_1-C_4)$alkyl, amino, carboxy, thiol, $(C_1-C_4)$ alkoxy, $(C_1-C_4)$alkoxycarbonyl, fluorinated $(C_1-C_4)$alkoxy having from 1 to 9 fluorines, $(C_1-C_4)$alkylthio, $(C_1-C_4)$ alkylsulfinyl, $(C_1-C_4)$alkylsulfonyl, mono-N- or di-N,N-$(C_1-C_4)$alkylamino, mono-N- or di-N,N-$(C_1-C_4)$ alkylaminocarbonyl, mono-N-or di-N,N$(C_1-C_4)$ alkylaminosulfonyl;

Yet another aspect of this invention is directed to methods for treating hypercholesterolemia, hypertriglyceridemia, atherosclerosis, fungal infections, Alzheimer's disease and acne in a mammal (including a human being) by administering to a mammal suffering from hypercholesterolemia, hypertriglyceridemia, atherosclerosis, a fungal infection, Akzheimer's disease or acne a hypercholesterolemia, hypertriglyceridemia, atherosclerosis, anti-fungal, Alzheimer's disease or acne treating amount of a Formula I compound or the pharmaceutically acceptable cationic and anionic salts, prodrugs or stereoisomers thereof.

Yet another aspect of this invention is directed to a method for treating hypercholesterolemia in a mammal (including a human being) by administering to a mammal suffering from hypercholesterolemia a hypercholesterolemia treating amount of a Formula I compound or the pharmaceutically acceptable cationic and anionic salts, prodrugs or stereoisomers thereof.

Yet another aspect of this invention is directed to a method for treating hypertriglyceridemia in a mammal (including a human being) by administering to a mammal suffering from hypertriglyceridemia a hypertriglyceridemia treating amount of a Formula I compound or the pharmaceutically acceptable cationic and anionic salts, prodrugs or stereoisomers thereof.

Yet another aspect of this invention is directed to a method for treating atherosclerosis in a mammal (including a human being) by administering to a mammal suffering from atherosclerosis an atherosclerotic treating amount of a Formula I compound or the pharmaceutically acceptable cationic and anionic salts, prodrugs or stereoisomers thereof.

Yet another aspect of this invention is directed to a method for treating a fungal infection in a mammal (including a human being) by administering to a mammal suffering from a fungal infection an antifungal treating amount of a Formula I compound or the pharmaceutically acceptable cationic and anionic salts, prodrugs or stereoisomers thereof.

Yet another aspect of this invention is directed to a method for treating Alzheimer's disease in a mammal (including a human being) by administering to a mammal suffering from Alzheimer's disease an Alzheimer's disease treating amount of a Formula I compound or the pharmaceutically acceptable cationic and anionic salts, prodrugs or stereoisomers thereof.

Yet another aspect of this invention is directed to a method for treating acne in a mammal (including a human being) by administering to a mammal suffering from acne an acne treating amount of a Formula I compound or the pharmaceutically acceptable cationic and anionic salts, prodrugs or stereoisomers thereof.

This invention is also directed to pharmaceutical compositions which comprise a therapeutically effective amount of a compound of Formula I or the pharmaceutically acceptable cationic and anionic salts, prodrugs or stereoisomers thereof and a pharmaceutically acceptable carrier.

This invention is also directed to pharmaceutical compositions for the treatment of hypercholesterolemia, hypertriglyceridemia, atherosclerosis, fungal infections, Alzheimer's or acne in a mammal (including a human being) which comprise a therapeutically effective amount of a compound of the Formula I or the pharmaceutically acceptable cationic and anionic salts, prodrugs or stereoisomers thereof and a pharmaceutically acceptable carrier.

This invention is also directed to pharmaceutical compositions for the treatment of hypercholesterolemia in a mammal (including a human being) which comprise a hypercholesterolemia treating amount of a compound of the Formula I or the pharmaceutically acceptable cationic and anionic salts, prodrugs or stereoisomers thereof and a pharmaceutically acceptable carrier.

This invention is also directed to pharmaceutical compositions for the treatment of hypertriglyceridemia in a mammal (including a human being) which comprise a hypertriglyceridemia treating amount of a compound of the Formula I or the pharmaceutically acceptable cationic and anionic salts, prodrugs or stereoisomers thereof and a pharmaceutically acceptable carrier.

This invention is also directed to pharmaceutical compositions for the treatment of atherosclerosis in a mammal (including a human being) which comprise an atherosclerosis treating amount of a compound of the Formula I or the pharmaceutically acceptable cationic and anionic salts, prodrugs or stereoisomers thereof and a pharmaceutically acceptable carrier.

This invention is also directed to pharmaceutical compositions for the treatment of a fungal infection in a mammal (including a human being) which comprise an antifungal treating amount of a compound of the Formula I or the pharmaceutically acceptable cationic and anionic salts, prodrugs or stereoisomers thereof and a pharmaceutically acceptable carrier.

This invention is also directed to pharmaceutical compositions for the treatment of Alzheimer's disease in a mammal (including a human being) which comprise an Alzheimer's disease treating amount of a compound of the Formula I or the pharmaceutically acceptable cationic and anionic salts, prodrugs or stereoisomers thereof and a pharmaceutically acceptable carrier.

This invention is also directed to pharmaceutical compositions for the treatment of acne in a mammal (including a human being) which comprise an acne treating amount of a compound of the Formula I or the pharmaceutically acceptable cationic and anionic salts, prodrugs or stereoisomers thereof and a pharmaceutically acceptable carrier.

Another aspect of this invention is a compound of the Formula I or the pharmaceutically acceptable cationic and anionic salts, prodrugs or stereoisomers thereof or a composition which comprises an amount thereof, for use as a medicament, in particular as an antifungal agent, hypocholesterolemic agent, hypotriglyceridemic agent, anti-atherosclerosis agent, anti-Alzheimer's disease agent or anti-acne agent.

Yet another aspect of this invention is the use of a compound of the Formula I or the pharmaceutically acceptable cationic and anionic salts, prodrugs or stereoisomers thereof or a composition which comprises an amount thereof, for the manufacture of an antifungal agent, hypocholesterolemic agent, hypoglyceridemic agent, anti-atherosclerosis agent, anti-Alzheimer's disease agent or anti-acne agent.

This invention is also directed to a pharmaceutical combination composition for the treatment of hypercholesterolemia comprising:

a therapeutically effective amount of a first compound, said first compound being a compound of Formula I or the pharmaceutically acceptable cationic and anionic salts, prodrugs or stereoisomers thereof;

a therapeutically effective amount of a second compound, said second compound being a cholesterol absorption inhibitor, a cholesterol synthesis inhibitor (other than the compounds of Formula I), a fibrate, niacin, an ion-exchange resin, an antioxidant, an ACAT inhibitor or a bile acid sequestrant; and a pharmaceutical carrier.

Preferred among the second compounds are an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred HMG-CoA reductase inhibitor is lovastatin, simvastatin, pravastatin, fluvastatin, atorvastatin or rivastatin.

A particularly preferred lanosterol demethylase inhibitor is fluconazole or voriconazole.

Another aspect of this invention is a method for treating hypercholesterolemia in a mammal comprising administering to a mammal suffering from hypercholesterolemia a therapeutically effective amount of a first compound, said first compound being a compound of Formula I or the pharmaceutically acceptable cationic and anionic salts, prodrugs or stereoisomers thereof; and a therapeutically effective amount of a second compound, said second compound being a cholesterol absorption inhibitor or a cholesterol synthesis inhibitor (other than the compounds of Formula I), a fibrate, niacin, an ion-exchange resin, an antioxidant, an ACAT inhibitor or a bile acid sequestrant.

A preferred aspect of the above method is wherein the second compound is an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred aspect of the above method is wherein the HMG-CoA reductase inhibitor is lovastatin, simvastatin, pravastatin, fluvastatin, atorvastatin or rivastatin.

Yet another aspect of this invention is a kit containing a treatment for hypercholesterolemia comprising:

a. a therapeutically effective amount of a first compound, said first compound being a compound of Formula I or the pharmaceutically acceptable cationic and anionic salts, prodrugs or stereoisomers thereof and a pharmaceutically acceptable carrier in a first unit dosage form;

b. a therapeutically effective amount of a second compound, said second compound being a cholesterol absorption inhibitor, a cholesterol synthesis inhibitor (other than the compounds of Formula I), a fibrate, niacin, an ion-exchange resin, an antioxidant, an ACAT inhibitor or a bile acid sequestrant and a pharmaceutically acceptable carrier in a second unit dosage form; and c. container means for containing said first and second dosage forms.

A preferred second compound is an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred HMG-CoA reductase inhibitor is lovastatin, simvastatin, pravastatin, fluvastatin, atorvastatin or rivastatin.

This invention is also directed to a pharmaceutical combination composition for the treatment of a fungal infection comprising:

a therapeutically effective amount of a compound of Formula I or the pharmaceutically acceptable cationic and anionic salts, prodrugs or stereoisomers thereof;

a therapeutically effective amount of a lanosterol demethylase inhibitor; and a pharmaceutical carrier.

A particularly preferred lanosterol demethylase inhibitor is fluconazole.

Another particularly preferred lanosterol demethylase inhibitor is voriconazole.

Another aspect of this invention is a method for treating a fungal infection in a mammal comprising administering to a mammal suffering from a fungal infection a therapeutically effective amount of a compound of Formula I or the pharmaceutically acceptable cationic and anionic salts, prodrugs or stereoisomers thereof; and a therapeutically effective amount of a lanosterol demethylase inhibitor.

A particularly preferred aspect of the above method is wherein the lanosterol demethylase inhibitor is fluconazole.

Another particularly preferred aspect of the above method is wherein the lanosterol demethylase inhibitor is voriconazole.

Yet another aspect of this invention is a kit containing a treatment for a fungal infection comprising:

a. a therapeutically effective amount of a compound of Formula I or the pharmaceutically acceptable cationic and anionic salts, prodrugs or stereoisomers thereof and a pharmaceutically acceptable carrier in a first unit dosage form;

b. a therapeutically effective amount of a lanosterol demethylase inhibitor and a pharmaceutically acceptable carrier in a second unit dosage form; and c. container means for containing said first and second dosage forms.

A particularly preferred aspect of the above kit is wherein the lanosterol demethylase inhibitor is fluconazole.

Another particularly preferred aspect of the above kit is wherein the lanosterol demethylase inhibitor is voriconazole.

This invention is also directed to a pharmaceutical combination composition for the treatment of acne comprising:

a therapeutically effective amount of a compound of Formula I or the pharmaceutically acceptable cationic and anionic salts, prodrugs or stereoisomers thereof;

a therapeutically effective amount of an antibiotic agent; and a pharmaceutical carrier.

Another aspect of this invention is a method for treating acne in a mammal comprising administering to a mammal suffering from acne a therapeutically effective amount of a compound of Formula I or the pharmaceutically acceptable cationic and anionic salts, prodrugs or stereoisomers thereof; and a therapeutically effective amount of an antibiotic agent.

Yet another aspect of this invention is a kit containing a treatment for acne comprising:

a. a therapeutically effective amount of a compound of Formula I or the pharmaceutically acceptable cationic and anionic salts, prodrugs or stereoisomers thereof and a pharmaceutically acceptable carrier in a first unit dosage form;

b. a therapeutically effective amount of an antibiotic agent and a pharmaceutically acceptable carrier in a second unit dosage form; and c. container means for containing said first and second dosage forms.

The term "treating", "treat" or "treatment" as used herein includes preventative (e.g., prophylactic) and palliative treatment.

Exemplary T rings are piperidin-1-yl, pyrrolidin-1-yl, thiazolidin-3-yl, azetidin-1-yl, tetrahydro-1,4-thiazin-4-yl, tetrahydro-1,4-oxazin-4-yl and tetrahydro-1,3-thiazin-3yl.

Exemplary het rings are pyrazolyl, imidazolyl, triazolyl, tetrazolyl, piperidinyl, piperazinyl or morpholino.

By halo is meant chloro, bromo, iodo, or fluoro.

By alkyl is meant straight chain or branched saturated hydrocarbon.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, L-lysine, L-arginine, meglamine (N-methyl-glucamine), benethamine (N-benzylphenethylamine), piperazine or tromethamine (2-amino-2-hydroxymethyl-1,3-propanediol). This is meant to include (R)-α-methylbenzylammonium.

The expression "prodrug" refers to compounds that are drug precursors, which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the Formula I compounds include but are not limited to substituents wherein the Z or $Z_1$ moiety is independently carboxyl and the free hydrogen is replaced by $(C_1-C_4)$alkyl, $(C_2-C_7)$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

As used herein, the expression "reaction-inert solvent" and "inert solvent" refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included as an aspect of this invention.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

As used herein the term mono-N- or di-N,N-$(C_1-C_x)$alkyl . . . refers to the $(C_1-C_x)$alkyl moiety taken independently when it is di-N,N-$(C_1-C_x)$alkyl . . . (x refers to integers).

As stated herein the ring formed by T may be optionally mono-substituted on carbon, such monosubstitution is in addition to Z and $Z_1$.

Other features and advantages will be apparent from the specification and claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction Schemes.

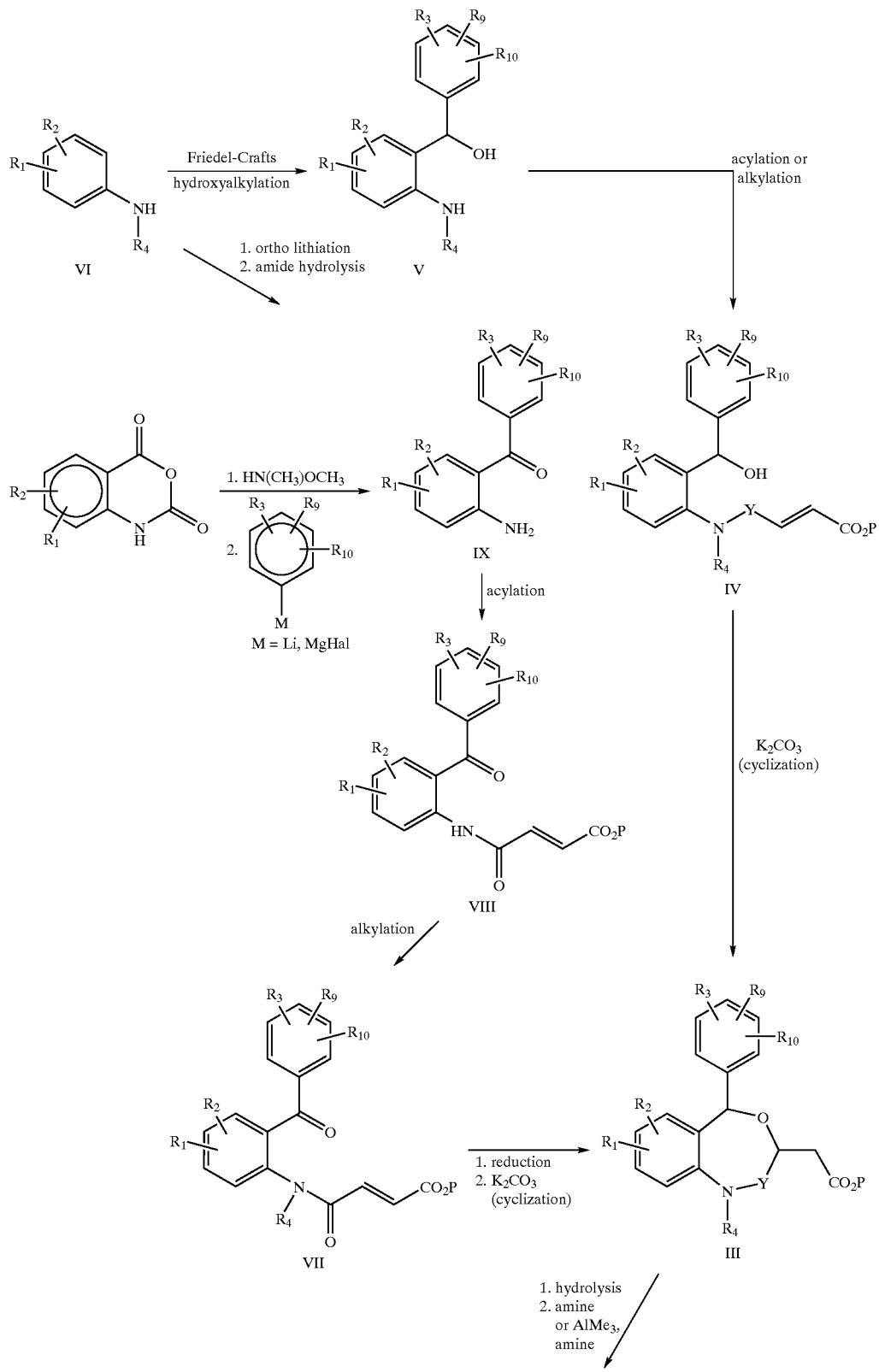

-continued
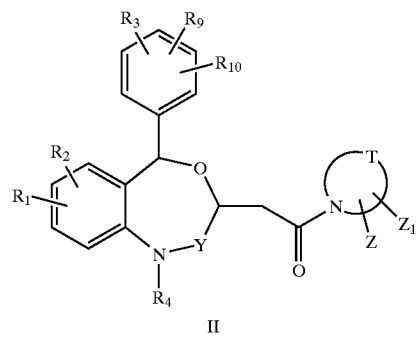
II
Reaction Scheme 2
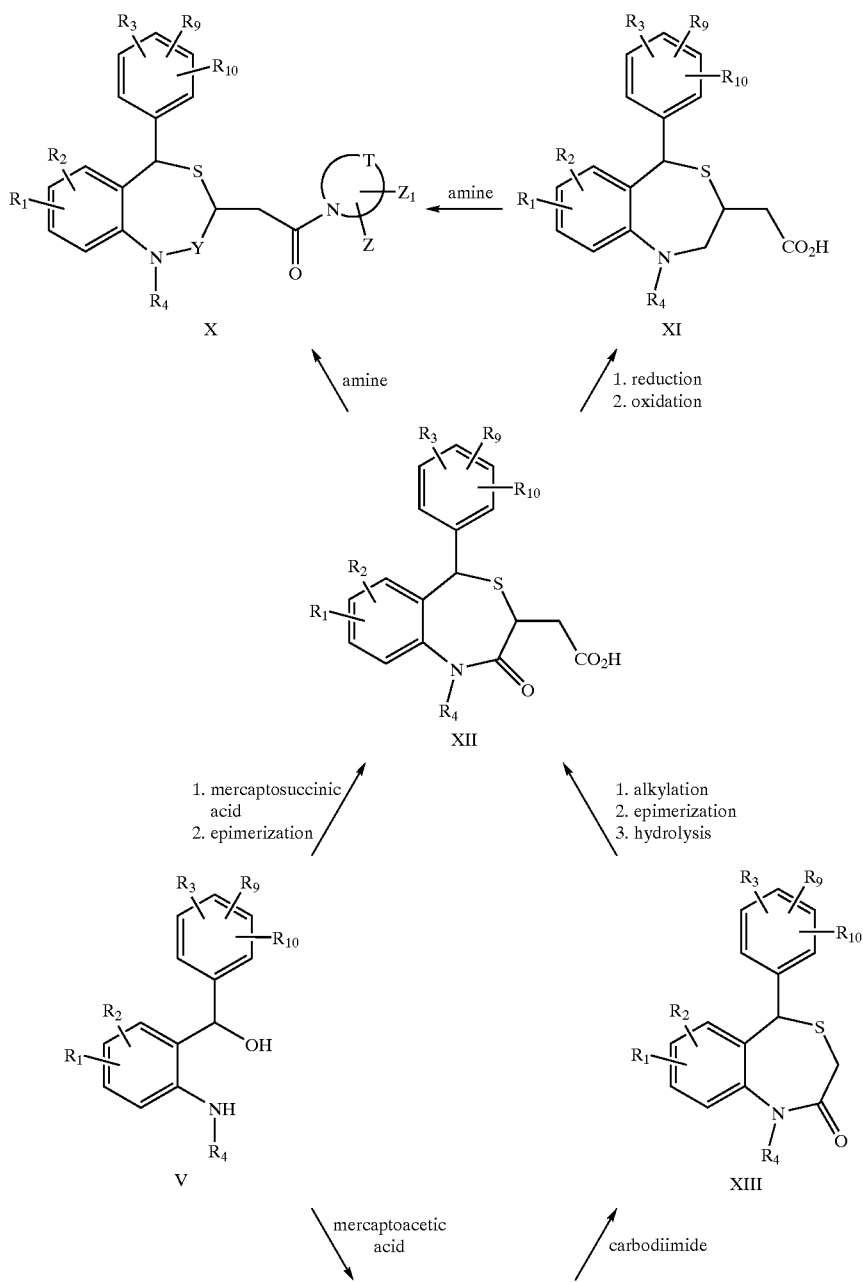

-continued

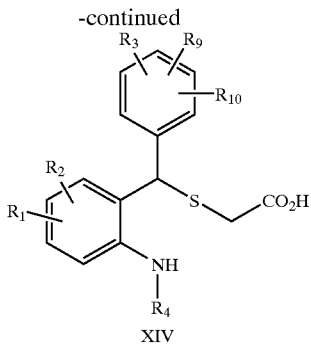

XIV

As a preliminary note, some substituents (e.g., $R_4$) may best be prepared through conversion of another functional group at a point later in the synthetic sequence to the introduction of the substituent (e.g., $R_4$ in Formulas VI and VII). When to use these conversion methods will vary depending on the nature of the substituent and the compound's stability to the reaction conditions and can be readily determined by one skilled in the art. The method of preparation can also be readily determined by one skilled in the art using conventional methods of organic synthesis.

Also, some of the preparation methods described herein will require protection of remote functionality (i.e., carboxyl, hydroxyl). The need for these protecting groups will vary depending on the nature of the remote functionality and the conditions of the preparation methods. This need is readily determined by one skilled in the art. For a general description of protecting groups (e.g., halo($C_1$–$C_4$)alkyl, ($C_1$–$C_4$)alkoxymethyl, arylmethyl and tri($C_1$–$C_4$)alkylsilyl) and their use, see T. W. Greene, *Protective Groups in Organic Synthesis*, John Wiley & Sons, New York, 1991.

According to Reaction Scheme 1 the desired Formula I compounds wherein $R_1$, $R_2$, $R_3$, $R_4$, $R_9$, $R_{10}$, T, Z and $Z_1$ are as described above (with Z and $Z_1$ being appropriately protected when Z or $Z_1$ are independently hydroxyl or carboxyl), X is oxy, and Y is carbonyl or methylene (depicted as Formula II compounds) may be prepared by acylating the appropriate amine with the corresponding Formula III compound (which has previously been hydrolyzed to the corresponding acid (where P is hydrogen)).

Generally, a Formula III compound is hydrolyzed in an aqueous alcoholic solvent such as methanol/water with a base such as potassium carbonate at a temperature of about 40° C. to about 80° C., preferably at reflux, for about 2 hours to about 18 hours. The resulting carboxylic acid is then combined with the appropriate amine in an aprotic solvent such as dimethylformamide in the presence of an amine base such as triethylamine and a coupling agent such as diethyl cyanophosphonate or propylphosphonic anhydride at a temperature of about 0° C. to about 40° C. for about 1 hour to about 6 hours.

Alternatively, the acid is combined with the appropriate amine in the presence of a carbodiimide (e.g., 1-(3-dimethylaminopropyl)-3-ethylcarbodiimide hydrochloride) in a reaction inert solvent such as methylene chloride at a temperature of about 10° C. to 40° C. for about 2 to about 24 hours.

The desired Formula I compound wherein Z or $Z_1$ are carboxyl may be prepared from the corresponding Formula II compound wherein Z or $Z_1$ are alkoxycarbonyl (i.e., protected as described above) by hydrolysis. Alternatively, the hydrolysis step may be omitted resulting in the desired prodrugs.

Generally, a Formula II compound is hydrolyzed in an aqueous alcoholic solvent such as methanol/water with a base such as potassium carbonate at a temperature of about 40° C. to about 80° C., preferably at reflux, for about 2 hours to about 18 hours.

Prodrugs of Formula I compounds having a carboxyl group may be prepared by combining the acid with the appropriate alkyl halide in the presence of a base such as potassium carbonate in an inert solvent such as dimethylformamide at a temperature of about 15° C. to about 100° C. for about 1 hour to about 24 hours.

Alternatively, the acid is combined with the appropriate alcohol as solvent in the presence of a catalytic amount of acid such as concentrated sulfuric acid at a temperature of about 20° C. to about 120° C., preferably at reflux, for about 1 hour to about 24 hours.

The desired Formula I compound wherein Z is tetrazol-5-yl may be prepared from the corresponding Formula I compound wherein Z is carboxyl by converting the carboxyl group to a carboxamide group (Z is $CONH_2$), dehydrating the carboxamide to the nitrile (Z is CN) and reacting the nitrile with an appropriate azide to form the tetrazole group.

Generally, the acid is converted to the imidazolide by reaction with carbonyl diimidazole in an aprotic solvent such as methylene chloride at a temperature of 15° C. to about 40° C. for about 30 minutes to about 4 hours, conveniently at room temperature for 1 hour. The resulting imidazolide is converted to the corresponding amide by bubbling ammonia gas into the reaction mixture at a temperature of 10° C. to about 40° C. for about 3 minutes to about 30 minutes, preferably at room temperature for about 5 minutes or until the reaction is complete by TLC analysis. The amide is converted to the nitrile by treatment with trifluoroacetic anhydride and triethylamine in an inert solvent such as methylene chloride at 0° C. for about 25 minutes to 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole.

The desired Formula I compound wherein Z is 4,5-dihydro-5-oxo-1,2,4-oxadiazol-3-yl may be prepared from the corresponding Formula I compound wherein Z is CN by converting the nitrile to the amide oxime and reacting the amide oxime with a carbonylating agent to form the corresponding 4,5-dihydro-5-oxo-1,2,4-oxadiazole derivative.

Generally, the nitrile is converted to the amide oxime by reaction with hydroxylamine hydrochloride in the presence of a base such as potassium carbonate in an alcoholic solvent at a temperature of about 60° C. to about 11° C. for about 5 hours to 24 hours, preferably in refluxing ethanol for about 18 hours. The amide oxime is converted to the corresponding 4,5-dihydro-5-oxo-1,2,4-oxadiazole derivative by reaction with carbonyidiimidazole and triethylamine in refluxing ethyl acetate for 24 hours.

The desired Formula I compound wherein Z is aminocarbonyl or (di)alkylaminocarbonyl may be prepared from the corresponding Formula I compounds where Z is alkoxycarbonyl by reaction with a complex of an amine salt and trimethylaluminum in an inert solvent such as toluene at a temperature of about 25° C. to 110° C. for about 2 to 24 hours. When the amine is ammonia, the reaction may yield either the nitrile or the carboxamide. The nitrile may be hydrolyzed to the primary carboxamide (Z is $CONH_2$) by treatment with aqueous hydrogen peroxide in the presence of a base such as potassium carbonate in a cosolvent such as ethanol or dimethylsulfoxide at a temperature of 10° C. to 100° C. for about 2 to 24 hours. Alternatively, a Formula I compound wherein Z is aminocarbonyl or (di) alkylaminocarbonyl may be prepared by converting the acid to its imidazolide followed by conversion to the amide as described above for the preparation of a Formula I compound wherein Z is tetrazol-5-yl.

The desired Formula III compounds wherein $R_1$, $R_2$, $R_3$, $R_4$, $R_9$ and $R_{10}$ are as described above, X is oxy, Y is carbonyl or methylene and P is a known carboxyl protecting group (see reference above) may be prepared from the corresponding Formula IV compound by cyclization.

Generally, the Formula IV compound is combined with a base such as potassium carbonate in an alcoholic solvent such as ethanol at a temperature of about 10° C. to about 40° C., preferably ambient, for about 2 hours to about 18 hours.

The desired Formula IV compounds wherein $R_1$, $R_2$, $R_3$, $R_4$, $R_9$ and $R_{10}$ are as described above, X is oxy, Y is carbonyl or methylene and P is a known carboxyl protecting group (see reference above) may be prepared from the appropriate corresponding Formula V compound by acylation or alkylation as appropriate.

Generally, for those compounds wherein Y is carbonyl the appropriate Formula V compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about six to about eighteen hours. Generally, for those compounds wherein Y is methylene the appropriate Formula V compound is combined with the appropriately protected 4-halocrotonic acid, such as alkyl 4-halocrotonate, in the presence of a base such as potassium carbonate in a polar aprotic solvent such as dimethylformamide at a temperature of about 10° C. to about 50° C., typically ambient, for about 12 hours to about 72 hours.

The $R_4$ substituent may be added to either the Formula VI or Formula V compounds by the following three alternative methods.

The desired Formula V compound wherein $R_1$, $R_2$, $R_3$, $R_4$, $R_9$ and $R_{10}$ are as described above may be prepared from the appropriate corresponding Formula VI compound by hydroxyalkylation (a modified Friedel-Crafts reaction).

Generally, the Formula VI compound is combined with a Lewis acid such as boron trichloride in a reaction-inert solvent such as benzene or toluene at a temperature of about ambient to about reflux for about 1 to about 6 hours under a nitrogen atmosphere to form an intermediate complex. The resulting complex is combined with the appropriately substituted benzaldehyde in a reaction-inert solvent such as benzene in the presence of an amine base such as triethylamine at a temperature of about 0° C. to about 40° C., typically ambient, for about 30 minutes to about 18 hours followed by aqueous acid cleavage of the boron moiety.

Alternatively, a Formula V compound wherein $R_1$, $R_2$, $R_3$, $R_4$, $R_9$ and $R_{10}$ are as described above may be prepared by treating a Formula VI compound wherein $R_4$ is alkanoyl (optionally substituted as described above) with excess strong base, preferably 2.5 equivalents of n-butyllithium, in an anhydrous ethereal solvent, preferably tetrahydrofuran. The reaction is performed at a temperature of 0° C. to about 50° C. for about 1 hour to about 3 hours and the resulting dianion is reacted with the appropriate benzaldehyde. The resulting substituted benzhydrol derivative is then reacted with a reducing agent such as a borane-dimethyl sulfide complex in an ethereal solvent such as tetrahydrofuran at an elevated temperature, typically reflux resulting in the corresponding amine optionally substituted as described above for $R_4$.

In yet another alternative method, the Formula V compounds wherein $R_1$, $R_2$, $R_3$, $R_4$, $R_9$ and $R_{10}$ are as described above may be prepared by treating the Formula VI compound, wherein $R_4$ is alkoxycarbonyl, with excess strong base, preferably 2.4 equivalents of t-butyllithium, at a temperature of about −80° C. to about 0° C. The reaction is performed in an anhydrous ethereal solvent such as tetrahydrofuran for about 2 hours to about 4 hours and the resulting dianion is reacted with the appropriate benzaldehyde. The resulting benzhydrol derivative wherein $R_4$ is alkoxycarbonyl is treated with aqueous acid and thereby converted to the Formula V compound, wherein $R_4$ is hydrogen. This compound is transformed to the Formula V compound, wherein $R_4$ is alkyl (optionally substituted as above), by reductive amination under conditions similar to those described for the preparation of the Formula VI compounds.

The desired Formula VI compounds wherein $R_1$ and $R_2$ are as described above and $R_4$ is alkoxycarbonyl or alkanoyl may be prepared from acylation of the corresponding aniline with the appropriate alkyl chloroformate or acyl chloride, respectively, in a manner similar to that used in preparation of Formula IV compounds wherein Y is carbonyl.

The desired Formula VI compound wherein $R_1$, $R_2$, and $R_4$ are as described above may be prepared from the appropriate corresponding aniline by reductive amination.

Generally, the aniline is reacted with the appropriate alkylaldehyde in a protic acidic solvent such as concentrated acetic acid at a temperature of about 10° C. to about 50° C., preferably ambient, for about 30 minutes to about four hours followed by reduction using for example sodium borohydride at a temperature of about 0° C. to about 20° C. for about 15 minutes to about four hours.

Alternatively, the aniline is reacted with the appropriate alkylaldehyde in an aprotic solvent such as 1,2-dichloroethane in the presence of an acid such as acetic acid at a temperature of about 15° C. to about 40° C., preferably ambient temperature, for a period of about 1 to about 20 hours. The resulting compound is reduced using for example sodium triacetoxyborohydride at about −20° C. to about ambient temperature for a period of about 1 to about 20 hours.

Alternatively, the desired Formula III compounds wherein $R_1$, $R_2$, $R_3$, $R_4$, $R_9$ and $R_{10}$ are as described above X is oxy, Y is carbonyl and P is a known carboxyl protecting group (see reference below) may also be prepared from the corresponding Formula VII compounds by reduction followed by cyclization.

Generally, the Formula VII compound is combined with a reducing agent such as sodium borohydride in methanol solvent at a temperature of 0° C. to 30° C. for about 15 minutes to about one hour. The resulting compound is cyclized with a base such as potassium carbonate in an alcoholic solvent such as ethanol at a temperature of about 10° C. to about 40° C., preferably ambient, for about 2 hours to about 18 hours.

The desired Formula VII compounds wherein $R_1$, $R_2$, $R_3$, $R_9$ and $R_{10}$ are as described above, X is oxy, Y is carbonyl and P is a known carboxyl protecting group (see reference below) may be prepared from the appropriate corresponding Formula VIII compound by alkylation.

Generally, the Formula VIII compound is deprotonated with a base such as sodium hydride in a polar aprotic solvent such as dimethylformamide under a nitrogen atmosphere at a temperature of about 0° C. to about 50° C. for about 30 minutes to about 2 hours. Then the appropriate alkyl halide is added at a temperature of about 0° C. to about 60° C., typically ambient temperature, and reacted for about 30 minutes to about 24 hours.

The desired Formula VIII compounds wherein $R_1$, $R_2$, $R_3$, $R_9$ and $R_{10}$ are as described above, X is oxy, Y is carbonyl and P is a known carboxyl protecting group (see reference above) may be prepared from the appropriate corresponding Formula IX compound by acylation.

Generally, the appropriate Formula IX compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about six to about eighteen hours.

The desired Formula IX compounds wherein $R_1$, $R_2$, $R_3$, $R_9$ and $R_{10}$ are as described above may be prepared from the appropriate corresponding Formula VI compound wherein $R_4$ is alkoxycarbonyl by directed ortho lithiation followed by hydrolysis of the amide.

Generally, the appropriate Formula VI compound where $R_4$ is alkoxycarbonyl is treated with excess strong base, preferably greater than 2 equivalents of sec-butyllithium or tert-butyllithium, in an anhydrous ethereal solvent, preferably tetrahydrofuran, under a nitrogen atmosphere at a temperature of −40° C. to 10° C., preferably 0° C., for about 1 hour to about 5 hours. The resulting dianion is then reacted with the Weinreb amide of the appropriate benzoic acid at a temperature of −100° C. to 0° C., preferably −78° C., for about 30 minutes to about 24 hours while gradually warming to ambient temperature. The resulting benzophenone is treated with aqueous acid such as hydrochloric acid in a co-solvent such as tetrahydrofuran or dimethoxyethane at a temperature of 25° C. to 100° C., preferably at reflux, for about 5 hours to about 48 hours.

Alternatively the desired Formula IX compounds may be prepared from the corresponding isatoic anhydride by conversion to the Weinreb amide which is condensed with the appropriate metallated benzene derivative.

Generally the isatoic anhydride is reacted with O,N-dimethylhydroxylamine hydrochloride in the presence of a base such as triethylamine in water and a cosolvent such as dioxan or ethanol at a temperature of 50° C. to 100° C., preferably at reflux for about 1 to 5 hours. The Weinreb amide is deprotonated by a strong base such as butyllithium under a nitrogen atmosphere in an inert solvent such as tetrahydrofuran at a temperature of −78° C. to −40° C. for about 0.5 to 2 hours, then treated with a solution of the appropriate metallated, typically lithiated, phenyl derivative in an inert solvent such as diethyl ether at a temperature of −100° C. to 0° C., preferably −78° C., for about 0.5 hours to about 24 hours while gradually warming to 25° C.

According to Reaction Scheme 2 the desired Formula I compounds wherein $R_1$, $R_2$, $R_3$, $R_4$, $R_9$ and $R_{10}$ are as described above, X is thio, Y is carbonyl or methylene and Z is carboxyl (depicted as Formula X compounds) may be prepared by acylating the appropriate amine with the corresponding Formula XI or XII compound. Generally this reaction may be performed as describe above for the Formula II compounds.

The desired Formula XI compounds wherein $R_1$, $R_2$, $R_3$, $R_4$, $R_9$ and $R_{10}$ are as described above, X is thio, Y is methylene may be prepared from the appropriate corresponding Formula XII compound where Y is carbonyl by a sequential reduction/oxidation procedure.

Generally the Formula XII compound is fully reduced using for example a borane-methyl sulfide complex in a reaction-inert solvent such as tetrahydrofuran at a temperature of about 20° C. to about 8° C., preferably at ambient temperature, for about 1 hours to about 24 hours. The resulting alcohol is then oxidized to the Formula XI compound using for example a two step procedure involving first a Swern oxidation followed by oxidation with buffered sodium chlorite in acetonitrile and aqueous hydrogen peroxide at a temperature of about −10° C. to about 25° C. for about 30 minutes to about 4 hours. Or alternatively, the alcohol is directly oxidized to the acid using t-butyl hydroperoxide and cetyl trimethyl ammonium sulfate in an aqueous mixture at pH greater than 13.

The desired Formula XII compound wherein $R_1$, $R_2$, $R_3$, $R_4$, $R_9$ and $R_{10}$ are as described above, may be prepared from the appropriate corresponding Formula XIII compound by alkylation followed by epimerization and finally hydrolysis.

Generally, the Formula XIII compound is combined with a base such as lithium diisopropylamide in a reaction-inert solvent such as cyclohexane/tetrahydrofuran at a temperature of about −100° C. to about −20° C. under nitrogen for about 30 minutes to about 3 hours followed by addition of a suitable alkyl haloacetate such as t-butyl bromoacetate and mixing for about 2 to about 24 hours at a temperature of about 10° C. to about 40° C., preferably ambient. The alkylated product is epimerized to exclusively the trans isomers using a base such as potassium carbonate in an alcoholic solvent such as methanol for 1 hour to 6 hours at a temperature of about 40° C. to about 80° C., preferably at 60° C. The ester may be hydrolyzed by treatment with an acid such as trifluoroacetic acid in a reaction-inert solvent such as dichloromethane in the case of a t-butyl ester.

The desired Formula XIII compound wherein $R_1$, $R_2$, $R_3$, $R_4$, $R_9$ and $R_{10}$ are as described above, may be prepared from the appropriate corresponding Formula XIV compound by coupling under carbodiimide conditions.

Generally, the Formula XIV compound is combined with a suitable carbodiimide such as 1-(3dimethylaminopropyl)-3-ethylcarbodiimide hydrochloride in a reaction-inert solvent such as dichloromethane at a temperature of about 10° C. to about 50° C., conveniently at ambient temperature, for about 5 hours to about 24 hours.

The desired Formula XIV compound wherein $R_1$, $R_2$, $R_3$, $R_4$, $R_9$ and $R_{10}$ are as described above, may be prepared from the appropriate corresponding Formula V compound by a solvolytic displacement reaction.

Generally, the Formula V compound may be combined with mercaptoacetic acid under aqueous acidic conditions at a temperature of about 60° C. to about 120° C., conveniently at reflux, for about 2 to about 6 hours.

Alternatively, the desired Formula XII compounds wherein $R_1$, $R_2$, $R_3$, $R_4$, $R_9$ and $R_{10}$ are as described above may be prepared from the appropriate corresponding Formula V compound by a solvolytic displacement reaction with mercaptosuccinic acid, cyclization to the lactam and epimerization.

Generally, the Formula V compound and mercaptosuccinic acid are combined in a carboxylic acid solvent such as propionic acid with a means to remove water, such as a nitrogen sweep across the head space of the reaction vessel, and heated to about 100° C. to about 140° C. for about 12 to 72 hours. The cyclized product is epimerized to the trans isomers by treatment in an inert solvent such as tetrahydrofuran with a base such as a metal alkoxide base in the corresponding alcohol solvent, preferably sodium methoxide in methanol, at about ambient temperature to reflux temperature for a period of about 1 to about 24 hours.

It is reiterated that some substituents (e.g., $R_4$) may best be prepared through conversion of another functional group at a point later in the synthetic sequence to the introduction of the substituents (e.g., $R_4$ in Formulas VI and VII). When to use these conversion methods will vary depending on the nature of the substituent and the compound's stability to the reaction conditions and can be readily determined by one skilled in the art. The method of preparation can also be readily determined by one skilled in the art using conventional methods of organic synthesis.

The starting materials and reagents for the above described reaction schemes (e.g., 4-haloaniline, substituted benzaldehyde, fumaric acid monoethyl ester, amino acid esters, prodrug residues, protected forms) are readily available or can be easily synthesized by those skilled in the art using conventional methods of organic synthesis. The preparation of certain compounds disclosed in PCT Publication WO 96/09827 may be used as an aid in preparing certain starting materials. In addition, some of the intermediates used herein to prepare the compounds of this invention are, or are related to, or are derived from amino acids found in nature, in which there is a large scientific interest and commercial need, and accordingly many such intermediates are commercially available or are reported in the literature or are easily prepared from other commonly available substances by well known methods which are reported in the literature.

The methods described above are useful to prepare the compounds of this invention, other methods may be described in the experimental section.

The compounds of Formula I have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture (e.g., ester or salt) by reaction with an appropriate optically active compound (e.g., alcohol or amine), separating the diastereomers and converting (e.g., hydrolyzing or acidifying) the individual diastereomers to the corresponding pure enantiomers. All such isomers, including diastereomers and enantiomers are considered as part of this invention.

Some of the compounds of this invention, where for example Z contains an acid group, are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some of the compounds of this invention where, for example Y is methylene or Z contains an amine group are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The utility of the compounds of the present invention as medical agents in the treatment of diseases (such as are detailed herein) in mammals (e.g., humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

The compounds of this invention are adapted to therapeutic use as agents that lower plasma LDL cholesterol levels in mammals, particularly humans. Since the concentration of cholesterol in blood is closely related to the development of cardiovascular, cerebral vascular or peripheral vascular disorders, these compounds, by virtue of their hypocholesterolemic action, prevent, arrest and/or regress atherosclerosis.

The hypocholesterolemia activity of these compounds can be determined by assessing the effect of these compounds on the action of squalene synthetase by measuring the overall conversion of [$1$-$^3$H]farnesyl pyrophosphate ([$^3$H]FPP) to [$^3$H]squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic add A).

Briefly, to a 3 $\mu$l volume of either DMSO (control) or DMSO containing compound, are added 47 $\mu$l of Squalene Synthetase Cofactor/Substrate solution (SQS Cofactor/Substrate solution contains 50 mM $K_xPO_4$ (pH 7.4), 5.0 mM $MgCl_2$, 411 $\mu$M $NADP^+$, 3.4 mM glucose-6-phosphate, 20 U/ml glucose-6-phosphate dehydrogenase, 15 mM NaF, 78.1 mM sodium ascorbate, 31.3 U/ml ascorbate oxidase, and 1.56 times the indicated final concentrations of [$^3$H]FPP (sp. act. 380/pmol)) and 25 $\mu$l of PMED buffer (PMEB buffer contains 50 mM $K_xPO_4$ (pH 7.4), 5 mM $MgCl_2$, 1.0 mM EDTA, 5.0 mM dithiothreitol) containing 1 mg/ml microsomal protein [Final assay concentrations: 48 mM $K_xPO_4$ (pH 7.4), 4.8 mM $MgCl_2$, 0.33 mM EDTA, 1.67 mM DTT, 258 $\mu$M $NADP^+$, 2.1 mM glucose-6-phosphate, 0.95U glucose-6-phosphate dehydrogenase, 9.5 mM NaF, 50 mM sodium ascorbate, 1.5U ascorbate oxidase, 4% DMSO, and 5.1 μM [$^3$H]farnesyl pyrophosphate]. After incubation at 37° C. for 30 min, enzymatic reactions are terminated by sequential addition of 40 μl, 10 M NaOH, 40 μl EtOH, 10 μl of 2 mg/ml squalene in chloroform. After saponification (90 minutes, 37° C.), aliquots were applied to silica gel TLC and newly formed squalene separated from unreacted substrate by chromatography in toluene-ethyl acetate (9:1). The squalene band is visualized with iodine vapors, removed, and immersed in Aqualsol-2 liquid scintillation fluid. Squalene synthetase activity is expressed as pmoles of squalene formed from farnesyl pyrophosphate per min of incubation at 37° C. per mg microsomal protein, based on the stoichiometry of the reaction whereby two moles of [$^3$H]farnesyl pyrophosphate react to form one mole of [$^3$H] squalene and half of the radiolabel is lost from the C-1 position of the prenylating [$^3$H]farnesyl pyrophosphate due to 1-pro-S hydrogen release. Rat hepatic microsomes are used as the source of squalene synthetase activity as described by Harwood et al (J. Lipid Res. 34, 377, 1993). Briefly, hepatic tissues are rinsed in phosphate buffered saline and immediately homogenized at 4° C. in PMED buffer, using a Dounce tissue homogenizer. Homogenates are centrifuged at 10,000×g for 20 min at 4° C. and the resultant supernatants are centrifuged at 178,000×g for 90 min at 4° C. Microsomal pellets are resuspended in PMED buffer by a Potter-Elvehjem pestle and stored frozen in liquid $N_2$ until use. For such preparations, there is no notable loss in enzyme activity within 3 months.

The hypercholesterolemic treating activity of these compounds may be demonstrated by methods based on standard procedures. For example, the in vivo activity of these compounds in inhibiting cholesterol biosynthesis may be determined by the procedure of Hughes et. al. 1977 J. Biol Chem. 252: 548.

Activity of these compounds can be determined by the amount of hypocholesterolemic agent that reduces hepatic cholesterol biosynthesis, relative to control, in male CD1 mice. Male CD1 mice are maintained on a cholesterol-free diet in a 12 hr light/12 hr dark cycle. At mid light cycle animals are administered a 0.5 mL oral bolus of saline containing 0.25% methyl cellulose, 0.6% Tween 80 and 10% ethanol (control animals) or an oral bolus that contained in addition the desired concentration of compound to be tested. One hour following bolus administration the animals receive an intraperitoneal injection (0.15 ml) of [$^{14}$C]-mevalonolactone dissolved in water (0.5 uCi/animal). One hour following the injection of radioactivity animals are sacrificed, livers excised, saponified ((2.5 M KOH, 2 h) 60° C.) and extracted with petroleum ether and ethanol. After saponification, the radioactivity is measured. Total hepatic radioactivity is calculated based on measured liver weights. The degree of cholesterol biosynthesis inhibition is expressed as a percentage of the total radioactivity in treated vs control animals. The above assay carried out with a range of doses of test compounds allow the determination of an $ED_{50}$ value for the in vivo reduction of hepatic cholesterol biosynthesis.

The hypercholesterolemic and hypertriglyceremia treating activity of these compounds may also be demonstrated by determining the amount of agent required to reduce cholesterol levels and/or triglycerides. For example LDL cholesterol levels may be measured in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). Adult marmosets are assigned to treatment groups so that each group has a similar mean±SD for total plasma cholesterol concentration. After group assignment, marmosets are dosed daily with compound as a dietary admix or by intragastric intubation for from one to eight weeks. Control marmosets receive only the dosing vehicle. Plasma total, LDL and HDL cholesterol values can be determined at any point during the study by obtaining blood from an antecubital vein and by separating plasma lipoproteins into their individual subclasses by density gradient centrifugation, and by measuring cholesterol concentration as previously described (Crook, et al., Arteriosclerosis 10, 625, 1990). An analogous measurement of triglycerides may be made to determine the effect on hypertriglyceremia using for example, an enzymatic assay kit (Wako Pure Chemical Industries).

Anti-atherosclerosis effects of the compounds can be determined by the amount of agent required to reduce the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean±s.d. for total plasma cholesterol concentration. After group assignment, rabbits are dosed daily with compound given as a dietary admix or on a small piece of gelatin based confection. Control rabbits receive only the dosing vehicle be it the food or the gelatin confection. The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the iliac arteries. The aortae are cleaned of adventitia, opened longitudinally and then stained with Sudan IV as described by Holman et al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention for the treatment of hypercholesterolemia, hypertriglyceridemia or atherosclerosis can be via any method which delivers the compound to the intestine and the liver. These methods include oral routes, parenteral, intraduodenal routes etc.

Thus, for example, in one mode of administration a compound of this invention may be administered once at night prior to sleep. Alternatively the compounds may be administered twice or three times daily with or without meals. In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the compound to achieve the plasma cholesterol lowering that he/she considers appropriate for the patient. In considering the degree of hypocholesterolemic activity desired, the physician must balance a variety of factors such as starting cholesterol level, other cardiovascular risk factors, presence of preexisting disease, and age of the patient and his/her motivation. Those skilled in the art will know of the National Cholesterol Education program guidelines for treatment of hypercholesterolemia (Circulation 1991; 83:2154)

In general an effective dosage for the compounds described above for the treatment of hypercholesterolemia, hypertriglyceridemia or atherosclerosis is in the range of 0.0005 to 50 mg/kg/day, preferably 0.001 to 25 mg/kg/day, most preferably 0.005 to 5 mg/kg/day. For an average 70 kg human, this would amount to 0.000035 to 3.5 g/day, preferably 0.00007 to 1.75 g/day, most preferably 0.00035 to 0.35 g/day.

The compounds of this invention are also effective as antifungal agents, useful in the curative or prophylactic treatment of fungal infections in animals such as mammals, including humans. For example, they are useful in treating superficial fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, species of Candida (e.g. *Candida albicans*), *Cryptococcus neoformans, Aspergillus flavus, Aspergillus fumigatus*, Coccidioides, Paracoccidioides, Histoplasma or Blastomyces.

The in vitro evaluation of the antifungal activity of the compounds of this invention can be performed by determining the minimum inhibitory concentration (MIC), which is the concentration of the test compounds, in a suitable medium, at which growth of the particular micro-organism fails to occur. In practice, a series of agar plates, or liquid medium in microtiter plates, each having the test compound incorporated at a particular concentration, is inoculated with a standard culture of, for example, *Cryptococcus neoformans*, and each plate is then incubated for 48 hours at 37° C. The plates are then examined for the presence or absence of growth of the fungus and the appropriate MIC value is noted. Other micro-organisms used in such tests can include *Candida Albicans, Aspergillus fumigatus*, Trichophyton spp., Microsporum spp., *Epidermophyton floccosum, Coccidioides immitis* and *Torulopsis glabrata*.

The in vivo evaluation of the compounds as antifungal agents can be carried out at a series of dose levels by intraperitoneal or intravenous injection, or by oral administration, to mice or rats which are inoculated with, e.g. a strain of *Candida albicans, Aspergillus fumigatus* or *Cryptococcus neoformans*. Activity may be based on the number of survivors from a treated group of mice after the death of an untreated group of mice.

For Candida spp. infection models the dose level at which the compounds provides 50% protection against the lethal effect of the infection ($PD_{50}$) is also assessed.

For Aspergillus spp. infection models the number of mice cured of the infection after a set dose allows further assessment of activity.

For Cryptococcus spp. infection models the number of colony forming units existing after a set dose is assessed and compared with control to determine compound efficacy. A preliminary assessment of potential liver toxicity may also be made on the basis of increase in liver weight relative to control.

As an antifungal treatment the compounds of this invention are administered to mammals (e.g., humans) by conventional methods.

For human antifungal use, the compounds of this invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral antifungal administration to human patients, the daily dosage level of the compounds of this invention for antifungal treatments will be from 0.01 to 20 mg/kg, preferably 0.5 to 5 mg/kg, (in single or divided doses) when administered by either the oral or parenteral route. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of this invention can be administered in the form of a suppository pessary, or they may be applied topically in the form of a lotion, solution, cream, ointment or dusting powder. For example, they can be incorporated into a cream consisting an aqueous emulsion of polyethylene glycols or liquid paraffin; or they can be incorporated, at a concentration between 1 to 10%, into an ointment comprising a white wax or white soft paraffin base together with such stabilizers and preservatives as may be required.

Since the compounds of this invention are cholesterol biosynthesis inhibitors they can also lower the levels of Apolipoprotein E isoform 4 circulating in the bloodstream. Apolipoprotein E isoform 4 that is made in the brain also circulates through the central nervous system and is present in the cerebrospinal fluid. Compounds of this invention are useful for the treatment of Alzheimer's disease.

Apolipoprotein E isoform 4 ("ApoE isoform 4") is an apolipoprotein which is the gene product of the apolipoprotein E Type 4 allele and is carried in the bloodstream on lipoproteins including LDL. Possession of one or two copies of the apolipoprotein E type 4 allele has been linked to a greatly increased risk of developing Alzheimer's disease. In the liver, low density lipoprotein receptors (LDL receptors) are responsible for absorbing and taking up from the bloodstream various lipoproteins including some of those containing ApoE isoform 4. LDL receptors are regulated by gene repressors derived from cholesterol that suppress the transcription of the LDL-receptor. Inhibition of cholesterol biosynthesis reduces the presence of these cholesterol-derived LDL gene repressors. This relieves the suppression of the production of the LDL receptor, leading to production of additional LDL receptors in the liver, which in turn, remove additional amounts of lipoproteins including ApoE Type 4 containing lipoproteins from the bloodstream. The Alzheimer's disease treating activity of these compounds can be determined by assessing the effect of these compounds on the action of squalene synthetase by measuring the overall conversion of [1-$^3$H]farnesyl pyrophosphate to

[³H]squalene, essentially as previously described in Meth. Enzymol. 110, 359, 1985 using the anaerobic atmosphere generating oxygen consumption system described in Analyt. Biochem. 203, 310,1992, in comparison to known controls (e.g., zaragozic acid A). This assay is described more fully above.

The Alzheimer's disease treating activity of these compounds may also be demonstrated by determining the amount of agent required to reduce cholesterol levels, for example LDL cholesterol levels, in the plasma of certain mammals, for example marmosets that possess a plasma lipoprotein profile similar to that of humans (Crook et al. Arteriosclerosis 10, 625,1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). This assay is described more fully above.

The compounds of this invention may be administered using conventional methods for the treatment of Alzheimer's disease. In general an effective dosage for the squalene synthetase inhibitors of this invention for the treatment of Alzheimer's disease is in the range for adults of from about 1 mg to 1000 mg (preferably 5 to 100 mg,) per day which may be given in a single dose or in two to four divided doses. Higher doses may be favorably employed as required.

Since the compounds of this invention are squalene synthesis inhibitors they are effective for the treatment of acne vulgaris. Squalene is a major component of sebum, comprising about 12% of sebum in adults. The severity of acne vulgaris correlates directly with the sebum secretion rate and several compounds which decrease sebum secretion rate have been shown to improve acne. By inhibiting squalene the compounds of this invention can decrease the sebum secretion rate and thereby treat acne.

The concentration of squalene in sebum increases fourfold after puberty and it is believed that this increase in squalene concentration alone or in concert with other changes in sebum composition or sebum secretion rate facilitate the development of acne. The compounds of this invention are useful in preventing or mollifying acne by reducing the percentage and total amount of squalene in sebum.

In addition to reducing squalene levels in sebum, by limiting the production of epoxides, the sebum may become less inflammatory (through metabolic action of the everpresent P. acnes). The compounds of this invention may therefore provide a dual effect to combat acne and thus constitute a new, better treatment for acne than current keratolytic and anti-androgen therapies.

The anti-acne activity of the compounds of this invention may be demonstrated by testing the in vitro effects of the compounds in human sebaceous gland culture using conditions analogous to those described in FEBS Letters 200(1), 173–176 (1986) and J. Cell Science 95, 125136 (1990). Thus, the human sebaceous gland culture may be incubated with the test compound and subsequent sebum production and qualitative changes of sebum composition measured over a short period of time and compared with controls and other actives.

For the treatment of acne the compounds of this invention may be administered by conventional methods. For the treatment of acne each dosage unit will preferably contain 0.001 mg to 1000 mg, advantageously 0.01 mg to 400 mg, of active ingredient. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient.

The compounds of this invention may also be used in conjunction with other pharmaceutical agents. For example, they may be used in combination with other cholesterol synthesis inhibitors and cholesterol absorption inhibitors as described below and other cholesterol lowering agents such as fibrates, niacins, ion-exchange resins, antioxidants, ACAT inhibitors and bile acid sequestrants as a means of lowering plasma cholesterol and as a means of treating atherosclerosis. Alternatively, the compound of this invention may be used in conjunction with an antifungal agent such as those conventional in the art (e.g., lanosterol demethylase inhibitor) for the treatment of a fungal infection. Alternatively, they may be used in conjunction with another anti-acne agent (e.g. a topical or oral antibiotic both of which are conventional in the pharmaceutical industry). In combination therapy treatment, both the compounds of this invention and the other drug therapies are administered to mammals (e.g., humans) by conventional methods.

In particular, other cholesterol absorption inhibitors and cholesterol synthesis inhibitors are described further below.

Other cholesterol absorption inhibitors are described for example, in PCT WO 94/00480.

Any HMG-CoA reductase inhibitor may be used as the second compound in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP491226A (the disclosure of which is incorporated by reference) discloses certain pyridyldihydroxyheptenoic acids, such as rivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin.

Any HMG-CoA synthase inhibitor may be used as the second compound in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155–160: Meth. Enzymol. 1985; 110:19–26 and references cited therein). A variety of these compounds are described and referenced below however other HMG-CoA synthase inhibitors will be known to those skilled in the art. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block the transcription of DNA or translation inhibitors that prevent translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (Meth. Enzymol. 1985; 110:9–19). Several compounds are described and referenced below however other inhibitors of HMG-CoA reductase gene expression will be known to those skilled in the art. U.S. Pat. No. 5,041,432 (the disclosure of which is incorporated by reference) discloses certain 15-substituted lanosterol derivatives. Other oxygenated sterols that suppress synthesis of HMG-CoA reductase are discussed by E. I. Mercer (Prog.Lip. Res. 1993;32:357–416).

Any squalene epoxidase inhibitor may be used as the second compound in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466471). A variety of these compounds are described and referenced below however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989;244:347–350.). In addition, the compounds described and referenced below are squalene cyclase inhibitors, however other squalene cyclase inhibitors will also be known to those skilled in the art. PCT publication 9410150 (the disclosure of which is hereby incorporated by reference) discloses certain 1,2,3,5,6,7,8,8α-octahydro-5,5,8α(beta)-trimethyl-6-isoquinolineamine derivatives, such as N-trifluoroacetyl-1,2,3,5,6,7,8,8α-octahydro-2-allyl-5,5,8α(beta)-trimethyl-6(beta)-isoquinolineamine. French patent publication 2697250 (the disclosure of which is hereby incorporated by reference) discloses certain beta, beta-dimethyl-4-piperidine ethanol derivatives such as 1-(1,5,9-trimethyidecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays (certain experimental conditions) it is not possible to distinguish between squalene epoxidase inhibitors and squalene cyclase inhibitors, however, these assays (experimental conditions) are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below however other squalene epoxidase/squalene cyclase inhibitors will be known to those skilled in the art. U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl) pentyl isopentyl sulfoxide and 2-(1-piperidyl)ethyl ethyl sulfide. PCT publication WO 9401404 (the disclosure of which is hereby incorporated by reference) discloses certain acyl-piperidines such as 1-(1-oxopentyl-5-phenylthio) 4(2-hydroxy-1-methyl)ethyl)piperidine. U.S. Pat. No. 5,102,915 (the disclosure of which is hereby incorporated by reference) discloses certain cyclopropyloxy-squalene derivatives.

Any lanosterol demethylase inhibitor may be used as the second compound in the combination aspect of this invention. The term lanosterol demethylase inhibitor refers to compounds which inhibit the 14-demethylation of lanosterol catalyzed by the enzyme lanosterol demethylase. Such inhibition is readily determined by those skilled in the art according to standard assays (Biochemistry 1994; 33:47024713 and references cited therein). A variety of these compounds are described and referenced below however other lanosterol demethylase inhibitors will be known to those skilled in the art such as fluconazole and voriconazole. Voriconazole is exemplified in U.S. Pat. No. 5,278,175 (the disclosure of which is hereby incorporated by reference) and is (2R,3S)-2-(2,4-difluorophenyl)-3(5-fluoropyrimidin-4-yl)-1-(1,2,4-triazol-1-yl)butan-2-ol. U.S. Pat. Nos. 4,782,059 and 4,894,375 (the disclosures of which are hereby incorporated by reference) disclose certain azoles such as cis-1-acetyl 4-(4-((2-(2,4-dichlorophenyl)-2-(1H-imidazol-1-ylmethyl)1,3-dioxolan-4-yl)methoxy)phenyl) piperazine (ketoconazole). EP publication 492474A (the disclosure of which is hereby incorporated by reference) discloses certain dioxolanes such as (2S,4S)-Cis-2-(2-(4-chlorophenyl) ethyl)-2-imidazol-1-yl)methyl-4-(4-aminophenyl-thio) methyl-1,3-dioxolane. U.S. Pat. No. 5,041,432 (the disclosure of which is hereby incorporated by reference) discloses certain 15-substituted lanosterol derivatives.

The compounds of this invention can be administered individually or together in any conventional oral or parenteral dosage form such as a capsule, tablet, powder, sachet, suspension or solution. For oral administration, which is preferred, a pharmaceutical composition can take the form of solutions, suspensions, tablets, pills, capsules, powders, and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound(s) according to the invention as an active ingredient. In addition, it may include other medicinal or pharmaceutical agents, carriers, adjuvants, etc.

Pharmaceutical compositions according to this invention may contain 0.1%–95% of the compound(s) of this invention, preferably 1%–70%. In any event, the composition or formulation to be administered will contain a quantity of a compound(s) according to the invention in an amount effective to treat the condition of the subject being treated, i.e., hypercholesterolemia, atherosclerosis, Alzheimer's disease or fungal infection.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administerable compositions can be prepared by dissolving or dispersing, or otherwise preparing a compound(s) according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent in light of this disclosure, to those skilled in this art. For examples, see Remington's Pharmaceutical Sciences., Mack Publishing Company, Easter, Pa., 15th Edition (1975).

Since the present invention has an aspect that relates to the treatment of hypercholesterolemia, a fungal infection or acne with a combination of active ingredients which may be administered separately, the invention also relates to combining separate pharmaceutical compositions in kit form. The kit comprises two separate pharmaceutical compositions: a compound of Formula I and a second compound as described above. The kit comprises container means for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also a daily dose of Formula I compound can consist of one tablet or capsule while a daily dose of the second compound can consist of several tablets or capsules and vice versa. The memory aid should reflect this.

In another specific embodiment of the invention a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro chip memory coupled with a liquid crystal readout, or audible reminder signal which, for example, reads out the date that the last daily dose has been taken and/or reminds one when the next dose is to be taken.

In the Examples below proton nuclear magnetic resonance spectra ($^1$H NMR) and nuclear magnetic resonance spectra ($C^{13}$ NMR) were measured for solutions in deuterated solvent. Unless otherwise stated, the NMR spectra were recorded on a 300 MHz instrument. The peak shapes are denoted as follows: s, singlet; d, doublet; t, triplet, q, quartet; m, multiplet; br, broad; c, complex.

EXAMPLE 1

Ethyl Ester of N-[trans-7-Chloro-5-(2,3-ethylenedioxyphenyl)-1-neopentyl-1,2,3,5-tetrahydro-2-oxo-4,1-benzoxazepine-3-acetyl] isonipecotic Acid

EXAMPLE 1A (4-Chloro-phenyl)-(neopentyl)-amine

Pivalaldehyde (20.4 g, 236 mmol, 25.6 mL) was added to a solution of 4-chloroaniline (30.2 g, 236 mmol) in concentrated acetic acid (475 mL) at ambient temperature. After 1.5 hours, the reaction mixture was cooled to 0° C. and sodium borohydride (11.7 g, 307 mmol) was added portionwise over 15 minutes. After stirring for 1 hour, the resulting mixture was diluted with water and extracted with ethyl acetate (3×). The combined organics were washed successively with water (3×), aqueous 2N sodium hydroxide (2×), saturated aqueous sodium bicarbonate, and saturated aqueous sodium chloride, dried over anhydrous sodium sulfate, filtered, and concentrated under reduced pressure to give 47.2 g (99%) of the title compound as an off-white solid which was taken on crude to the next step.

$^1$H NMR (250 MHz, CDCl$_3$) δ 7.10 (d, 2H), 6.53 (d, 2H), 3.65 (br s, 1H), 2.85 (s, 2H), 0.98 (s, 9H).

EXAMPLE 1B (5-Chloro-2-neopentylamino-phenyl)-(2,3-ethylenedioxyphenyl)-methanol A solution of (4-chloro-phenyl)-(neopentyl)-amine (2.24 g, 11.3 mmol) in benzene (6 mL) was added to a solution of boron trichloride (1.0 M in xylenes; 12.5 mL, 12.5 mmol) in benzene (13 mL) at 0° C. under a nitrogen atmosphere. Once the addition was complete, the resulting mixture was heated at reflux for 3 hours, under a steady stream of nitrogen exiting into an aqueous 5N sodium hydroxide trap, and then recooled to 0° C. A solution of 2,3-ethylenedioxybenzaldehyde (1.86 g, 11.3 mmol), triethylamine (2.29 g, 22.7 mmol, 3.2 mL) and benzene (6 mL) was then added and the resulting mixture stirred 3.5 hours before quenching with aqueous 1N hydrochloric acid. After 1 hour, ethyl acetate was added and the resulting mixture was shaken vigorously. The aqueous layer was alkalized with aqueous 5N sodium hydroxide and the layers separated. The aqueous layer was extracted with ethyl acetate (2×). The organic layers were combined, dried over anhydrous sodium sulfate, filtered, concentrated under reduced pressure, and purified by flash column chromatography (4:1 hexanes/ethyl acetate) to produce 3.62 g (88%) of the title compound as an off-white foam.

$^1$H NMR (400 MHz, CDCl$_3$) δ 7.11 (dd, 1H), 6.93 (d, 1H), 6.85 (m, 2H), 6.73 (m, 1H), 6.58 (d, 1H), 5.94 (d, 1H), 4.83 (br s, 1H), 4.30 (m, 4H), 3.03 (d, 1H), 2.84 (d, 2H), 0.94 (s, 9H).

EXAMPLE 1C

3-[{4-Chloro-2-[(2,3-ethylenedioxyphen-1-yl)-hydroxy-methyl]phenyl}neopentyl-carbamoyl]-acrylic Acid Ethyl Ester Fumaric chloride monoethyl ester (1.04 g, 6.43 mmol) was added to a mixture of (5-chloro-2-neopentylamino-phenyl)-(2,3-ethylenedioxyphenyl)-methanol (1.94 g, 5.35 mmol) and sodium bicarbonate (630 mg, 7.50 mmol) in methylene chloride (11 mL). After stirring 17 hours at ambient temperature, the reaction mixture was diluted with methylene chloride, washed with water (2×) and saturated aqueous sodium chloride, dried over anhydrous sodium sulfate, filtered, concentrated under reduced pressure, and purified by flash column chromatography (3:1 hexanes/ethyl acetate) to produce 2.36 g (90%) of the title compound as a white foam.

$^1$H NMR (400 MHz, CDCl$_3$, major rotamer) δ 7.80 (d 1H), 7.25 (m, 1H), 7.11 (d, 1H), 6.69 (m, 3H), 6.42 (d, 1H), 6.18 (d, 1H), 6.12 (d, 1H), 4.50 (d, 1H), 4.31–4.06 (m, 6H), 3.06 (d, 1H), 2.24 (d, 1H), 1.22 (t, 3H), 0.92 (s, 9H).

EXAMPLE 1D

Ethyl Ester of trans-7-Chloro-5-(2,3-ethylenedioxyphenyl)-1-neopentyl-1,2,3,5-tetrahydro-2-oxo-4,1-benzoxazepine-3-acetic Acid Potassium carbonate (1.34 g, 9.67 mmol) was added to a solution of 3-[{4-chloro-2-[(2,3-ethylenedioxyphen-1-yl)-hydroxy-methyl]-phenyl}-neopentyl-carbamoyl]acrylic acid ethyl ester (2.36 g, 4.84 mmol) in ethanol (25 mL). The resulting mixture was stirred at ambient temperature for 16 hours, diluted with ethyl acetate, washed with water (2×) and saturated aqueous sodium chloride, dried over anhydrous sodium sulfate, and concentrated under reduced pressure to a white solid that was recrystallized with ethyl acetate to produce 1.58 g (67%) of the title compound as a white solid.

$^1$H NMR (400 MHz, CDCl$_3$) δ 7.32 (m, 2H), 7.14 (m, 1H), 6.93 (m, 2H), 6.71 (d, 1H), 6.20 (s, 1H), 4.50 (d, 1H), 4.36 (dd, 1H), 4.22–3.98 (m, 6H), 3.34 (d, 1H), 3.03 (dd, 1H), 2.75 (dd, 1H), 1.23 (t, 3H), 0.90 (s, 9H).

EXAMPLE 1E trans-7-Chloro-5-(2,3-ethylenedioxyphenyl)-1-neopentyl-1,2,3,5-tetrahydro-2-oxo-4,1-benzoxazepine-3-acetic Acid Potassium carbonate (1.18 g, 8.5 mmol) was added to a solution of the ethyl ester of the tide compound (2.08 g, 4.3 mmol) in methanol (300 mL) and water (25 mL). The resulting mixture was heated at 60° C. for 18 hours and then ethanol (25 mL) was added and the resulting solution was heated at 70° C. for 3 hours. After cooling to room temperature, the reaction mixture was concentrated and the resulting residue taken up in water, acidified with an aqueous solution of 1N hydrochloric add and extracted with ethyl acetate (3×). The combined organics were dried over anhydrous magnesium sulfate, filtered, concentrated under reduced pressure to give 1.79 g (91%) of the title compound as a white solid.

$^1$H NMR (300 MHz, CDCl$_3$) δ 0.91 (s, 9H), 2.83 (q, 1H), 3.06 (q, 1H), 3.36 (d, 1H), 4.0–4.27 (c, 4H), 4.31 (q, 1H), 4.51 (d, 1H), 6.2 (s, 1H), 6.74 (d, 1H), 6.9–7.0 (m, 2H), 7.16 (d, 1H), 7.3–7.4 (m, 2H).

EXAMPLE 1F

Ethyl Ester of N-[trans-7-Chloro-5-(2,3-ethylenedioxyphenyl)-1-neopentyl-1,2,3,5-tetrahydro-2-oxo-4,1-benzoxazepine-3-acetyl] isonipecotic Acid 1-(3-Dimethylaminopropyl)-3-ethylcarbodiimide hydrochloride (51 mg, 270 mmol) and ethyl isonipecotate (25 mg, 159 mmol, 25 mL) were added sequentially to a solution of trans-7-chloro-5-(2,3-ethylenedioxyphenyl)-1-neopentyl-1,2,3,5-tetrahydro-2-oxo-4,1-benzoxazepine-3-acetic acid (59 mg, 133 mmol) and methylene chloride (2 mL). After stirring 18 hours at ambient temperature, the reaction mixture was diluted with ethyl acetate, washed with water and saturated aqueous sodium chloride, dried over anhydrous magnesium sulfate, filtered, concentrated under reduced pressure, and purified by flash column chromatography (3:2 hexanes/ethyl acetate) to produce 53 mg (68%) of the title compound as a white foam.

MS (APCI): 599 (M+H$^+$).

$^1$H NMR (400 MHz, CDCl$_3$, rotameric mixture) δ 7.32 (s, 2H), 7.18 (m, 1H), 6.92 (m, 2H), 6.68 (d, 1H), 6.20 (s, 1H), 4.49 (m, 2H), 4.40–4.01 (m, 6H), 3.90 (br d, 1H), 3.34 (d, 1H), 3.11 (m, 2H), 2.80 (m, 2H), 2.49 (m, 1H), 1.91–1.56 (m, 5H), 1.24 (m, 3H), 0.90 (s, 9H).

EXAMPLE 1G

Methyl Ester of (−)-(S)-O-[trans-7-Chloro-5-(2,3-ethylenedioxyphenyl)-1-neopentyl-2-oxo-1,2,3,5-tetrahydro-4,1-benzoxazepin-3-acetyl]lactic Acid and Methyl Ester of (+)-(S)-O-[[trans-7-Chloro-5-(2,3-ethylenedioxyphenyl)-1-neopentyl-2-oxo-1,2,3,5-tetrahydro-4,1-benzoxazepin-3-acetyl]lactic Acid To a solution of 1.0 g (2.17 mmol) trans-7-chloro-5-(2,3-ethylenedioxyphenyl)-1-neopentyl-2-oxo-1,2,3,5-tetrahydro-4,1-benzoxazepin-3-acetic acid and 0.52 ml (5.44 mmol) (S)-methyl lactate in 50 ml dichloromethane cooled to 0° C. under nitrogen was added 0.75 g (3.91 mmol) 1-ethyl-3-(3-dimethylaminopropyl)carbodiimide hydrochloride and 0.31 g (2.5 mmol) 4-dimethylaminopyridine. The solution was stirred overnight at room temperature, then diluted with 50 ml dichloromethane and washed sequentially with 70 ml 1N aqueous hydrochloric acid, 70 ml water, 70 ml saturated aqueous sodium bicarbonate solution and 70 ml brine. The dichloromethane solution was dried over anhydrous sodium sulfate and concentrated in vacuo to yield 0.893 g of white solid. Chromatography on silica gel, eluting with 2:1 hexane diethyl ether yielded 92.2 mg of the less polar diastereomer, 100.8 mg of the more polar diastereomer and 317.4 mg of a mixture. The mixture fraction was chromatographed again on silica gel, eluting with 55:20:25 hexane/diethyl ether/toluene to yield two fractions, one containing predominantly the less polar diastereomer and the other predominantly the more polar diastereomer.

EXAMPLE 1H

Methyl Ester of (−)-(S)-O-[trans-7-Chloro-5-(2,3-ethylenedioxyphenyl)-1-neopentyl-2-oxo-1,2,3,5-tetrahydro-4,1-benzoxazepin-3-acetyl]lactic Acid The fraction in Example 1G containing predominantly the less polar diastereomer was combined with the less polar diastereomer from the first chromatography and recrystallized from 55:20:25 hexane/diethyl ether/toluene to yield 230 mg of the less polar diastereomer.

$^1$H NMR (CDCl$_3$) δ 0.9 (s, 9H); 1.47 (d, 3H); 2.85 (q, 1H); 3.18 (q, 1H); 3.71 (s, 3H); 4.05 (c, 2H); 4.2 (c, 2H); 5.05 (q, 1H); 6.2 (s, 1H). MS (APCI): 546; $[\alpha]_D^{20}$ −235° (methanol).

EXAMPLE 1I

Methyl Ester of (+)-(S)-O-[[trans-7-Chloro-5-(2,3-ethylenedioxyphenyl)-1-neopentyl-2-oxo-1,2,3,5-tetrahydro-4,1-benzoxazepin-3-acetyl]lactic Acid The fraction in Example 1G containing predominantly the more polar diastereomer was combined with the more polar diastereomer from the first chromatography and recrystallized from 55:20:25 hexane/diethyl ether/toluene to yield 230 mg of the more polar diastereomer.

$^1$H NMR (CDCl$_3$) δ 0.91 (s, 9H); 1.46 (d, 3H); 2.89 (q, 1H); 3.07 (q, 1H); 3.72 (s, 3H); 4.05 (c, 2H); 4.2 (c, 2H); 5.1 (q, 1H); 6.23 (s, 1H). MS (APCI): 546; $[\alpha]_D^{20}$ +197° (methanol).

The title compounds of Examples 1J and 1K were prepared according to procedures analogous to those described in Example 10.

EXAMPLE 1J (−)-trans-7-Chloro-5-(2,3-ethylenedioxyphenyl)-1-neopentyl-2-oxo-1,2,3,5-tetrahydro-4,1-benzoxazepin-3-acetic Acid 99% yield. $^1$H NMR identical to that of Example 1E. MS (APCI): 461 (M+H$^+$); $[\alpha]_D^{20}$ −256.4° (methanol).

EXAMPLE 1K (+)-trans-7-Chloro-5-(2,3-ethylenedioxyphenyl)-1-neopentyl-2-oxo-1,2,3,5-tetrahydro-4,1-benzoxazepin-3-acetic Acid 99% yield. $^1$H NMR identical to that of Example 1E. $[\alpha]_D^{20}$ +258.8° (methanol).

The title compound of Example 1L was prepared according to a procedure analogous to that described in Example 2 using the compound of Example 1J.

EXAMPLE 1L

Ethyl Ester of (−)-N-[trans-7-Chloro-5-(2,3-ethylenedioxyphenyl)-1-neopentyl-2-oxo-1,2,3,5-tetrahydro-4,1-benzoxazepin-3-acetyl]isonipecotic Acid 57% yield. $^1$H NMR identical to that of Example 1F; $[\alpha]_D^{20}$ −202.9°.

EXAMPLE 2

Ethyl Ester of N-[trans-7-Chloro-5-(2,3-dimethoxyphenyl)-1-neopentyl-2-oxo-1,2,3,5-tetrahydro-4,1-benzoxazepin-3-acetyl]isonipecotic Acid To a solution of 600 mg (1.30 mmol) trans-7-chloro-5-(2,3-dimethoxyphenyl)-1-neopentyl-2-oxo-1,2,3,5-tetrahydro-4,1-benzoxazepin-3-acetic acid and 0.22 ml (1.43 mmol) ethyl isonipecotate in 20 ml dimethylformamide cooled to 0° C. was added 0.22 ml (1.43 mmol) diethyl cyanophosphonate followed by 0.2 ml triethylamine. The reaction mixture was stirred at room temperature overnight, then poured into 100 ml ice water. The resulting mixture was extracted with 3×70 ml ethyl acetate and the combined ethyl acetate extracts were washed sequentially with 90 ml aqueous 1N hydrochloric acid, 90 ml saturated aqueous sodium bicarbonate solution, 3×90 ml water and 90 ml brine. The ethyl acetate solution was dried over anhydrous sodium sulfate, filtered and concentrated in vacuo. The solid residue was chromatographed on 150 g silica gel, eluting with 3:2 hexane/ethyl acetate to yield 504 mg (65% yield) of the title compound as a white solid.

$^1$H NMR (CDCl$_3$) δ 0.94 (s, 9H); 1.25 (m, 3H); 1.5–2.0 (c, 4H); 2.5 (c, 1H); 2.67–2.9 (m, 2H); 3.05–3.23 (m, 2H); 3.37 (d, 1H); 3.62 (s, 3H); 3.84–3.97 [c and s (3.89, 3H), total 4H]; 4.04 (m, 2H); 4.33 (m, 1H); 4.5 (m, 2H); 6.27 (s, 1H); 6.6 (s, 1H); 6.97 (m, 1H); 7.13–7.37 (c and m, 4H).

The title compounds of Examples 3–9BY were prepared according to procedures analogous to those described in Example 2.

EXAMPLE 3

Ethyl Ester of N-[trans-7-Chloro-5-(2,3-dimethoxyphenyl)-1-neopentyl-2-oxo-1,2,3,5-tetrahydro-4,1-benzoxazepin-3-acetyl]nipecotic Acid 71% yield. $^1$H NMR (CDCl$_3$) δ 0.94 (s, 9H); 1.24 (m, 3H); 1.3–2.15 (c, 5H); 2.3–2.85 (c and m, 3H); 2.9–3.4 [c and δ (3.38, 1H), total 3H]; 3.62 (s, 3H); 3.8–4.04 [c and s (3.89, 3H), total 4H]; 4.13 (m, 2H); 4.5 (c, 2H); 6.27 (s, 1H); 6.6 (s, 1H); 6.97 (m, 1H); 7.16–7.37 (m, 4H).

EXAMPLE 4

Methyl Ester of N-[trans-7-Chloro-5-(2,3-dimethoxyphenyl)-1-neopentyl-2-oxo-1,2,3,5-tetrahydro-4,1-benzoxazepin-3-acetyl]-L-proline 36% yield. $^1$H NMR (CDCl$_3$) δ 0.93 (s, 9H); 1.9–2.24 (c, 4H); 2.7 (q, 1H); 3.2 (q, 1H); 3.35 (d, 1H); 3.6–3.73 [c, s (3.61, 3H) and s (3.68, 3H), total 8H]; 3.89 (s, 3H); 4.4–4.6 (m, 3H); 6.27 (s, 1H); 6.6 (s, 1H); 6.98 (d, 1H); 7.15–7.33 (m, 4H).

EXAMPLE 5

Dimethyl Ester of N-[trans-7-Chloro-5-(2,3-dimethoxyphenyl)-1-neopentyl-2-oxo-1,2,3,5-tetrahydro-4,1-benzoxazepin-3-acetyl]-cis-2,4-piperidinedicarboxylic Acid 46% yield. $^1$H NMR (CDCl$_3$) δ 0.94 9s, 9H); 1.6–3.45 (c and m, 9H); 3.6–3.8 [c, s (3.6, 3H), s (3.67, 3H) and s (3.7, 3H), total 10H]; 3.9 (s, 3H); 4.5 (c, 2H); 6.3 (c, 1H); 6.6 (c, 1H); 7.0 (c, 1H); 7.13–7.5 (c, 4H).

EXAMPLE 6

Ethyl Ester of N-[trans-7-Methyl-5-(2,3-dimethoxyphenyl)-1-neopentyl-2-oxo-1,2,3,5-tetrahydro-4,1-benzoxazepin-3-acetyl]isonipecotic Acid 73% yield. $^1$H NMR (CDCl$_3$) δ 0.94 (s 9H); 1.25 (m, 3H); 1.5–2.0 (c, 4H); 2.15 (s, 3H); 2.5 (c, 1H); 2.7–2.9 (m, 2H); 3.0–3.2 (m, 2H); 3.4 (d, 1H); 3.6 (s 3H); 3.86–4.0 [c and s (3.88, 3H), total 4H]; 4.15 (m, 2H); 4.34 (m, 1H); 4.45–4.56 (m, 2H); 6.29 (s, 1H); 6.4 (m, 1H); 6.95 (q, 1H); 7.1–7.3 (m, 4H).

EXAMPLE 7

Ethyl Ester of N-[trans-7-Methyl-5-(2,3-dimethoxyphenyl)-1-neopentyl-2-oxo-1,2,3,5-tetrahydro-4,1-benzoxazepin-3-acetyl]nipecotic Acid 63% yield. $^1$H NMR (CDCl$_3$) δ 0.94 (s, 9H); 1.25 (m, 3H); 1.35–2.17 [c and s (2.16, 3H), total 8H]; 2.25–2.83 (c and m, 3H); 2.9–3.44 [c and d (3.4, 1H), total 3H]; 3.6 (s, 3H); 3.8–4.2 [c, s (3.88, 3H) and m (4.12, 2H), total 6H]; 4.5 (m, 2H); 6.29 (s, 1H); 6.39 (s, 1H); 6.95 (m, 1H); 7.1–7.3 (m, 4H).

EXAMPLE 8

Ethyl Ester of N-[trans-7-Chloro-5-(2,3-ethylenedioxyphenyl)-1-neopentyl-2-oxo-1,2,3,5-tetrahydro-4,1-benzoxazepin-3-acetyl]nipecotic Acid 71% yield. $^1$H NMR (CDCl$_3$) δ 0.91 (s, 9H); 1.24 (m, 3H); 1.3–2.13 (c, 5H); 2.2–3.4 [c and d (3.35, 1H), total 6H]; 3.9–4.23 (c, 8H); 4.5 (c, 2H); 6.2 (s, 1H); 6.7 (s, 1H); 6.94 (m, 2H); 7.33 (s, 2H).

EXAMPLE 9

Methyl Ester of N-[trans-7-Chloro-5-(2,3-ethylenedioxyphenyl)-1-neopentyl-2-oxo-1,2,3,5-tetrahydro-4,1-benzoxazepin-3-acetyl]-L-proline 74% yield. $^1$H NMR (CDCl$_3$) δ 0.9, 0.91 (2s, 9H); 1.85–2.25 (c, 4H); 2.7, 2.88, 3.2 (m, total 2H); 3.33 (d, 1H); 3.6–3.78 [c and s (3.67, 3.7, 3H), total 5H]; 4.05 (c, 2H); 4.2 (c, 2H); 4.4–4.6 (c, 3H); 6.2 (m, 1H); 6.7 (m, 1H); 6.9–7.36 (m, 5H).

EXAMPLE 9E

Methyl Ester of N-[trans-7-Chloro-5-(2,3-dimethoxyphenyl)-1-neopentyl-2-oxo-1,2,3,5-tetrahydro-4,1-benzoxazepin-3-acetyl]-L-pipecolinic Acid 68% yield. $^1$H NMR (CDCl$_3$) δ 0.94 (s, 3H); 3.62 (s, 3H); 3.69, 3.71 (2s, 3H); 3.89 (s, 3H); 4.5 (m, 2H); 6.29 (d, 1H); 6.59 (m, 1H).

EXAMPLE 9F

Methyl Ester of N-[trans-7-Chloro-5-(2,3-ethylenedioxyphenyl)-1-neopentyl-2-oxo-1,2,3,5-tetrahydro-4,1-benzoxazepin-3-acetyl]-L-pipecolinic Acid 68% yield. $^1$H NMR (CDCl$_3$) δ 0.91 (s, 9H); 4.05 (c, 2H); 4.2 (c, 2H); 5.25, 5.35 (c, 1H); 6.2 (d, 1H); 6.7 (br, 1H).

EXAMPLE 9G

Ethyl Ester of N-[trans-7-Chloro-5-(2,4-dimethoxyphenyl)-1-neopentyl-2-oxo-1,2,3,5-tetrahydro-4,1-benzoxazepin-3-acetyl]isonipecotic Acid 73% yield. $^1$H NMR (CDCl$_3$) δ 0.92 (s, 9H); 1.25 (m, 3H); 3.6 (s, 3H); 3.86 (s, 3H); 4.14 (m, 2H); 6.2 (s, 1H); 6.46 (s, 1H).

EXAMPLE 9H

Ethyl Ester of N-[trans-7-Chloro-(2,4-dimethoxyphenyl)-1-neopentyl-2-oxo-1,2,3,5-tetrahydro-4,1-benzoxazepin-3-acetyl]nipecotic Acid 79% yield. $^1$H NMR (CDCl$_3$) δ 0.92 (s, 9H); 1.24 (m, 3H); 3.6 (s, 3H); 3.86 (s, 3H); 4.12 (m, 2H); 4.48 (c, 2H); 6.2 (br, 1H); 6.46 (d, 1H).

EXAMPLE 9I

Methyl Ester of N-[trans-7-Chloro-5-(2,4-dimethoxyphenyl)-1-neopentyl-2-oxo-1,2,3,5-tetrahydro-4,1-benzoxazepin-3-acetyl]-L-pipecolinic Acid 69% yield. $^1$H NMR (CDCl$_3$) δ 0.92 (s, 9H); 3.6 (d, 3H); 3.73, 3.75 (2s, 3H); 3.85 (s, 3H); 5.25, 5.35 (c, 1H); 6.2 (d, 1H); 6.46 (d, 1H).

EXAMPLE 9J

Ethyl Ester of N-[trans-7-Chloro-5-(2,3,4-trimethoxyphenyl)-1-neopentyl-2-oxo-1,2,3,5-tetrahydro-4,1-benzoxazepin-3-acetyl]nipecotic Acid 78% yield. $^1$H NMR (CDCl$_3$) δ 0.94 (s, 9H); 3.65 (s, 3H); 3.85 (s, 3H); 3.92 (s, 3H); 4.51 (c, 2H); 6.18 (br, 1H); 6.65 (br, 1H).

EXAMPLE 9K

Ethyl Ester of N-[trans-7-Methyl-5-(2,1-ethylenedioxyphenyl)-1-neopentyl-2-oxo-1,2,3,5-tetrahydro-4,1-benzoxazepin-3-acetyl]isonipecotic Acid 60% yield. $^1$H NMR (CDCl$_3$) δ 0.91 (s, 9H); 1.26 (c, 3H); 2.19 (s, 3H); 3.9–4.22 (c, 7H); 4.33 (m, 1H), 6.22 (s, 1H); 6.5 (br, 1H).

EXAMPLE 9L

Ethyl Ester of N-[trans-7-Chloro-5-(2,3-ethylenedioxy-4-methoxyphenyl)-1-neopentyl-2-oxo-1,2,3,5-tetrahydro-4,1-benzoxazepin-3-acetyl]isonipecotic Acid 65% yield. $^1$H NMR (CDCl$_3$) δ 0.9 (s, 9H); 1.28 (c, 3H); 3.94.2 (c and s at 3.93, 9H); 6.15 (s, 1H).

EXAMPLE 9M

Ethyl Ester of N-[trans-7-Chloro-5-(2-ethoxy-4-methoxyphenyl)-1-neopentyl-2-oxo-1,2,3,5-tetrahydro-4,1-benzoxazepin-3-acetyl]isonipecotic Acid 70% yield. $^1$H NMR (CDCl$_3$) δ 0.92 (s, 9H); 1.18 (t, 3H); 1.25 (m, 3H); 3.85 (s, 3H); 3.9 (m, 2H); 4.12 (m, 2H); 4.33 (c, 1H); 6.23 (s, 1H); 6.45 (s, 1H).

EXAMPLE 9M1

Ethyl Ester of N-[trans-7-Methyl-5-(2,4-dimethoxyphenyl)-1-neopentyl-2-oxo-1,2,3,5-tetrahydro-4,1-benzoxazepin-3-acetyl]isonipecotic Acid 81% yield. $^1$H NMR (CDCl$_3$) δ 0.92 (s, 9H); 1.25 (m, 3H); 2.18 (s, 3H); 3.59 (s, 3H); 3.86 (s, 3H); 4.34 (c, 1H); 6.23 (s, 1H); 6.45 (br, 1H).

EXAMPLE 9N

Methyl Ester of N-[trans-7-Chloro-5-(2,3-dimethoxyphenyl)-1-neopentyl-2-oxo-1,2,3,5-tetrahydro-4,1-benzoxazepin-3-acetyl]-trans-4-hydroxy-L-proline 64% yield. $^1$H NMR (CDCl$_3$) δ 0.92, 0.94 (2s, 9H); 3.61 (s, 3H); 3.74, 3.78 (2s, 3H); 3.88, 3.89 (2s, 3H); 6.26 (d, 1H), 6.59 (d, 1H).

EXAMPLE 9O

Methyl Ester of N-[trans-7-Chloro-5-(2,3-dimethoxyphenyl)-1-neopentyl-2-oxo-1,2,3,5-tetrahydro-4,1-benzoxazepin-3-acetyl]-cis-4-hydroxy-D-proline 42% yield. $^1$H NMR (CDCl$_3$) δ 0.93, 0.94 (2s, 9H); 3.6 (s, 3H); 3.76 (2s, 3H); 3.89 (s, 3H); 4.66 (t, 1H); 6.27 (m, 1H).

EXAMPLE 9P

Methyl Ester of N-[trans-7-Chloro-5-(2,3-ethylenedioxyphenyl)-1-neopentyl-2-oxo-1,2,3,5-tetrahydro-4,1-benzoxazepin-3-acetyl]-trans-4-hydroxy-L-proline 70% yield. $^1$H NMR (CDCl$_3$) δ 0.89, 0.91 (2s, 9H); 3.73 (2s, 3H); 4.03 (c, 2H); 4.18 (c, 2H); 6.2 (d, 1H); 6.69 (d, 1H).

EXAMPLE 9Q

Methyl Ester of N-[trans-7-Chloro-5-(2,3-ethylenedioxyphenyl)-1-neopentyl-2-oxo-1,2,3,5-tetrahydro-4,1-benzoxazepin-3-acetyl]-cis-4-hydroxy-D-proline 42% yield. $^1$H NMR (CDCl$_3$) δ 0.89, 0.91 (2s, 9H); 3.76 (2s, 3H); 4.04 (m, 2H); 4.19 (m, 2H); 6.2 (d, 1H).

EXAMPLE 9R

Ethyl Ester of N-[trans-7-Chloro-5-(2-chloro-4-methoxyphenyl)-1-neopentyl-2-oxo-1,2,3,5-tetrahydro-4,1-benzoxazepin-3-acetyl]isonipecotic Acid 47% yield. $^1$H NMR (CDCl$_3$) δ 0.92 (s, 9H), 1.25 (m, 3H); 3.86(s, 3H); 4.13 (m, 2H); 6.2 (s, 1H); 6.54 (br, 1H).

EXAMPLE 9S

Ethyl Ester of N-[trans-7-Chloro-5-(2-chloro-4-methoxyphenyl)-1-neopentyl-2-oxo-1,2,3,5-tetrahydro-4,1-benzoxazepin-3-acetyl]nipecotic Acid 75% yield. $^1$H NMR (CDCl$_3$) δ 0.93 (s, 9h); 1.25 (m, 3H); 3.86 (s, 3H); 4.13 (m, 2H); 6.2 (s, 1H); 6.54 (s, 1H).

EXAMPLE 9T

Ethyl Ester of N-[trans-7-Methyl-5-(2,3-ethylenedioxyphenyl)-1-neopentyl-2-oxo-1,2,3,5-tetrahydro-4,1-benzoxazepin-3-acetyl]nipecotic Acid 56% yield. $^1$H NMR (CDCl$_3$) δ 0.91 (s, 9H); 2.2 (s, 3H); 3.98–4.12 (c, 6H); 6.24 (s, 1H); 6.5 (s, 1H).

EXAMPLE 9U

Ethyl Ester of N-[trans-7-Chloro-5-(2,3-ethylenedioxy-4-methoxyphenyl)-1-neopentyl-2-oxo-1,2,3,5-tetrahydro-4,1-benzoxazepin-3-acetyl]nipecotic Acid 61% yield. $^1$H NMR (CDCl$_3$) δ 0.9 (s, 9H); 3.93 (s, 3H); 3.98–4.12 (c, 6H); 6.14 (s, 1H); 6.62 (d, 1H).

EXAMPLE 9V

Ethyl Ester of N-[trans-7-Methyl-5-(2,4-dimethoxyphenyl)-1-neopentyl-2-oxo-1,2,3,5-tetrahydro-4,1-benzoxazepin-3-acetyl]nipecotic Acid 82% yield. $^1$H NMR (CDCl$_3$) δ 0.92 (s, 9H); 1.24 (m, 3H); 2.18 (s, 3H); 3.59 (s, 3H); 3.86 (s, 3H); 4.12 (c, 2H); 6.23 (s, 1H); 6.45 (m, 2H); 6.61 (d, 1H).

EXAMPLE 9W

Ethyl Ester of N-[trans-7-Chloro-5-(2-methoxyphenyl)-1-neopentyl-2-oxo-1,2,3,5-tetrahydro-4,1-benzoxazepin-3-acetyl]isonipecotic Acid 82% yield. $^1$H NMR (CDCl$_3$) δ 0.92 (s, 9H); 1.24 (m, 3H); 3.61 (s, 3H); 4.12 (m, 2H); 6.25 (s, 1H); 6.6 (br, 1H).

EXAMPLE 9X

Ethyl Ester of N-[trans-7-Chloro-5-(2-chloro-3,4-dimethoxyphenyl)-1-neopentyl-2-oxo-1,2,3,5-tetrahydro-4,1-benzoxazepin-3-acetyl]isonipecotic Acid 85% yield. $^1$H NMR (CDCl$_3$) δ 0.92 (s, 9H); 1.24 (m, 3H); 3.85 (s, 3H); 3.94 (s, 3H); 4.12 (m, 2H); 6.19 (s, 1H); 6.54 (c, 1H).

EXAMPLE 9Y

Ethyl Ester of N-[trans-7-Chloro-5-(2-trifluoromethoxyphenyl)-1-neopentyl-2-oxo-1,2,3,5-tetrahydro-4,1-benzoxazepin-3-acetyl]isonipecotic Acid 86% yield. $^1$H NMR (CDCl$_3$) δ 0.92 (s, 9H); 1.24 (m, 3H); 4.13 (m, 2H); 4.32 (c, 1H); 6.25 (s, 1H); 6.48 (br, 1H).

EXAMPLE 9Z

Ethyl Ester of N-[trans-7-Chloro-5-(2-methoxyphenyl)-1-neopentyl-2-oxo-1,2,3,5-tetrahydro-4,1-benzoxazepin-3-acetyl]nipecotic Acid 85% yield. $^1$H NMR (CDCl$_3$) δ 0.92 (s, 9H); 1.23 (m, 3H); 4.11 (m, 2H); 3.61 (s, 3H); 6.25 (s, 1H); 6.6 (s, 1H).

EXAMPLE 9AA

Ethyl Ester of N-[trans-7-Chloro-5-(2-chloro-3,4-dimethoxyphenyl)-1-neopentyl-2-oxo-1,2,3,5-tetrahydro-4,1-benzoxazepin-3-acetyl]nipecotic Acid 77% yield. $^1$H NMR (CDCl$_3$) δ 0.92 (s, 9H); 1.24 (m, 3H); 3.85 (s, 3H), 3.94 (s, 3H); 4.12 (m, 2H); 6.18 (s, 1H); 6.53 (s, 1H).

EXAMPLE 9AB

Ethyl Ester of N-[trans-7-Chloro-5-(2-trifluoromethoxyphenyl)-1-neopentyl-2-oxo-1,2,3,5-tetrahydro-4,1-benzoxazepin-3-acetyl]nipecotic Acid 90% yield. $^1$H NMR (CDCl$_3$) δ 0.9 (s, 9H); 1.24 (m, 3H); 4.11 (m, 2H); 6.25 (s, 1H); 6.49 (s, 1H).

EXAMPLE 9AC

Methyl Ester of N-[trans-7-Chloro-5-(2,3-dimethoxyphenyl)-1-neopentyl-2-oxo-1,2,3,5-tetrahydro-4,1-benzoxazepin-3-acetyl]azetidine-3-carboxylic Acid 17% yield. $^1$H NMR (CDCl$_3$) δ 0.94 (s, 9H); 3.61 (s, 3H); 3.74, 3.76 (2s, 3H); 3.89 (s, 3H); 6.26 (d, 1H); 6.6 (br, 1H).

EXAMPLE 9AD

Methyl Ester of N-[trans-7-Chloro-5-(2,3-ethylenedioxyphenyl)-1-neopentyl-2-oxo-1,2,3,5-tetrahydro-4,1-benzoxazepin-3-acetyl]azetidine-3-carboxylic Acid 19% yield. $^1$H NMR (CDCl$_3$) δ 0.92 (s, 9H); 3.75, 3.76 (2s, 3H); 4.04 (c, 2H), 4.19 (c, 2H); 6.2 (d, 1H); 6.7 (m, 1H).

EXAMPLE 9AE

Ethyl Ester of N-[trans-7-Methylthio-5-(2,3-dimethoxyphenyl)-1-neopentyl-2-oxo-1,2,3,5-tetrahydro-4,1-benzoxazepin-3-acetyl]isonipecotic Acid 60% yield. $^1$H NMR (CDCl$_3$) δ 0.94 (s, 9H); 1.25 (,3H); 2.28 (s, 3H); 3.59 (s, 3H); 3.88 (s, 3H); 4.13 (m, 2H); 4.33 (m, 1H); 6.3 (s, 1H); 6.5 (s, 1H).

EXAMPLE 9AF

Ethyl Ester of N-[trans-7-Methylthio-5-(2,3-dimethoxyphenyl)-1-neopentyl-2-oxo-1,2,3,5-tetrahydro-4,1-benzoxazepin-3-acetyl]nipecotic Acid 69% yield. $^1$H NMR (CDCl$_3$) δ 0.94 (s, 9H); 1.24 (c, 3H); 2.28 (s, 3H); 3.6 (s, 3H); 3.88 (s, 3H); 4.12 (c, 2H); 6.3 (s, 1H); 6.51 (s, 1H).

EXAMPLE 9AG

Ethyl Ester of N-[trans-7-Methyl-5-(2,3-methylenedioxyphenyl)-1-neopentyl-2-oxo-1,2,3,5-tetrahydro-4,1-benzoxazepin-3-acetyl]isonipecotic Acid 63% yield. $^1$H NMR (CDCl$_3$) δ 0.9 (s, 3H); 1.25 (m, 3H); 2.21 (s, 3H); 4.13 (c, 2H); 4.33 (m, 1H); 5.87 (d, 2H); 6.15 (s, 1H); 6.57 (br, 1H).

EXAMPLE 9AG1

Ethyl Ester of N-[trans-7-Methyl-5-(2,3-methylenedioxyphenyl)-1-neopentyl-2-oxo-1,2,3,5-tetrahydro-4,1-benzoxazepin-3-acetyl]nipecotic Acid 61% yield. $^1$H NMR (CDCl$_3$) δ 0.9 (s, 3H); 1.24 (m, 3H); 2.22 (s, 3H); 4.12 (c, 2H); 5.87 (d, 2H); 6.16 (s, 1H); 6.58 (s, 1H).

EXAMPLE 9AH

Ethyl Ester of N-[trans-7-Methylthio-5-(2,3-ethylenedioxyphenyl)-1-neopentyl-2-oxo-1,2,3,5-tetrahydro-4,1-benzoxazepin-3-acetyl]isonipecotic Acid 62% yield. $^1$H NMR (CDCl$_3$) δ 0.91 (s, 9H); 1.26 (c, 3H); 2.31 (s, 3H); 4.0–4.12 (c, 6H); 6.22 (m, 1H); 6.59 (s, 1H).

EXAMPLE 9AI

Ethyl Ester of N-[trans-7-Methylthio-5-(2,3-ethylenedioxyphenyl)-1-neopentyl-2-oxo-1,2,3,5-tetrahydro-4,1-benzoxazepin-3-acetyl]nipecotic Acid 53% yield. $^1$H NMR (CDCl$_3$) δ 0.91 (s, 9H); 1.24 (m, 3H); 2.31 (s, 3H); 3.98–4.16 (c, 6H); 6.23 (s, 1H); 6.6 (s, 1H).

EXAMPLE 9AJ

Ethyl Ester of N-[trans-7-Chloro-(2,3-dimethoxyphenyl)-1-cyclopropylmethyl-2-oxo-1,2,3,5-tetrahydro-4,1-benzoxazepin-3-acetyl]isonipecotic Acid 82% yield. $^1$H NMR (CDCl$_3$) δ 0.2 (c, 1H); 0.36–0.6 (c, 3H); 1.1 (c, 1H); 1.3 (m, 3H); 3.53 (s, 3H); 3.88 (s, 3H); 4.14 (m, 2H); 6.24 (s, 1H); 6.64 (m, 1H).

EXAMPLE 9AK

Ethyl Ester of N-[trans-7-Chloro-5-(2,3-dimethoxyphenyl)-1-cyclopropylmethyl-2-oxo-1,2,3,5-tetrahydro-4,1-benzoxazepin-3-acetyl]nipecotic Acid 63% yield. $^1$H NMR (CDCl$_3$) δ 0.18 (c, 1H); 0.33–0.56 (c, 3H); 1.1 (c, 1H); 1.12 (m, 3H); 3.53 (s, 3H); 3.88 (s, 3H); 4.12 (c, 2H); 6.24 (s, 1H); 6.65 (d, 1H).

EXAMPLE 9AL

Ethyl Ester of N-[trans-7-Chloro-5-(3,4-ethylenedioxyphenyl)-1-neopentyl-2-oxo-1,2,3,5-tetrahydro-4,1-benzoxazepin-3-acetyl]isonipecotic Acid 66% yield. $^1$H NMR (CDCl$_3$) δ 0.89 (s, 9H); 1.25 (m, 3H); 4.14 (m, 2H); 4.29 (s, 4H); 5.88 (s, 1H); 6.7 (d, 1H).

EXAMPLE 9AM

Ethyl Ester of N-[trans-7-Chloro-5-(3,4-ethylenedioxyphenyl)-1-neopentyl-2-oxo-1,2,3,5-tetrahydro-4,1-benzoxazepin-3-acetyl]nipecotic Acid 54% yield. $^1$H NMR (CDCl$_3$) δ 0.9 (s, 9H); 1.25 (m, 3H); 4.14 (m, 2H); 4.31 (s, 4H); 5.89 (s, 1H); 6.7 (b, 1H).

EXAMPLE 9AN

Ethyl Ester of N-[trans-7,8-Ethylenedioxy-5-(2,3-dimethoxyphenyl)-1-neopentyl-2-oxo-1,2,3,5-tetrahydro-4,1-benzoxazepin-3-acetyl]isonipecotic Acid 80% yield. $^1$H NMR (CDCl$_3$) δ 0.96 (s, 9H); 1.28 (m, 3H); 3.63 (s, 3H); 3.86 (s, 3H); 4.02 (m, 2H); 4.08–4.24 (c, 4H); 6.1 (d, 1H); 6.23 (s, 1H).

EXAMPLE 9AO

Ethyl Ester of N-[trans-7,8-Ethylenedioxy-5-(2,3-dimethoxyphenyl)-1-neopentyl-2-oxo-1,2,3,5-tetrahydro-4,1-benzoxazepin-3-acetyl]nipecotic Acid 71% yield. $^1$H NMR (CDCl$_3$) δ 0.96 (s, 9H); 1.2–1.35 (m, 3H); 3.63 (s, 3H); 3.86 (s, 3H); 3.984.25 (m and c, 6H); 6.11 (s, 1H).

EXAMPLE 9AP

Ethyl Ester of N-[trans-7-Methyl-5-(2-methoxyphenyl-1-neopentyl-2-oxo-1,2,3,5-tetrahydro-4,1-benzoxazepin-3-acetyl]isonipecotic Acid 71% yield. $^1$H NMR (CDCl$_3$) δ 0.93 (s, 9H); 1.24 (t, 3H); 2.16 (s, 3H); 3.62 (s, 3H); 4.13 (q, 2H); 4.35 (c, 1H); 6.3 (s, 1H); 6.41 (br, 1H).

EXAMPLE 9AQ

Ethyl Ester of N-[trans-7-Methylthio-5-(2-trifluoromethoxyphenyl)-1-neopentyl-2-oxo-1,2,3,5-tetrahydro-4,1-benzoxazepin-3-acetyl]isonipecotic Acid 75% yield. $^1$H NMR (CDCl$_3$) δ 0.9 (s, 9H); 1.24 (m, 3H); 2.26(s, 3H); 4.12 (m, 2H); 4.34 (m, 1H); 6.28 (s, 1H); 6.38 (s, 1H).

EXAMPLE 9AR

Ethyl Ester of N-[trans-7-Methylthio-5-(2-methoxyphenyl)-1-neopentyl-2-oxo-1,2,3,5-tetrahydro-4,1-benzoxazepin-3-acetyl]isonipecotic Acid 59% yield. $^1$H NMR (CDCl$_3$) δ 0.93 (s, 9H); 1.25 (t, 3H); 2.28 (s, 3H); 3.61 (s, 3H); 4.13 (q, 2H); 4.34 (m, 1H); 6.29 (s, 1H); 6.5 (s, 1H).

EXAMPLE 9AS

Ethyl Ester of N-[trans-7-Methyl-5-(2-trifluoromethoxyphenyl)-1-neopentyl-2-oxo-1,2,3,5-tetrahydro-4,1-benzoxazepin-3-acetyl)isonipecotic Acid 73% yield. $^1$H NMR (CDCl$_3$) δ 0.9 (s, 9H); 1.24 (m, 3H); 2.16 (s, 3H); 4.14 (m, 2H); 4.35 (c, 1H); 6.29 (s, 1H); 7.16 (d, 1H).

EXAMPLE 9AT

Ethyl Ester of N-[trans-7-Methyl-5-(2-methoxyphenyl)-1-neopentyl-2-oxo-1,2,3,5-tetrahydro-4,1-benzoxazepin-3-acetyl]nipecotic Acid 68% yield. $^1$H NMR (CDCl$_3$) δ 0.9 (s, 9H); 1.24 (m, 3H); 2.19 (s, 3H); 3.64 (s, 3H); 4.12 (m, 2H); 6.3 (s, 1H); 6.4 (s, 1H).

EXAMPLE 9AU

Ethyl Ester of N-[trans-7-Methylthio-5-(2-trifluoromethoxyphenyl)-1-neopentyl-2-oxo-1,2,3,5-tetrahydro-4,1-benzoxazepin-3-acetyl]nipecotic Acid 64% yield. $^1$H NMR (CDCl$_3$) δ 0.92 (s, 9H); 1.23 (m, 3H); 2.28 (s, 3H); 4.12 (m, 2H); 4.5 (d, 1H); 6.28 (s, 1H); 6.38 (s, 1H).

EXAMPLE 9AV

Ethyl Ester of N-[trans-7-Methylthio-5-(2-methoxyphenyl)-1-neopentyl-2-oxo-1,2,3,5-tetrahydro-4,1-benzoxazepin-3-acetyl]nipecotic Acid 76% yield. $^1$H NMR (CDCl$_3$) δ 0.93 (s, 9H); 1.25 (m, 3H); 2.29 (s, 3H); 3.62 (s, 3H); 4.12 (m, 2H); 6.3 (s, 1H); 6.5 (s, 1H).

EXAMPLE 9AV1

Ethyl Ester of N-[trans-7-Methyl-5-(2-trifluoromethoxyphenyl)-1-neopentyl-2-oxo-1,2,3,5-tetrahydro-4,1-benzoxazepin-3-acetyl]nipecotic Acid 58% yield. $^1$H NMR (CDCl$_3$) 0.9 (s, 9H); 1.25 (m, 3H); 2.19 (s, 3H); 4.12 (m, 2H); 6.28 (s,1H).

EXAMPLE 9AW

Ethyl Ester of N-[trans-7-Methylthio-5-(2,3-methylenedioxyphenyl)-1-neopentyl-2-oxo-1,2,3,5-tetrahydro-4,1-benzoxazepin-3-acetyl]isonipecotic Acid 64% yield. $^1$H NMR (CDCl$_3$) δ 0.9 (s, 9H); 1.25 (m, 3H); 2.34 (s, 3H); 4.12 (m, 2H); 4.31 (c, 1H); 5.88 (d, 2H); 6.14 (s, 1H).

EXAMPLE 9AX

Ethyl Ester of N-[trans-7-Methylthio-5-(2,3-methylenedioxyphenyl)-1-neopentyl-2-oxo-1,2,3,5-tetrahydro-4,1-benzoxazepin-3-acetyl]nipecotic Acid 49% yield. $^1$H NMR (CDCl$_3$) δ 0.9 (s, 9H); 1.25 (m, 3H); 2.34 (s, 3H); 4.12 (m, 2H); 4.54 (c, 1H); 5.87 (d, 2H); 6.15 (s, 1H).

EXAMPLE 9AY

Ethyl Ester of N-[trans-7-Chloro-5-(3,4-methylenedioxyphenyl)-1-neopentyl-2-oxo-1,2,3,5-tetrahydro-4,1-benzoxazepin-3-acetyl]isonipecotic Acid 54% yield. $^1$H NMR (CDCl$_3$) δ 0.9 (s, 9H); 1.25 (m, 3H); 4.12 (m, 2H); 4.32 (m, 1H); 5.91 (s, 1H); 6.03 (d, 2H).

EXAMPLE 9AZ

Ethyl Ester of N-[trans-7-Chloro-5-(3,4-methylenedioxyphenyl)-1-neopentyl-2-oxo-1,2,3,5-tetrahydro-4,1-benzoxazepin-3-acetyl]nipecotic Acid 60% yield. $^1$H NMR (CDCl$_3$) δ 0.9 (s, 9H); 1.24 (m, 3H); 4.12 (m, 2H); 5.91 (s, 1H); 6.03 (d, 2H).

EXAMPLE 9BA

Ethyl Ester of N-[trans-7-Chloro-5-(2,3-methylenedioxyphenyl)-1-neopentyl-2-oxo-1,2,3,5-tetrahydro-4,1-benzoxazepin-3-acetyl]isonipecotic Acid 58% yield. $^1$H NMR (400 MHz, CDCl$_3$) δ 0.88 (s, 9H); 1.24 (m, 3H); 4.11 (m, 2H); 5.88 (d, 2H); 6.1 (s, 1H).

EXAMPLE 9BB

Methyl Ester of N-[trans-7-Chloro-5-(2,3-methylenedioxyphenyl)-1-neopentyl-2-oxo-1,2,3,5-tetrahydro-4,1-benzoxazepin-3-acetyl]-L-proline 74% yield. $^1$H NMR (400 MHz, CDCl$_3$) δ 0.85 (s, 9H); 3.84 (2s, 3H); 5.84 (d, 2H); 6.09 (d, 2H).

EXAMPLE 9BC

Ethyl Ester of N-[trans-7-Chloro-5-(2,3-methylenedioxyphenyl)-1-neopentyl-2-oxo-1,2,3,5-tetrahydro-4,1-benzoxazepin-3-acetyl]nipecotic Acid 50% yield. $^1$H NMR (400 MHz, CDCl$_3$) δ 0.88 (s, 9H); 1.23 (m, 3H); 4.11 (m, 2H); 5.87 (m, 2H); 6.12 (s, 1H).

EXAMPLE 9BD

Ethyl Ester of N-[trans-7-Methoxy-5-(2,3-dimethoxyphenyl))-1-neopentyl-2-oxo-1,2,3,5-tetrahydro-4,1-benzoxazepin-3-acetyl]nipecotic Acid 67% yield. $^1$H NMR (400 MHz, CDCl$_3$) δ 0.93 (s, 9H); 1.22 (m, 3H); 3.59 (s, 6H); 3.85 (s, 3H); 4.11 (m, 2H); 6.14 (m, 1H); 6.29 (m, 1H).

EXAMPLE 9BE

Ethyl Ester of N-[trans-7-Methoxy-(2,3-dimethoxyphenyl)-1-neopentyl-2-oxo-1,2,3,5-tetrahydro-4,1-benzoxazepin-3-acetyl]isonipecotic Acid 12% yield. $^1$H NMR (400 MHz, CDCl$_3$) δ 0.94 (s, 9H); 1.24 (m, 3H); 3.61 (s, 6H); 3.87 (s, 3H); 4.13 (m, 2H); 6.16 (m, 1H); 6.3 (s, 1H).

EXAMPLE 9BF

Ethyl Ester of N-[trans-7-Trifluoromethoxy-5-(2,3-dimethoxyphenyl)-1-neopentyl-2-oxo-1,2,3,5-tetrahydro-4,1-benzoxazepin-3-acetyl]nipecotic Acid 72% yield. $^1$H NMR (CDCl$_3$) δ 0.94 (s, 9H); 1.26 (t, 3H); 3.58 (s, 3H); 3.89 (s, 3H); 4.12 (m, 2H); 6.3 (s, 1H).

EXAMPLE 9BG

Ethyl Ester of N-[trans-7-Trifluoromethoxy-5-(2,3-dimethoxyphenyl)-1-neopentyl-2-oxo-1,2,3,5-tetrahydro-4,1-benzoxazepin-3-acetyl]isonipecotic Acid 78% yield. $^1$H NMR (CDCl$_3$) δ 0.94 (s, 9H); 1.25 (m, 3H); 3.58 (s, 3H); 3.88 (s, 3H); 4.13 (m, 2H); 6.3 (s, 1H); 6.48 (b, 1H).

EXAMPLE 9BH

Ethyl Ester of N-[trans-7-Methoxy-5-(2,3-ethylenedioxyphenyl)-1-neopentyl-2-oxo-1,2,3,5-tetrahydro-4,1-benzoxazepin-3-acetyl]nipecotic Acid 62% yield. $^1$H NMR (CDCl$_3$) δ 0.91 (s, 9H); 1.24 (m, 3H); 3.65 (s, 3H); 3.95–4.22 (c, 6H); 6.25 (m, 1H).

EXAMPLE 9BH1

Ethyl Ester of N-[trans-7-Methoxy-5-(2,3-ethylenedioxyphenyl)-1-neopentyl-2-oxo-1,2,3,5-tetrahydro-4,1-benzoxazepin-3-acetyl]isonipecotic Acid 69% yield $^1$H NMR (400 MHz, CDCl$_3$) δ 0.9 (s, 9H); 1.24 (m, 3H); 3.64 (s, 3H); 3.9–4.22 (c, 6H); 6.24 (s and m, 2H).

EXAMPLE 9BI

Ethyl Ester of N-[trans-7-Trifluoromethoxy-5-(2,3-ethylenedioxyphenyl)-1-neopentyl-2-oxo-1,2,3,5-tetrahydro-4,1-benzoxazepin-3-acetyl]isonipecotic Acid 67% yield. $^1$H NMR (CDCl$_3$) δ 0.9 (s, 9H); 1.24 (m, 3H); 3.9–4.22 (c, 6H); 6.2 (s, 1H); 6.55 (b, 1H).

EXAMPLE 9BJ

Ethyl Ester of N-[trans-7-Trifluoromethoxy-5-(2,3-ethylenedioxyphenyl)-1-neopentyl-2-oxo-1,2,3,5-tetrahydro-4,1-benzoxazepin-3-acetyl]nipecotic Acid 78% yield. $^1$H NMR (400 MHz, CDCl$_3$) δ 0.89 (s, 9H); 1.24 (m, 3H); 3.9–4.22 (c, 6H); 6.19 (m, 1H); 6.54 (s, 1H).

EXAMPLE 9BK

Ethyl Ester of N-[trans-7-Trifluoromethoxy-5-(2,3-methylenedioxyphenyl)-1-neopentyl-2-oxo-1,2,3,5-tetrahydro-4,1-benzoxazepin-3-acetyl]isonipecotic Acid 85% yield. $^1$H NMR (CDCl$_3$) δ 0.89 (s, 9H); 1.25 (m, 3H); 4.13 (m, 2H); 5.87 (m, 2H); 6.13 (s, 1H); 6.55 (br, 1H).

EXAMPLE 9BL

Ethyl Ester of N-[Trans-7-Trifluoromethoxy-5-(2,3-methylenedioxyphenyl)-1-neopentyl-2-oxo-1,2,3,5-tetrahydro-4,1-benzoxazepin-3-acetyl]nipecotic Acid 49% yield. $^1$H NMR (400 MHz, CDCl$_3$) 0.88 (2s, 9H); 1.26 (m, 3H); 4.12 (m, 2H); 5.85 (br, 2H); 6.12(br, 1H).

EXAMPLE 9BM

Ethyl Ester of N-[trans-7-Methoxy-5-(2,3-methylenedioxyphenyl)-1-neopentyl-2-oxo-1,2,3,5-tetrahydro-4,1-benzoxazepin-3-acetyl]isonipecotic Acid 51% yield. $^1$H NMR (CDCl$_3$) 0.95 (s, 9H); 1.3 (m, 3H); 3.84 (s, 3H); 4.14 (q, 2H); 5.9 (b, 2H); 6.0 (d, 1H).

EXAMPLE 9BN

Ethyl Ester of N-[trans-7-Methoxy-5-(2,3-methylenedioxyphenyl)-1-neopentyl-2-oxo-1,2,3,5-tetrahydro-4,1-benzoxazepin-3-acetyl]nipecotic Acid 50% yield. $^1$H NMR (400 MHz, CDCl$_3$) 0.92 (s, 9H); 1.3 (m, 3H); 3.82 (s, 3H); 4.14 (m, 2H); 5.88 (m, 2H); 5.98 (m, 1H).

EXAMPLE 9BQ

Ethyl Ester of N-[trans-7-Trifluoromethoxy-5-(2-methoxyphenyl-1-neopentyl-2-oxo-1,2,3,5-tetrahydro-4,1-benzoxazepin-3-acetyl]isonipecotic Acid 74% yield. $^1$H NMR (400 MHz, CDCl$_3$) δ 0.91 (s, 9H); 1.24 (m, 3H); 3.58 (s, 3H); 4.13 (m, 2H); 6.25(s, 1H); 6.45 (br, 1H).

EXAMPLE 9BR

Ethyl Ester of N-[trans-7-Trifluoromethoxy-5-(2-methoxyphenyl)-1-neopentyl-2-oxo-1,2,3,5-tetrahydro-4,1-benzoxazepin-3-acetyl]nipecotic Acid 70% yield. $^1$H NMR (400 MHz, CDCl$_3$) δ 0.91 (s, 9H); 1.24 (m, 3H); 3.58 (s, 3H); 4.12 (m, 2H); 6.25 (m, 1H); 6.46 (b, 1H).

EXAMPLE 9BS

Ethyl Ester of N-[trans-7-Methoxy-5-(2-methoxyphenyl)-1-neopentyl-2-oxo-1,2,3,5-tetrahydro-4,1-benzoxazepin-3-acetyl]isonipecotic Acid 67% yield. $^1$H NMR (400 MHz, CDCl$_3$) δ 0.92 (s, 9H); 1.25 (m, 3H); 3.60 (s, 6H); 4.12 (m, 2H); 6.16 (br, 1H); 6.29 (s, 1H).

EXAMPLE 9BT

Ethyl Ester of N-[trans-7-Methoxy-5-(2-methoxyphenyl)-1-neopentyl-2-oxo-1,2,3,5-tetrahydro-4,1-benzoxazepin-3-acetyl]nipecotic Acid 52% yield. $^1$H NMR (CDCl$_3$) δ 0.93(s, 9H); 1.23 (m, 3H); 3.6 (s, 6H); 4.11 (m, 2H); 6.16 (m, 1H); 6.29 (br, 1H).

EXAMPLE 9BS1

Ethyl Ester of N-[trans-7-Methoxy-5-(2-trifluoromethoxyphenyl-1-neopentyl-2-oxo-1,2,3,5-tetrahydro-4,1-benzoxazepin-3-acetyl]isonipecotic Acid 64% yield. $^1$H NMR (400 MHz, CDCl$_3$) δ 0.89 (s, 9H); 1.24 (m, 3H); 3.6 (s, 3H); 4.12 (m, 2H); 6.04 (m, 1H); 6.28 (s, 1H).

EXAMPLE 9BT1

Ethyl Ester of N-[trans-7-Methoxy-5-(2-trifluoromethoxyphenyl)-1-neopentyl-2-oxo-1,2,3,5-tetrahydro-4,1-benzoxazepin-3-acetyl]nipecotic Acid 92% yield. $^1$H NMR (400 MHz, CDCl$_3$) δ 0.89 (s, 9H); 1.23 (m, 3H); 3.6 (s, 3H); 4.11 (m, 2H); 6.03 (m, 1H); 6.29 (m, 1H).

EXAMPLE 9BU

Ethyl Ester of N-[trans-7-Trifluoromethoxy-5-(2-trifluoromethoxyphenyl)-1-neopentyl-2-oxo-1,2,3,5-tetrahydro-4,1-benzoxazepin-3-acetyl]isonipecotic Acid 22% yield. $^1$H NMR (400 MHz, CDCl$_3$) δ 0.89 (s, 9H); 1.24 (m, 3H); 4.12 (m, 2H); 6.27 (s, 1H); 6.36 (s, 1H).

EXAMPLE 9BV

Ethyl Ester of N-[trans-7-Methyl-9-fluoro-5-(2,3-dimethoxyphenyl)-1-neopentyl-2-oxo-1,2,3,5-tetrahydro-4,1-benzoxazepin-3-acetyl]isonipecotic Acid 62% yield. $^1$H NMR (400 MHz, CDCl$_3$) δ 0.94 (s, 9H); 1.23 (m, 3H); 2.13 (s, 3H); 3.63 (s, 3H); 3.86 (s, 3H); 4.1 (m, 2H); 6.15 (m, 1H); 6.32 (s, 1H).

EXAMPLE 9BW

Ethyl Ester of N-[trans-7-Methyl-9-fluoro-5-(2,3-dimethoxyphenyl)-1-neopentyl-2-oxo-1,2,3,5-tetrahydro-4,1-benzoxazepin-3-acetyl]nipecotic Acid 49% yield. $^1$H NMR (400 MHz, CDCl$_3$) δ 0.94 (s, 9H); 1.24 (m, 3H); 2.14 (s, 3H); 3.63 (s, 3H); 3.87 (s, 3H); 4.1 (m, 2H); 6.16 (m, 1H); 6.32 (b, 1H).

EXAMPLE 9BX

Ethyl Ester of N-[trans-7-Trifluoromethoxy-5-(2-trifluoromethoxyphenyl)-1-neopentyl-2-oxo-1,2,3,5-tetrahydro-4,1-benzoxazepin-3-acetyl]nipecotic Acid 70% yield. $^1$H NMR (400 MHz, CDCl$_3$) δ 0.88 (s, 9H); 1.23 (m, 3H); 4.1 (m, 2H); 6.26 (m, 1H); 6.34 (b, 1H).

EXAMPLE 9BY

Ethyl Ester of N-[trans-7-Chloro-5-(2,3-ethylenedioxyphenyl)-1-(3-t-butyldiphenylsilyloxy-2,2-dimethylpropyl)-2-oxo-1,2,3,5-tetrahydro-4,1-benzoxazepin-3-acetyl]nipecotic Acid 61% yield $^1$H NMR (CDCl$_3$) δ 0.84(s, 3H); 0.97 (s, 3H); 1.04 (s, 9H); 1.25 (m, 3H); 3.9–4.2 (c, 6H); 6.15 (s, 1H); 6.75 (c, 1H).

EXAMPLE 9BZ

Ethyl Ester of N-[trans-7-Chloro-5-(2,3-ethylenedioxyphenyl)-1-(2,2-dimethyl-3-hydroxypropyl)-2-oxo-1,2,3,5-tetrahydro-4,1-benzoxazepin-3-acetyl]nipecotic Acid A solution of HF in water (50%, 0.5 ml) was added to a solution of the ethyl ester of N-[trans-7-chloro-5-(2,3-ethylenedioxyphenyl)-1-(3-t-butyldiphenylsilyloxy-2,2-dimethylpropyl)-2-oxo-1,2,3,5-tetrahydro-4,1-benzoxazepin-3-acetyl)nipecotic acid (85.5 mg, 0.1 mmol) in acetonitrile. After stirring for 18 hr at room temperature, saturated aqueous sodium bicarbonate (10 ml) was added and the resulting mixture was extracted with 3×25 ml dichloromethane. The combined dichloromethane extracts were washed with 20 ml brine, dried over anhydrous sodium sulfate and concentrated in vacuo. The oily residue (49 mg) was chromatographed on a silica gel plate, eluting with 3:7 hexane/ethyl acetate to yield 21 mg (34% yield) of the title compound as a colorless oil.

$^1$H NMR (CDCl$_3$) δ 1.03 (s, 3H); 1.25 (s and m, 6H); 3.9–4.2 (c, 6H); 6.1 (s, 1H); 6.71 (bs, 1H).

EXAMPLE 10

N-[trans-7-Chloro-5-(2,3-ethylenedioxyphenyl)-1-neopentyl-1,2,3,5-tetrahydro-2-oxo-4,1-benzoxazepine-3-acetyl]isonipecotic Acid Potassium carbonate (24 mg, 175 mmol) was added to a solution of the ethyl ester of N-[trans-7-chloro-5-(2,3-ethylenedioxyphenyl)-1-neopentyl-1,2,3,5-tetrahydro-2-oxo-4,1-benzoxazepine-3-acetyl]isonipecotic acid (51 mg, 87 mmol) in methanol (1.8 mL) and water (0.2 mL). The resulting mixture was heated at reflux for 8 hours. After cooling to room temperature, the reaction mixture was concentrated and the resulting residue taken up in water, acidified with an aqueous solution of 1N hydrochloric acid and extracted with ethyl acetate (3×). The combined organics were dried over anhydrous magnesium sulfate, filtered, concentrated under reduced pressure, and purified by flash column chromatography (2% methanol/chloroform) to give 47 mg (94%) of the title compound as a white solid.

MS (APCI): 571 (M+H$^+$). $^1$H NMR (400 MHz, DMSO-d$_6$) δ 7.71 (d, 1H), 7.51 (dd, 1H), 7.08 (m, 1H), 6.93 (m, 2H), 6.49 (d, 1H), 6.03 (s, 1H), 4.25–3.99 (m, 7H), 3.81 (m, 1H), 3.55 (d, 1H), 3.30 (m, 1H), 2.99 (m, 2H), 2.64 (m, 2H), 1.74 (m, 2H), 1.54–1.27 (m, 2H), 0.82 (s, 9H).

The title compounds of Examples 10A–18BZ1 were prepared according to procedures analogous to those described in Example 10.

EXAMPLE 10A (−)-N-[trans-7-Chloro-5-(2,3-ethylenedioxyphenyl)-1-neopentyl-2-oxo-1,2,3,5-tetrahydro-4,1-benzoxazepin-3-acetyl]isonipecotic Acid 91% yield. $^1$H NMR identical to that of Example 10; $[\alpha]_D^{20}$ −204.1°.

EXAMPLE 11

N-[trans-7-Chloro-5-(2,3-dimethoxyphenyl)-1-neopentyl-2-oxo-1,2,3,5-tetrahydro-4,1-benzoxazepin-3-acetyl]isonipecotic Acid 73% yield. $^1$H NMR (CDCl$_3$) δ 0.94 (s, 9H); 1.55–2.03 (c, 4H); 2.57 (c, 1H); 2.7–2.93 (m, 2H); 3.08–3.26 (c, 2H); 3.38 (d, 1H); 3.61 (s, 3H); 3.84–4.0 [c and s (3.89, 3H), total 4H]; 4.32 (m, 1H); 4.5 (m, 2H); 6.27 (s, 1H); 6.6 (s, 1H); 6.98 (m, 1H); 7.14–7.37 (m, 4H).

The title compound of Example 11A was prepared according to procedures analogous to that described for Example 1G and 10A from the appropriate starting material.

EXAMPLE 11A (−)-N-[trans-7-Chloro-5-(2,3-dimethoxyphenyl)-1-neopentyl-2-oxo-1,2,3,5-tetrahydro-4,1-benzoxazepin-3-acetyl]isonipecotic Acid 97% yield. $^1$H NMR identical to that of Example 11. $[\alpha]_D^{20}$ −171°.

EXAMPLE 12

N-[trans-7-Chloro-5-(2,3-dimethoxyphenyl)-1-neopentyl-2-oxo-1,2,3,5-tetrahydro-4,1-benzoxazepin-3-acetyl]nipecotic Acid 95% yield. $^1$H NMR (CDCl$_3$) δ 0.94 (s, 9H); 1.3–2.15 (c, 5H); 2.3–3.45 [c and d (3.38, 1H), total 6H]; 3.62 (s, 3H);

3.8–4.05 [c and s (3.89, 3H), total 4H]; 4.5 (c, 2H); 6.27 (s, 1H); 6.6 (s, 1H); 6.97 (m, 1H); 7.15–7.37 (m, 2H).

EXAMPLE 13

N-[trans-7-Chloro-5-(2,3-dimethoxyphenyl)-1-neopentyl-2-oxo-1,2,3,5-tetrahydro-4,1-benzoxazepin-3-acetyl]-L-proline 61% yield. $^1$H NMR (CDCl$_3$) δ 0.94 (s, 9H); 1.94–2.1 (c, 3H); 2.5 (c, 1H); 2.82 (q, 1H); 3.09 (q, 1H); 3.39 (d, 1H); 3.6–3.7 [c and s (3.61, 3H), total 5H]; 3.89 (s, 3H); 4.45–4.67 (m, 3H); 6.28 (s, 1H); 6.62 (s, 1H); 7.0 (m, 1H); 7.15–7.4 (m, 4H).

EXAMPLE 14

N-[trans-7-Chloro-5-(2,3-dimethoxyphenyl)-1-neopentyl-2-oxo-1,2,3,5-tetrahydro-4,1-benzoxazepin-3-acetyl]-cis-2,4-piperidinedicarboxylic Acid 98% yield. $^1$H NMR (CDCl$_3$) δ 0.94 (s, 9H); 1.5–2.2 (c, 4H); 2.5–3.45 (c, 5H); 3.6–3.95 [c, s (3.61, 3H) and s (3.89, 3H), total 7H]; 4.5 (c, 2H); 6.27 (c, 1H); 6.6 (c, 1H); 7.0 (c, 1H); 7.14–7.4 (c, 4H).

EXAMPLE 15

N-[trans-7-Methyl-5-(2,3-dimethoxyphenyl)-1-neopentyl-2-oxo-1,2,3,5-tetrahydro-4,1-benzoxazepin-3-acetyl]isonipecotic Acid 75% yield. $^1$H NMR (CDCl$_3$) δ 0.94 (s, 9H); 1.55–2.0 (c, 4H); 2.15 (s, 3H); 2.54 (c, 1H); 2.7–2.9 (m, 2H); 3.02–3.24 (m, 2H); 3.4 (d, 1H); 3.6 (s, 3H); 3.85–4.0 (c and s (3.88, 3H), total 4H]; 4.35 (m, 1H); 4.44–4.55 (m, 2H); 6.29 (s, 1H); 6.38 (d, 1H); 6.95 (m, 1H); 7.1–7.3 (m, 4H).

EXAMPLE 16

N-[trans-7-Methyl-5-(2,3-dimethoxyphenyl)-1-neopentyl-2-oxo-1,2,3,5-tetrahydro-4,1-benzoxazepin-3-acetyl]nipecotic Acid 94% yield. $^1$H NMR (CDCl$_3$) δ 0.94 (s, 3H); 1.3–2.2 [c and s (2.16, 3H), total 8H]; 2.3–3.45 [c and d (3.14, 1H), total 6H]; 3.6 (s, 3H); 3.8–4.05 [c and s (3.88, 3H), total 4H]; 4.5 (c, 2H); 6.29 (s, 1H); 6.39 (s, 1H); 6.95 (m, 1H); 7.1–7.3 (m, 4H).

EXAMPLE 17

N-[trans-7-Chloro-5-(2,3-ethylenedioxyphenyl)-1-neopentyl-2-oxo-1,2,3,5-tetrahydro-4,1-benzoxazepin-3-acetylnipecotic Acid 95% yield. $^1$H NMR (CDCl$_3$) δ 0.9 (s, 9H); 1.35–2.16 (c, 5H); 2.35–3.5 [c and s (3.35, 1H); total 6H]; 3.8–4.3 (c, 5H); 4.5 (c, 2H); 6.2 (s, 1H); 6.7 (s, 1H); 6.94 (m, 2H); 7.16 (c, 1H); 7.33 (s, 2H).

EXAMPLE 18

N-[trans-7-Chloro-5-(2,3-ethylenedioxyphenyl)-2-oxo-1,2,3,5-tetrahydro-4,1-benzoxazepin-3-acetyl]-L-proline 85% yield. $^1$H NMR (CDCl$_3$) δ 0.91 (s, 9H); 2.0 (c, 3H); 2.5 (c, 1H); 2.76–2.9 (m, 1H); 2.98–3.16 (m, 1H); 3.37 (m,1H); 3.5–3.6 (c, 2H); 4.05 (c, 2H); 4.2 (c, 2H); 4.5 (c, 2H); 4.6 (c, 1H); 6.22 (m, 1H); 6.7 (m, 1H); 6.9–7.03 (m, 2H); 7.1 (m, 1H); 7.35 (m, 2H).

EXAMPLE 18A

N-[trans-7-Chloro-5-(2,4-dimethoxy-3-methyl-phenyl)-1-neopentyl-2-oxo-1,2,3,5-tetrahydro-4,1-benzoxazepine-3-acetyl]isonipecotic Acid 89% yield. MS (APCI): 587 (M+H$^+$). $^1$H NMR (400 MHz, CDCl$_3$) δ 7.35 (m, 3H), 6.76 (dd, 1H), 6.61 (m, 1H), 6.19 (s, 1H), 4.49 (m, 2H), 4.35 (dd, 1H), 3.89 (m, 1H), 3.87 (d, 3H), 3.49 (s, 3H), 3.38 (d, 1H), 3.08 (m, 2H), 2.77 (m, 2H), 2.54 (m, 1H), 2.14 (s, 3H), 1.92 (m, 2H), 1.70 (m, 2H), 0.94 (s, 9H).

EXAMPLE 18B

N-[trans-7-Methyl-5-(2,4-dimethoxy-3-methyl-phenyl)-1-neopentyl-2-oxo-1,2,3,5-tetrahydro-4,1-benzoxazepine-3-acetyl]isonipecotic Acid quantitative yield. MS (APCI): 567 (M+H$^+$). $^1$H NMR (400 MHz, CDCl$_3$) δ 7.40 (t, 1H), 7.23 (d, 1H), 7.11 (d, 1H), 6.76 (d, 1H), 6.40 (d, 1H), 6.21 (s, 1H), 4.48 (m, 2H), 4.35 (dd, 1H), 3.95 (m, 1H), 3.87 (d, 3H), 3.48 (s, 3H), 3.41 (d, 1H), 3.10 (m, 2H), 2.79 (m, 2H), 2.54 (m, 1H), 2.16 (s, 3H), 2.14 (s, 3H), 1.92 (m, 2H), 1.65 (m, 2H), 0.95 (s, 9H).

EXAMPLE 18C

N-[trans-7-Methyl-5-(2,4-dimethoxy-3-methyl-phenyl)-1-neopentyl-2-oxo-1,2,3,5-tetrahydro-4,1-benzoxazepine-3-acetyl]nipecotic Acid quantitative yield. MS (APCI): 567 (M+H$^+$). $^1$H NMR (400 MHz, CDCl$_3$, diastereomeric mixture) δ 7.41 (m, 1H), 7.12 (d, 1H), 6.77 (d, 1H), 6.40 (br s, 1H), 6.21 (m, 1H), 3.88 (s, 3H), 3.49 (d, 3H), 3.41 (d, 1H), 2.16 (s, 3H), 2.14 (s, 3H), 0.95 (s, 9H).

EXAMPLE 18F

N-[trans-7-Chloro-5-(2,3-ethylenedioxyphenyl)-1-neopentyl-2-oxo-1,2,3,5-tetrahydro-4,1-benzoxazepin-3-acetyl]-L-pipecolinic Acid 96% yield. MS (APCI): 572 (M+H$^+$). $^1$H NMR (CDCl$_3$) δ 0.9, 0.91 (2s, 9H); 4.05 (c, 2H); 4.2 (c, 2H); 5.25, 5.35 (c, 1H); 6.2 (d, 1H); 6.7 (s, 1H).

EXAMPLE 18G

N-[trans-7-Chloro-5-(2,4-dimethoxyphenvl)-1-neopentyl-2-oxo-1,2,3,5-tetrahydro-4,1-benzoxazepin-3-acetyl]isonipecotic Acid 95% yield. MS (APCI): 574 (M+H$^+$). $^1$H NMR (CDCl$_3$) δ 0.92 (s, 9H); 3.6 (s, 3H); 3.86 (s, 3H); 6.2 (s, 1H); 6.45 (s, 1H).

EXAMPLE 18H

N-[trans-7-Chloro-(2,4-dimethoxyrhenyl)-1-neopentyl-2-oxo-1,2,3,5-tetrahydro-4,1-benzoxazepin-3-acetyl]nipecotic Acid 82% yield. MS (APCI): 574 (M+H$^+$). $^1$H NMR (CDCl$_3$) δ 0.91 (s, 9H); 3.6 (s, 3H); 3.86 (s, 3H); 4.48 (c, 2H); 6.2 (br, 1H); 6.45 (d, 1H).

EXAMPLE 18I

N-[trans-7-Chloro-5-(2,4-dimethoxyphenyl)-1-neopentyl-2-oxo-1,2,3,5-tetrahydro-4,1-benzoxazepin-3-acetyl]-L-pipecolinic Acid 92% yield. MS (APCI): 574 (M+H$^+$); $^1$H NMR (CDCl$_3$) δ 0.9 (s, 3H); 3.59 (d, 3H); 3.85 (d, 3H); 5.25, 5.35 (c, 1H); 6.2 (m, 1H); 6.44 (m, 1H).

EXAMPLE 18J

N-[trans-7-Chloro-5-(2,3,4-trimethoxyphenyl)-1-neopentyl-2-oxo-1,2,3,5-tetrahydro-4,1-benzoxazepin-3-acetyl]nipecotic Acid 93% yield. MS (APCI): 604 (M+H$^+$); $^1$H NMR (CDCl$_3$) δ 0.94 (s, 9H); 3.65 (s, 3H); 3.85 (s, 3H); 3.92 (s, 3H); 4.51 (c, 1H); 6.2 (br, 1H); 6.65 (br, 1H).

EXAMPLE 18K

N-[trans-7-Methyl-5-(2,3-ethylenedioxyphenyl)-1-neopentyl-2-oxo-1,2,3,5-tetrahydro-4,1-benzoxazepin-3-acetyl]isonipecotic Acid 86% yield. MS (APCI): 551 (M+H$^+$); $^1$H NMR (CDCl$_3$) δ 0.9 (s, 9H); 2.2 (s, 3H); 4.03 (c, 2H); 4.18 (c 2H); 4.33 (m, 1H), 6.22 (s, 1H); 6.5 (br, 1H).

EXAMPLE 18L

N-[trans-7-Chloro-5-(2,3-ethylenedioxy-4-methoxyphenyl)-1-neopentyl-2-oxo-1,2,3,5-tetrahydro-4,1-benzoxazepin-3-acetyl]isonipecotic Acid 21% yield. MS (APCI): 602 (M+H$^+$); $^1$H NMR (CDCl$_3$) δ 0.9 (s, 9H); 3.93 (s, 3H); 4.04 (c, 2H); 4.26 (c, 2H); 6.15 (s, 1H); 6.62 (d, 1H); 6.69 (s, 1H).

EXAMPLE 18M

N-[trans-7-Chloro-5-(2-ethoxy-4-methoxyphenyl)-1-neopentyl-2-oxo-1,2,3,5-tetrahydro-4,1-benzoxazepin-3-acetyl]isonipecotic Acid 99% yield. MS (APCI): 588 (M+H$^+$); $^1$H NMR (CDCl$_3$) δ 0.92 (s, 9H); 1.16 (t, 3H); 3.84 (s, 3H); 3.9 (q, 2H); 4.33 (m, 1H).

EXAMPLE 18M1

N-[trans-7-Methyl-5-(2,4-dimethoxyphenyl)-1-neopentyl-2-oxo-1,2,3,5-tetrahydro-4,1-benzoxazepin-3-acetyl]isonipecotic Acid 96% yield. MS (APCI): 553 (M+H$^+$); $^1$H NMR (CDCl$_3$) δ 0.9 (s, 9H); 2.2 (s, 3H); 3.59 (s, 3H); 3.84 (s, 3H); 4.33 (m, 1H); 6.23 (s, 1H); 6.45 (s, 1H).

EXAMPLE 18N

N-[trans-7-Chloro-(2,3-dimethoxyphenyl)-1-neopentyl-2-oxo-1,2,3,5-tetrahydro-4,1-benzoxazepin-3-acetyl]-trans-4-hydroxy-L-proline 100% yield. MS (APCI): 576 (M+H$^+$); $^1$H NMR (CDCl$_3$) δ 0.93 (s, 9H); 3.61 (s, 3H); 3.89 (s, 3H); 4.66 (t, 1H); 6.27 (d, 1H); 6.61 (m, 1H).

EXAMPLE 18O

N-[trans-7-Chloro-5-(2,3-dimethoxyphenyl)-1-neopentyl-2-oxo-1,2,3,5-tetrahydro-4,1-benzoxazepin-3-acetyl]-cis-4-hydroxy-D-proline 95% yield. MS (APCI): 576 (M+H$^+$); $^1$H NMR (CDCl$_3$) δ 0.94 (s, 9H); 3.61, 3.62 (2s, 3H); 3.89 (s, 3H); 4.68 (t, 1H); 6.27 (m, 1H); 6.61 (d, 1H).

EXAMPLE 18P

N-[trans-7-Chloro-5-(2,3-ethylenedioxyphenyl)-1-neopentyl-2-oxo-1,2,3,5-tetrahydro-4,1-benzoxazepin-3-acetyl]-trans-4-hydroxy-L-proline 86% yield. MS (APCI): 574 (M+H$^+$); $^1$H NMR (CDCl$_3$) δ 0.89, 0.9 (2s, 9H); 4.05 (c, 2H); 4.19 (c, 2H); 4.65 (t, 1H); 6.2 (d, 1H); 6.71 (m, 1H).

EXAMPLE 18Q

N-[trans-7-Chloro-5-(2,3-ethylenedioxyphenyl)-1-neopentyl-2-oxo-1,2,3,5-tetrahydro-4,1-benzoxazepin-3-acetyl]-cis-4-hydroxy-D-proline 90% yield. MS (APCI): 574 (M+H$^+$); $^1$H NMR (CDCl$_3$) δ 0.9 (s, 9H); 4.05 (c, 2H); 4.19 (c, 2H); 4.65 (t, 1H); 6.2 (d, 1H).

EXAMPLE 18R

N-[trans-7-Chloro-5-(2-chloro-4-methoxyphenyl)-1-neopentyl-2-oxo-1,2,3,5-tetrahydro-4,1-benzoxazepin-3-acetyl]isonipecotic Acid 93% yield. MS (APCI): 578 (M+H$^+$); $^1$H NMR (CDCl$_3$) δ 0.9 (s, 9H), 3.85 (s, 3H); 6.2 (s, 1H); 6.54 (b, 1H).

EXAMPLE 18S

N-[trans-7-Chloro-5-(2-chloro-4-methoxyphenyl)-1-neopentyl-2-oxo-1,2,3,5-tetrahydro-4,1-benzoxazepin-3-acetyl]nipecotic Acid 97% yield. MS (APCI): 579 (M+H$^+$); $^1$H NMR (CDCl$_3$) δ 0.92 (s, 9h); 3.86 (s, 3H); 6.2 (s, 1H); 6.54 (s, 1H).

EXAMPLE 18T

N-[trans-7-Methyl-5-(2,3-ethylenedioxyhenyl)-1-neopentyl-2-oxo-1,2,3,5-tetrahydro-4,1-benzoxazepin-3-acetyl]nipecotic Acid 87% yield. MS (APCI): 551 (M+H$^+$); $^1$H NMR (CDCl$_3$) δ 0.91 (s, 9H); 2.2 (s, 3H); 4.02 (c, 2H); 4.18 (c, 2H); 6.23 (s, 1H); 6.5 (s, 1H).

EXAMPLE 18U

N-[trans-7-Chloro-5-(2,3-ethylenedioxy-4-methoxyphenyl)-1-neopentyl-2-oxo-1,2,3,5-tetrahydro-4,1-benzoxazepin-3-acetyl]nipecotic Acid 91% yield. MS (APCI): 602 (M+H$^+$); $^1$H NMR (CDCl$_3$) δ 0.9 (s, 9H); 3.93 (s, 3H); 4.04 (c, 2H); 4.25 (c, 2H); 6.14 (s, 1H); 6.63 (d, 1H); 6.7 (s, 1H).

EXAMPLE 18V

N-[trans-7-Methyl-5-(2,4-dimethoxyphenyl)-1-neopentyl-2-oxo-1,2,3,5-tetrahydro-4,1-benzoxazepin-3-acetyl]nipecotic Acid 97% yield. MS (APCI): 553 (M+H$^+$); $^1$H NMR (CDCl$_3$) δ 0.92 (s, 9H); 2.18 (s, 3H); 3.59 (s, 3H); 3.86 (s, 3H); 6.23 (s, 1H); 6.45 (br, 2H); 6.61 (d, 1H).

EXAMPLE 18W

N-[trans-7-Chloro-5-(2-methoxyphenyl)-1-neopentyl-2-oxo-1,2,3,5-tetrahydro-4,1-benzoxazepin-3-acetyl]isonipecotic Acid 94% yield. MS (APCI): 544 (M+H$^+$); $^1$H NMR (CDCl$_3$) δ 0.92 (s, 9H); 3.61 (s, 3H); 6.25 (s, 1H); 6.6 (s, 1H); 6.87 (d, 1H).

EXAMPLE 18X

N-[trans-7-Chloro-5-(2-chloro-3,4-dimethoxyphenyl)-1-neopentyl-2-oxo-1,2,3,5-tetrahydro-4,1-benzoxazepin-3-acetyl]isonipecotic Acid 97% yield. MS (APCI): 609 (M+H$^+$); $^1$H NMR (CDCl$_3$) δ 0.92 (s, 9H); 3.85 (s, 3H); 3.93 (s, 3H); 6.19 (s, 1H); 6.53 (s, 1H).

EXAMPLE 18Y

N-[trans-7-Chloro-5-(2-trifluoromethoxyphenyl)-1-neopentyl-2-oxo-1,2,3,5-tetrahydro-4,1-benzoxazepin-3-acetyl]isonipecotic Acid 95% yield. MS (APCI): 598 (M+H$^+$); $^1$H NMR (CDCl$_3$) δ 0.89 (s, 9H); 4.32 (c, 1H); 6.25 (s, 1H); 6.49 (s, 1H).

EXAMPLE 18Z

N-[trans-7-Chloro-5-(2-methoxyphenyl)-1-neopentyl-2-oxo-1,2,3,5-tetrahydro-4,1-benzoxazepin-3-acetyl]nipecotic Acid 90% yield. MS (APCI): 544 (M+H$^+$); $^1$H NMR (CDCl$_3$ δ 0.9 (s, 9H); 3.62 (s, 3H); 4.5 (c, 2H); 6.26 (s, 1H); 6.6 (s, H).

EXAMPLE 18AA

N-[trans-7-Chloro-5-(2-chloro-3,4-dimethoxyphenyl)-1-neopentyl-2-oxo-1,2,3,5-tetrahydro-4,1-benzoxazepin-3-acetyl]nipecotic Acid 74% yield. MS (APCI): 609 (M+H$^+$); $^1$H NMR (CDCl$_3$) δ 0.93 (s, 9H); 3.86 (s, 3H), 3.94 (s, 3H); 6.2 (s, 1H); 6.55 (s, 1H).

EXAMPLE 18AB

N-[trans-7-Chloro-5-(2-trifluoromethoxyphenyl)-1-neopentyl-2-oxo-1,2,3,5-tetrahydro-4,1-benzoxazepin-3-acetyl]nipecotic Acid 75% yield. MS (APCI): 598 (M+H$^+$); $^1$H NMR (CDCl$_3$) δ 0.9 (s, 9H); 4.5 (d) and 4.57 (m) (total 2H); 6.26 (s, 1H); 6.5 (s, 1H).

EXAMPLE 18AC

N-[trans-7-Chloro-5-(2,3-dimethoxyphenyl)-1-neopentyl-2-oxo-1,2,3,5-tetrahydro-4,1-benzoxazepin-3-acetyl]azetidine-3-carboxylic Acid 96% yield. MS (APCI): 546 (M+H$^+$); $^1$H NMR (CDCl$_3$) δ 0.94 (s, 9H); 3.6 (s, 3H); 3.9 (s, 3H); 6.27 (d, 1H); 6.6 (s, 1H).

EXAMPLE 18AD

N-[trans-7-Chloro-5-(2,3-ethylenedioxyphenyl)-1-neopentyl-2-oxo-1,2,3,5-tetrahydro-4,1-benzoxazepin-3-acetyl]azetidine-3-carboxylic Acid 91% yield. MS (APCI): 544 (M+H$^+$); $^1$H NMR (CDCl$_3$) δ 0.92 (s, 9H); 4.03 (c, 2H), 4.2 (c, 2H); 6.2 (d, 1H); 6.7 (b, 1H).

EXAMPLE 18AE

N-[trans-7-Methylthio-5-(2,3-dimethoxyphenyl)-1-neopentyl-2-oxo-1,2,3,5-tetrahydro-4,1-benzoxazepin-3-acetyl]isonipecotic Acid 70% yield. MS (APCI): 585 (M+H$^+$); $^1$H NMR (CDCl$_3$) δ 0.94 (s, 9H); 2.28 (s, 3H); 3.6 (s, 3H); 3.88 (s, 3H); 4.34 (c, 1H); 6.3 (s, 1H); 6.51 (m, 1H).

EXAMPLE 18AF

N-[trans-7-Methylthio-5-(2,3-dimethoxyphenyl)-1-neopentyl-2-oxo-1,2,3,5-tetrahydro-4,1-benzoxazepin-3-acetyl]nipecotic Acid 87% yield. MS (APCI): 585 (M+H$^+$); $^1$H NMR (CDCl$_3$) δ 0.94 (s, 9H); 2.28 (s, 3H); 3.6 (s, 3H); 3.88 (s, 3H); 6.3 (s, 1H); 6.51 (s, 1H).

EXAMPLE 18AG

N-[trans-7-Methyl-5-(2,3-methylenedioxyphenyl)-1-neopentyl-2-oxo-1,2,3,5-tetrahydro-4,1-benzoxazepin-3-acetyl]isonipecotic Acid 89% yield. MS (APCI): 537 (M+H$^+$); $^1$H NMR (CDCl$_3$) δ 0.9 (s, 3H); 2.22 (s, 3H); 4.33 (m, 1H); 5.87 (d, 2H); 6.16 (s, 1H).

EXAMPLE 18AG1

N-[trans-7-Methyl-5-(2,3-methylenedioxyphenyl)-1-neopentyl-2-oxo-1,2,3,5-tetrahydro-4,1-benzoxazepin-3-acetyl]nipecotic Acid 84% yield. MS (APCI): 536; $^1$H NMR (CDCl$_3$) δ 0.89 (s, 3H); 2.22 (s, 3H); 5.87 (d, 2H); 6.15 (s, 1H); 6.58 (s, 1H).

EXAMPLE 18AH

N-[trans-7-Methylthio-5-(2,3-ethylenedioxyphenyl)-1-neopentyl-2-oxo-1,2,3,5-tetrahydro-4,1-benzoxazepin-3-acetyl]isonipecotic Acid 81% yield. MS (APCI): 583 (M+H$^+$); $^1$H NMR (CDCl$_3$) δ 0.91 (s, 9H); 2.31 (s, 3H); 4.03 (c, 2H); 4.19 (c, 2H); 4.34 (c, 1H); 6.23 (m, 1H); 6.59 (m, 1H).

EXAMPLE 18AI

N-[trans-7-Methylthio-5-(2,3-ethylenedioxyphenyl)-1-neopentyl-2-oxo-1,2,3,5-tetrahydro-4,1-benzoxazepin-3-acetyl]nipecotic Acid 94% yield. MS (APCI): 583 (M+H$^+$); $^1$H NMR (CDCl$_3$) δ 0.91 (s, 9H); 2.31 (s, 3H); 4.03 (c, 2H); 4.18 (c, 2H); 6.23 (s, 1H); 6.59 (s, 1H).

EXAMPLE 18AJ

N-[trans-7-Chloro-5-(2,3-dimethoxyphenyl)-1-cyclopropylmethyl-2-oxo-1,2,3,5-tetrahydro-4,1-benzoxazepin-3-acetyl]isonipecotic Acid 73% yield. MS (APCI): 558 (M+H$^+$); $^1$H NMR (CDCl$_3$) δ 0.18 (c, 1H); 0.35–0.55 (c, 3H); 1.1 (c, 1H); 3.54 (s, 3H); 3.88 (s, 3H); 6.24 (s, 2H); 6.64 (s, 1H).

EXAMPLE 18AK

N-[trans-7-Chloro-5-(2,3-dimethoxyphenyl)-1-cyclopropylmethyl-2-oxo-1,2,3,5-tetrahydro-4,1-benzoxazepin-3-acetyl]nipecotic Acid 72% yield. $^1$H NMR (CDCl$_3$) δ 0.18 (c, 1H); 0.36–0.56 (c, 3H); 1.1 (c, 1H); 3.53 (s, 3H); 3.88 (s, 3H); 6.24 (s, 1H); 6.64 (m, 1H).

EXAMPLE 18AL

N-[trans-7-Chloro-5-(3,4-ethylenedioxyphenyl)-1-neopentyl-2-oxo-1,2,3,5-tetrahydro-4,1-benzoxazepin-3-acetyl]isonipecotic Acid 64% yield. MS (APCI): 572 (M+H$^+$); $^1$H NMR (CDCl$_3$) δ 0.89 (s, 9H); 4.3 (s, 4H); 5.88 (s, 1H); 6.7 (m, 1H).

EXAMPLE 18AM

N-[trans-7-Chloro-5-(3,4-ethylenedioxyphenyl)-1-neopentyl-2-oxo-1,2,3,5-tetrahydro-4,1-benzoxazepin-3-acetyl]nipecotic Acid 94% yield. MS (APCI): 572 (M+H$^+$); $^1$H NMR (CDCl$_3$ δ 0.89 (s, 9H); 3.94 (c, 1H); 4.3 (s, 4H); 5.88 (s, 1H).

EXAMPLE 18AN

N-[trans-7,8-Ethylenedioxy-5-(2,3-dimethoxyphenyl)-1-neopentyl-2-oxo-1,2,3,5-tetrahydro-4,1-benzoxazepin-3-acetyl]isonipecotic Acid 72% yield. MS (APCI): 597 (M+H$^+$); $^1$H NMR (CDCl$_3$) δ 0.96 (s, 9H); 3.63 (s, 3H); 3.87 (s, 3H); 4.16 (c, 2H); 4.2 (c, 2H); 6.17 (d, 1H); 6.24 (s, 1H).

EXAMPLE 18AO

N-[trans-7,8-Ethylenedioxy-5-(2,3-dimethoxyphenyl)-1-neopentyl-2-oxo-1,2,3,5-tetrahydro-4,1-benzoxazepin-3-acetyl]nipecotic Acid 98% yield. MS (APCI): 597 (M+H$^+$); $^1$H NMR (CDCl$_3$) δ 0.96 (s, 9H); 3.63 (s, 3H); 3.86 (s, 3H); 4.16 (c, 2H); 4.2 (c, 2H); 6.11 (s, 1H); 6.24 (s, 1H).

EXAMPLE 18AP

N-[trans-7-Methyl-5-(2-methoxyphenyl)-1-neopentyl-2-oxo-1,2,3,5-tetrahydro-4,1-benzoxazepin-3-acetyl]isonipecotic Acid 96% yield. MS (APCI): 523 (M+H$^+$); $^1$H NMR (CDCl$_3$) δ 0.93 (s, 9H); 2.16 (s, 3H); 3.62 (s, 3H); 4.35 (m, 1H); 6.3 (s 1H); 6.41 (s, 1H).

EXAMPLE 18AQ

N-[trans-7-Methylthio-5-(2-trifluoromethoxyphenyl)-1-neopentyl-2-oxo-1,2,3,5-tetrahydro-4,1-benzoxazepin-3-acetyl]isonipecotic Acid 89% yield. MS (APCI): 609 (M+H$^+$); $^1$H NMR (CDCl$_3$) δ 0.9 (s, 9H); 2.26 (s, 3H); 4.34 (c, 1H); 6.28 (s, 1H); 6.38 (s, 1H).

EXAMPLE 18AR

N-[trans-7-Methylthio-5-(2-methoxyphenyl)-1-neopentyl-2-oxo-1,2,3,5-tetrahydro-4,1-benzoxazepin-3-acetyl]isonipecotic Acid 92% yield. MS (APCI): 555 (M+H$^+$); $^1$H NMR (CDCl$_3$) δ 0.93 (s, 9H); 2.28 (s, 3H); 3.61 (s, 3H); 4.35 (c, 1H); 6.29 (s, 1H); 6.5 (s, 1H).

EXAMPLE 18AS

N-[trans-7-Methyl-5-(2-trifluoromethoxyphenyl)-1-neopentyl-2-oxo-1,2,3,5-tetrahydro-4,1-benzoxazepin-3-acetyl]isonipecotic Acid 60% yield. MS (APCI): 577 (M+H$^+$); $^1$H NMR (CDCl$_3$) δ 0.9 (s, 9H); 2.16 (s, 3H); 4.36 (c, 1H); 6.29 (s, 1H).

EXAMPLE 18AT

N-[trans-7-Methyl-5-(2-methoxyphenyl)-1-neopentyl-2-oxo-1,2,3,5-tetrahydro-4,1-benzoxazepin-3-acetyl]nipecotic Acid 71% yield. MS (APCI): 523 (M+H$^+$); $^1$H NMR (CDCl$_3$) δ 0.93 (s, 9H); 2.17 (s, 3H); 3.62 (s, 3H); 6.3 (s, 1H); 6.41 (s, 1H).

EXAMPLE 18AU

N-[trans-7-Methylthio-5-(2-trifluoromethoxyphenyl)-1-neopentyl-2-oxo-1,2,3,5-tetrahydro-4,1-benzoxazepin-3-acetyl]nipecotic Acid 85% yield. MS (APCI): 609 (M+H$^+$); $^1$H NMR (CDCl$_3$) δ 0.9 (s, 9H); 2.27 (s, 3H); 4.59 (c, 1H); 6.28 (s, 1H); 6.38 (s, 1H).

EXAMPLE 18AV

N-[trans-7-Methylthio-5-(2-methoxyphenyl)-1-neopentyl-2-oxo-1,2,3,5-tetrahydro-4,1-benzoxazepin-3-acetyl]nipecotic Acid 74% yield. MS (APCI): 558 (M+H$^+$); $^1$H NMR (CDCl$_3$) δ 0.93 (s, 9H); 2.28 (s, 3H); 3.61 (s, 3H); 6.29 (s, 1H); 6.51 (s, 1H).

EXAMPLE 18AV1

N-[trans-7-Methyl-5-(2-trifluoromethoxyphenyl)-1-neopentyl-2-oxo-1,2,3,5-tetrahydro-4,1-benzoxazepin-3-acetyl]nipecotic Acid 13% yield. $^1$H NMR (CDCl$_3$) δ 0.9 (s, 9H); 2.17 (s, 3H); 6.29 (s, 1H).

EXAMPLE 18AW

N-[trans-7-Methylthio-5-(2,3-methylenedioxyphenyl)-1-neopentyl-2-oxo-1,2,3,5-tetrahydro-4,1-benzoxazepin-3-acetyl]isonipecotic Acid 93% yield. MS (APCI): 569 (M+H$^+$); $^1$H NMR (CDCl$_3$) δ 0.9 (s, 9H); 2.33 (s, 3H); 4.32 (c, 1H); 5.87 (d, 2H); 6.14 (s, 1H); 6.67 (s, 1H).

EXAMPLE 18AX

N-[trans-7-Methylthio-5-(2,3-methylenedioxyphenyl)-1-neopentyl-2-oxo-1,2,3,5-tetrahydro-4,1-benzoxazepin-3-acetyl]nipecotic Acid 97% yield. MS (APCI): 569 (M+H$^+$); $^1$H NMR (CDCl$_3$) δ 0.89 (s, 9H); 2.33 (s, 3H); 4.54 (c, 1H); 5.88 (d, 2H); 6.14 (s, 1H); 6.68 (s, 1H).

EXAMPLE 18AY

N-[trans-7-Chloro-5-(3,4-methylenedioxyphenyl)-1-neopentyl-2-oxo-1,2,3,5-tetrahydro-4,1-benzoxazepin-3-acetyl]isonipecotic Acid 89% yield. MS (APCI): 558 (M+H$^+$); $^1$H NMR (CDCl$_3$) δ 0.9 (s, 9H); 4.31 (c, 1H); 5.91 (s, 1H); 6.03 (d, 2H).

EXAMPLE 18AZ

N-[trans-7-Chloro-5-(3,4-methylenedioxyphenyl)-1-neopentyl-2-oxo-1,2,3,5-tetrahydro-4,1-benzoxazepin-3-acetyl]nipecotic Acid 88% yield. MS (APCI): 558 (M+H$^+$); $^1$H NMR (CDCl$_3$) δ 0.9 (s, 9H); 5.91 (s, 1H); 6.03 (d, 2H); 6.69 (b, 1H).

EXAMPLE 18BA

N-[trans-7-Chloro-5-(2,3-methylenedioxyphenyl)-1-neopentyl-2-oxo-1,2,3,5-tetrahydro-4,1-benzoxazepin-3-acetyl]isonipecotic Acid 96% yield. MS (APCI): 558 (M+H$^+$); $^1$H NMR (400 MHz, CDCl$_3$) δ 0.89 (s, 9H); 5.86 (d, 2H); 6.1 (s, 1H);.

EXAMPLE 18BB

N-[trans-7-Chloro-5-(2,3-methylenedioxyphenyl)-1-neopentyl-2-oxo-1,2,3,5-tetrahydro-4,1-benzoxazepin-3-acetyl]-L-proline 88% yield. MS (APCI): 544 (M+H$^+$); $^1$H NMR (400 MHz, CDCl$_3$) δ 0.88 (s, 9H); 5.87 (d, 2H); 6.12 (d, 2H).

EXAMPLE 18BC

N-[trans-7-Chloro-5-(2,3-methylenedioxyphenyl)-1-neopentyl-2-oxo-1,2,3,5-tetrahydro-4,1-benzoxazepin-3-acetyl]nipecotic Acid 100% yield. MS (APCI): 558 (M+H$^+$); $^1$H NMR (400 MHz, CDCl$_3$) δ 0.88 (s, 9H); 5.87 (d, 2H); 6.11 (s, 1H).

EXAMPLE 18BD

N-[trans-7-Methoxy-5-(2,3-dimethoxyphenyl))-1-neopentyl-2-oxo-1,2,3,5-tetrahydro-4,1-benzoxazepin-3-acetyl]nipecotic Acid 89% yield. MS (APCI): 569 (M+H$^+$); $^1$H NMR (CDCl$_3$) δ 0.94 (s, 9H); 3.61 (s, 6H); 3.86 (s, 3H); 6.16 (m, 1H); 6.3 (b, 1H).

EXAMPLE 18BE

N-[trans-7-Methoxy-(2,3-dimethoxyphenyl)-1-neopentyl-2-oxo-1,2,3,5-tetrahydro-4,1-benzoxazepin-3-acetyl]isonipecotic Acid 94% yield. MS (APCI): 569 (M+H$^+$); $^1$H NMR (400 MHz, CDCl$_3$) δ 0.94 (s, 9H); 3.62 (s, 6H); 3.86 (s, 3H); 6.15 (m, 1H); 6.29 (s, 1H).

EXAMPLE 18BF

N-[trans-7-Trifluoromethoxy-5-(2,3-dimethoxyphenyl)-1-neopentyl-2-oxo-1,2,3,5-tetrahydro-4,1-benzoxazepin-3-acetyl]nipecotic Acid 99% yield. MS (APCI): 621 (M+H$^+$); $^1$H NMR (CDCl$_3$) δ 0.94 (s, 9H); 3.58 (s, 3H); 3.88 (s, 3H); 6.3 (s, 1H); 6.48 (s, 1H).

EXAMPLE 18BG

N-[trans-7-Trifluoromethoxy-5-(2,3-dimethoxyphenyl)-1-neopentyl-2-oxo-1,2,3,5-tetrahydro-4,1-benzoxazepin-3-acetyl]isonipecotic Acid 96% yield. MS (APCI): 623 (M+H$^+$); $^1$H NMR (400 MHz, CDCl$_3$) δ 0.93 (s, 9H); 3.57 (s, 3H); 3.87 (s, 3H); 6.28 (s, 1H); 6.47 (b, 1H).

EXAMPLE 18BH

N-[trans-7-Methoxy-5-(2,3-ethylenedioxyphenyl)-1-neopentyl-2-oxo-1,2,3,5-tetrahydro-4,1-benzoxazepin-3-acetyl]nipecotic Acid 93% yield. MS (APCI): 567 (M+H$^+$); $^1$H NMR (400 MHz, CDCl$_3$) δ 0.9 (s, 9H); 3.64 (s, 3H); 4 (c, 2H); 4.2 (c, 2H); 6.24 (m, 1H);

EXAMPLE 18BH1

N-[trans-7-Methoxy-5-(2,3-ethylenedioxyphenyl)-1-neopentyl-2-oxo-1,2,3,5-tetrahydro-4,1-benzoxazepin-3-acetyl]isonipecotic Acid 89% yield. MS (APCI): 567 (M+H$^+$); $^1$H NMR (400 MHz, CDCl$_3$) δ 0.9 (s, 9H); 3.64 (s, 3H); 4 (c, 2H); 4.2 (c, 2H); 6.24 (m, 1H).

EXAMPLE 18BI

N-[trans-7-Trifluoromethoxy-5-(2,3-ethylenedioxyphenyl)-1-neopentyl-2-oxo-1,2,3,5-tetrahydro-4,1-benzoxazepin-3-acetyl]isonipecotic Acid 89% yield. MS (APCI): 621 (M+H$^+$); $^1$H NMR (CDCl$_3$) δ 0.9 (s, 9H); 4 (c, 2H); 4.2 (c, 2H); 6.2 (s, 1H); 6.55 (b, 1H).

EXAMPLE 18BJ

N-[trans-7-Trifluoromethoxy-5-(2,3-ethylenedioxyphenyl)-1-neopentyl-2-oxo-1,2,3,5-tetrahydro-4,1-benzoxazepin-3-acetyl]nipecotic Acid 84% yield. MS (APCI): 621 (M+H$^+$); $^1$H NMR (CDCl$_3$) δ 0.9 (s, 9H); 4 (c, 2H); 4.2 (c, 2H); 6.19 (s, 1H); 6.55 (s, 1H).

EXAMPLE 18BK

N-[trans-7-Trifluoromethoxy-5-(2,3-methylenedioxyphenyl)-1-neopentyl-2-oxo-1,2,3,5-tetrahydro-4,1-benzoxazepin-3-acetyl]isonipecotic Acid 68% yield. MS (APCI): 607 (M+H$^+$); $^1$H NMR (CDCl$_3$) δ 0.9 (s, 9H); 5.87 (m, 2H); 6.14 (s, 1H).

EXAMPLE 18BL

N-[trans-7-Trifluoromethoxy-5-(2,3-methylenedioxyphenyl)-1-neopentyl-2-oxo-1,2,3,5-tetrahydro-4,1-benzoxazepin-3-acetyl]nipecotic Acid 98% yield. MS (APCI): 607 (M+H$^+$); $^1$H NMR (CDCl$_3$) δ 0.9 (s, 9H); 5.88 (s, 2H); 6.14 (bs, 1H).

EXAMPLE 18BM

N-[trans-7-Methoxy-5-(2,3-methylenedioxyphenyl)-1-neopentyl-2-oxo-1,2,3,5-tetrahydro-4,1-benzoxazepin-3-acetyl]isonipecotic Acid 95% yield. MS (APCI): 523 (M+H$^+$); $^1$H NMR (CDCl$_3$) δ 0.89 (s, 9H); 3.66 (s, 3H); 5.87 (m, 2H); 6.15 (s, 1H).

EXAMPLE 18BN

N-[trans-7-Methoxy-5-(2,3-methylenedioxyphenyl)-1-neopentyl-2-oxo-1,2,3,5-tetrahydro-4,1-benzoxazepin-3-acetyl]nipecotic Acid 96% yield. MS (APCI): 553 (M+H$^+$); $^1$H NMR (CDCl$_3$) δ 0.93 (s, 9H); 3.84 (s, 3H); 5.88 (m, 2H); 6.0 (s, 1H).

EXAMPLE 18BO

N-[trans-7-trifluoromethyl-5-(2,3-dimethoxyphenyl)-1-neopentyl-2-oxo-1,2,3,5-tetrahydro-4,1-benzoxazepin-3-acetyl]isonipecotic Acid 88% yield. MS (APCI): 607 (M+H$^+$); $^1$H NMR (CDCl$_3$) δ 0.94 (s, 9H); 3.57 (s, 3H); 3.88 (s, 3H); 6.32 (s, 1H); 6.9 (b, 1H).

EXAMPLE 18BP

N-[trans-7-Trifluoromethyl-5-(2,3-dimethoxyphenyl)-1-neopentyl-2-oxo-1,2,3,5-tetrahydro-4,1-benzoxazepin-3-acetyl]nipecotic Acid 74% yield. MS (APCI): 607 (M+H$^+$); $^1$H NMR (CDCl$_3$) δ 0.94 (s, 9H); 3.57 (s, 3H); 3.89 (s, 3H); 6.32 (s, 1H); 6.91 (b, 1H).

EXAMPLE 18BQ

N-[trans-7-Trifluoromethoxy-5-(2-methoxyphenyl)-1-neopentyl-2-oxo-1,2,3,5-tetrahydro-4,1-benzoxazepin-3-acetyl]isonipecotic Acid 78% yield. MS (APCI): 593 (M+H$^+$); $^1$H NMR (CDCl$_3$) δ 0.92 (s, 9H); 3.59 (s, 3H); 6.26 (s, 1H); 6.47 (b, 1H).

EXAMPLE 18BR

N-[trans-7-Trifluoromethoxy-5-(2-methoxyphenyl)-1-neopentyl-2-oxo-1,2,3,5-tetrahydro-4,1-benzoxazepin-3-acetyl]nipecotic Acid 96% yield. MS (APCI): 593 (M+H⁺); ¹H NMR (CDCl₃) δ 0.92 (s, 9H); 3.59 (s, 3H); 6.26 (s, 1H); 6.47 (s, 1H).

EXAMPLE 18BS

N-[trans-7-Methoxy-5-(2-methoxyphenyl)-1-neopentyl-2-oxo-1,2,3,5-tetrahydro-4,1-benzoxazepin-3-acetyl]isonipecotic Acid 75% yield. MS (APCI): 539 (M+H⁺); ¹H NMR (CDCl₃) δ 0.93 (s, 9H); 3.61 (s, 6H); 6.17 (b, 1H); 6.3 (s, 1H).

EXAMPLE 18BS1

N-[trans-7-Methoxy-5-(2-trifluoromethoxyphenyl)-1-neopentyl-2-oxo-1,2,3,5-tetrahydro-4,1-benzoxazepin-3-acetyl]isonipecotic Acid 96% yield. MS (APCI): 593 (M+H⁺); ¹H NMR (400 MHz, CDCl₃) δ 0.88 (s, 9H); 3.59 (s, 3H); 6.02 (m, 1H); 6.27 (s, 1H).

EXAMPLE 18BT

N-[trans-7-Methoxy-5-(2-methoxyphenyl)-1-neopentyl-2-oxo-1,2,3,5-tetrahydro-4,1-benzoxazepin-3-acetyl]nipecotic Acid 52% yield. MS (APCI): 539 (M+H⁺); ¹H NMR (400 MHz, CDCl₃) δ 0.92 (s, 9H); 3.61 (s, 6H); 6.16 (m, 1H); 6.29 (s, 1H).

EXAMPLE 18BT1

N-[trans-7-Methoxy-5-(2-trifluoromethoxyphenyl)-1-neopentyl-2-oxo-1,2,3,5-tetrahydro-4,1-benzoxazepin-3-acetyl]nipecotic Acid 58% yield. MS (APCI): 593 (M+H)⁺¹H NMR (400 MHz, CDCl₃) δ 0.89 (s, 9H); 3.6 (s, 3H); 6.03 (m, 1H); 6.27 (b, 1H).

EXAMPLE 18BU

N-[trans-7-Trifluoromethoxy-5-(2-trifluoromethoxyphenyl)-1-neopentyl-2-oxo-1,2,3,5-tetrahydro-4,1-benzoxazepin-3-acetyl]isonipecotic Acid 100% yield. MS (APCI): 647 (M+H⁺); ¹H NMR (CDCl₃) δ 0.89 (s, 9H); 6.27 (s, 1H); 6.37 (s, 1H).

EXAMPLE 18BV

N-[trans-7-Methyl-9-fluoro-5-(2,3-dimethoxyphenyl)-1-neopentyl-2-oxo-1,2,3,5-tetrahydro-4,1-benzoxazepin-3-acetyl]isonipecotic Acid 94% yield. MS (APCI): 571 (M+H⁺); ¹H NMR (CDCl₃) δ 0.94 (s, 9H); 2.14 (s, 3H); 3.63 (s, 3H); 3.87 (s, 3H); 6.16 (m, 1H); 6.26 (s, 1H).

EXAMPLE 18BW

N-[trans-7-Methyl-9-fluoro-5-(2,3-dimethoxyphenyl)-1-neopentyl-2-oxo-1,2,3,5-tetrahydro-4,1-benzoxazepin-3-acetyl]nipecotic Acid 53% yield. MS (APCI): 571 (M+H⁺); ¹H NMR (400 MHz, CDCl₃) δ 0.94 (s, 9H); 2.14 (s, 3H); 3.63 (s, 3H); 3.87 (s, 3H); 6.16 (m, 1H); 6.32 (b, 1H).

EXAMPLE 18BX

N-[trans-7-Trifluoromethoxy-5-(2-trifluoromethoxyphenyl)-1-neopentyl-2-oxo-1,2,3,5-tetrahydro-4,1-benzoxazepin-3-acetyl]nipecotic Acid 98% yield. MS (APCI): 647 (M+H⁺); ¹H NMR (CDCl₃) δ 0.88 (s, 9H); 6.26 (m, 1H); 6.36 (s, 1H).

EXAMPLE 18BZ1

N-[trans-7-Chloro-5-(2,3-ethylenedioxyphenyl)-1-(2,2-dimethyl-3-hydroxypropyl)-2-oxo-1,2,3,5-tetrahydro-4,1-benzoxazepin-3-acetyl]nipecotic Acid 72% yield. MS (APCI): 588 (M+H⁺); ¹H NMR (CDCl₃) δ 1.03 (s, 3H); 1.25 (s, 23H); 4.04 (c, 2H); 4.2 (c, 2H); 6.09 (s, 1H); 6.71 (s, 1H).

EXAMPLE 19

Ethyl Ester of N-[trans-7-Chloro-5-(2,3-ethylenedioxyphenyl)-1-neopentyl-1,2,3,5-tetrahydro-4,1-benzoxazepine-3-acetyl]isonipecotic Acid

EXAMPLE 19A

2-[trans-7-Chloro-5-(2,3-ethylenedioxyphenyl)-1-neopentyl-1,2,3,5-tetrahydro-4,1-benzoxazepin-3-yl]-ethanol Borane-methyl sulfide complex (2.0M in tetrahydrofuran; 5.9 mL, 11.8 mmol) was added to a solution of the ethyl ester of trans-7-chloro-5-(2,3-ethylenedioxyphenyl)-1-neopentyl-1,2,3,5-tetrahydro-2-oxo-4,1-benzoxazepine-3-acetic acid (1.44 g, 2.95 mmol; Example 1D) in tetrahydrofuran (4.4 mL) under a nitrogen atmosphere. The reaction was stirred at ambient temperature for 18 hours and then cooled to 0° C. and quenched by slow addition of methanol. Once gas evolution ceased, an additional amount of methanol was added and the resulting mixture stirred 1 hour. The reaction mixture was then concentrated and the resulting residue taken up in water and extracted with ethyl acetate (3×). The combined organics were washed with saturated aqueous sodium chloride, dried over anhydrous sodium sulfate, filtered, concentrated under reduced pressure, and purified by flash column chromatography (3:1 hexanes/ethyl acetae) to give 835 mg (66%) of the title compound as a white solid.

MS (APCI): 432 (M+H⁺). ¹H NMR (400 MHz, CDCl₃) δ 7.14 (dd, 1H), 7.02 (m, 2H), 6.89 (m, 2H), 6.57 (d, 1H), 6.51 (s, 1H), 4.22–4.07 (m, 4H), 3.94 (m, 1H), 3.78–3.64 (m, 4H), 3.02 (dd, 1H), 2.59 (d, 2H), 1.77–1.63 (m, 2H), 0.92 (s, 9H).

EXAMPLE 19B

[trans-7-Chloro-5-(2,3-ethylenedioxyphenyl)-1-neopentyl-1,2,3,5-tetrahydro-4,1-benzoxazepin-3-yl]-acetaldehyde Dess-Martin periodinane (979 mg, 2.31 mmol) was added to a solution of 2-[trans-7-chloro-5-(2,3-ethylenedioxyphenyl)-1-neopentyl-1,2,3,5-tetrahydro-4,1-benzoxazepin-3-yl]-ethanol (830 mg, 1.92 mmol), pyridine (980 mL) and methylene chloride (18 mL) at 0° C. The mixture was warmed to ambient temperature and stirred 40 minutes before adding more Dess-Martin periodinane (800 mg, 1.89 mmol). After an additional 15 minutes, the reaction was quenched by addition of 5:1 saturated aqueous sodium bicarbonate/saturated aqueous sodium sulfite, stirred 5 minutes, and extracted with ether (2×). The combined organics were washed with saturated aqueous sodium chloride, dried over anhydrous sodium sulfate, filtered, concentrated under reduced pressure, and purified by flash column chromatography (9:1 hexanes/ethyl acetate) to give 562 mg (68%) of the title compound as a white foam.

MS (APCI): 430 (M+H$^+$). $^1$H NMR (400 MHz, CDCl$_3$) δ 9.78 (dd, 1H), 7.16 (m, 1H), 7.06 (m, 2H), 6.90 (m, 2H), 6.54 (m, 2H), 4.28–4.04 (m, 5H), 3.69 (m, 2H), 3.07 (dd, 1H), 2.64 (ddd, 1H), 2.56 (d, 1H), 2.43 (ddd, 1H), 0.92 (s, 9H).

EXAMPLE 19C trans-7-Chloro-5-(2,3-ethylenedioxyphenyl)-1-neopentyl-1,2,3,5-tetrahydro-4,1-benzoxazepine-3-acetic Acid Aqueous hydrogen peroxide (30% by weight; 69 mL, 605 mmol) was added to a solution of [trans-7-chloro-5-(2,3-ethylenedioxyphenyl)-1-neopentyl-1,2,3,5-tetrahydro-4,1-benzoxazepin-3-yl]-acetaldehyde (250 mg, 582 mmol), aqueous sodium phosphate monobasic (63 mg in 1 mL water) and acetonitrile (1.25 mL). Sodium chlorite (1M in water; 640 mL, 640 mmol) was then added dropwise. After 45 minutes, the reaction mixture was quenched with saturated aqueous sodium sulfite, concentrated, taken up in water and extracted with ethyl acetate (3×). The combined organics were washed with saturated aqueous sodium chloride, dried over anhydrous sodium sulfate, filtered, concentrated under reduced pressure, and purified by flash column chromatography (2% methanol/chloroform) to give 170 mg (66%) of the title compound as a white foam.

MS (APCI): 446 (M+H$^+$). $^1$H NMR (400 MHz, CDCl$_3$) δ 7.16–7.87 (m, 5H), 6.58 (d, 1H), 6.54 (s, 1H), 4.22–4.06 (m, 5H), 3.65 (m, 2H), 3.25 (dd, 1H), 3.11 (d, 1H), 2.9–2.5 (m, 2H), 0.92 (s, 9H).

EXAMPLE 19D

Ethyl Ester of N-[trans-7-Chloro-5-(2,3-ethylenedioxyphenyl)-1-neopentyl-1,2,3,5-tetrahydro-4,1-benzoxazepine-3-acetyl]isonipecotic Acid 1-(3-Dimethylaminopropyl)-3-ethylcarbodiimide hydrochloride (60 mg, 310 mmol) and ethyl isonipecotate (29 mg, 189 mmol, 29 mL) were added sequentially to a solution of trans-7-Chloro-5-(2,3-ethylenedioxyphenyl)-1-neopentyl-1,2,3,5-tetrahydro-4,1-benzoxazepine-3-acetic acid (70 mg, 157 mmol) and methylene chloride (2 mL). After stirring 68 hours at ambient temperature, the reaction mixture was diluted with ethyl acetate, washed with water and saturated aqueous sodium chloride, dried over anhydrous sodium sulfate, filtered, concentrated under reduced pressure, and purified by flash column chromatography (2:1 hexanes/ethyl acetate) to produce 57 mg (62%) of the title compound as a white foam.

MS (APCI): 585 (M+H$^+$). $^1$H NMR (400 MHz, CDCl$_3$, rotameric mixture) δ 7.09 (m, 2H), 7.01 (d, 1H), 6.88 (m, 2H), 6.52 (s, 1H), 6.47 (dd, 1H), 4.39 (br d, 1H), 4.19–4.05 (m, 7H), 3.86 (br t, 1H), 3.68 (m, 2H), 3.21 (m, 1H), 3.05 (m, 1H), 2.82–2.69 (m, 2H), 2.56 (d, 1H), 2.48 (m, 1H), 2.34 (m, 1H), 1.86 (m, 2H), 1.61 (m, 2H), 1.24 (m, 3H), 0.92 (s, 9H).

The title compounds of Examples 20–21 were prepared according to procedures analogous to those described in Example 19.

EXAMPLE 20

Ethyl Ester of N-[trans-7-Chloro-5-(2,3-ethylenedioxyphenyl)-1-neopentyl-1,2,3,5-tetrahydro-4,1-benzoxazepine-3-acetyl]-(R)-nipecotic Acid 32% yield. MS (APCI): 585 (M+H$^+$). $^1$H NMR (400 MHz, CDCl$_3$, rotameric/diastereomeric mixture) δ 7.11 (m, 2H), 7.01 (d, 1H), 6.88 (m, 2H), 6.50 (m, 2H), 2.56 (d, 1H), 1.25 (m, 3H), 0.92 (s, 9H).

EXAMPLE 21

Ethyl Ester of N-[trans-7-Chloro-5-(2,3-dimethoxyphenyl)-1-neopentyl-1,2,3,5-tetrahydro-4,1-benzoxazepine-3-acetyl]isonipecotic Acid 47% yield. $^1$H NMR (400 MHz, CDCl$_3$, rotameric mixture) δ 7.13 (m, 3H), 7.02 (d, 1H), 6.90 (m, 1H), 6.63 (s, 1H), 6.43 (dd, 1H), 4.39 (br d, 1H), 4.25 (m, 1H), 4.12 (m, 2H), 3.86 (s, 3H), 3.64 (m, 3H), 3.49 and 3.48 (s, 3H), 3.21 (br d, 1H), 3.05 (br q, 1H), 2.76 (m, 2H), 2.54 (d, 1H), 2.47 (m, 1H), 2.35 (m, 1H), 1.86 (m, 2H), 1.60 (m, 2H), 1.24 (m, 3H), 0.94 (s, 9H).

EXAMPLE 22

N-[trans-7-Chloro-5-(2,3-ethylenedioxyphenyl)-1-neopentyl-1,2,3,5-tetrahydro-4,1-benzoxazepine-3-acetyl]isonipecotic Acid Potassium carbonate (27 mg, 190 mmol) was added to a solution of the ethyl ester of N-[trans-7-chloro-5-(2,3-ethylenedioxyphenyl)-1-neopentyl-1,2,3,5-tetrahydro-4,1-benzoxazepine-3-acetyl]isonipecotic Acid (56 mg, 96 mmol) in methanol (1.9 mL) and water (0.2 mL). The resulting mixture was heated at reflux for 8 hours. After cooling to room temperature, the reaction mixture was concentrated and the resulting residue taken up in water, acidified with an aqueous solution of 1N hydrochloric acid and extracted with ethyl acetate (3×). The combined organics were dried over anhydrous sodium sulfate, filtered, concentrated under reduced pressure, and purified by flash column chromatography (2% methanol/chloroform) to give 46 mg (87%) of the title compound as a white foam.

MS (APCI): 557 (M+H$^+$). $^1$H NMR (400 MHz, CDCl$_3$) δ 7.06 (m, 3H), 6.86 (m, 2H), 6.50 (m, 2H), 4.39 (d, 1H), 4.17–4.06 (m, 5H), 3.86 (m, 1H), 3.67 (m, 2H), 3.21–3.04 (m, 2H), 2.90–2.68 (m, 2H), 2.56 (m, 2H), 2.35 (m, 1H), 1.89 (m, 2H), 1.63 (m, 2H), 0.92 (s, 9H).

The title compounds of Examples 23–24B were prepared according to procedure analogous to those described in Example 22.

EXAMPLE 23

N-[trans-7-Chloro-5-(2,3-ethylenedioxyphenyl)-1-neopentyl-1,2,3,5-tetrahydro-4,1-benzoxazepine-3-acetyl]-(R)-nipecotic Acid 83% yield. MS (APCI): 557 (M+H$^+$). $^1$H NMR (400 MHz, CDCl$_3$, rotameric/diastereomeric mixture) δ 7.06 (m, 3H), 6.87 (m, 2H), 6.50 (m, 2H), 2.56 (d, 1H), 0.91 (s, 9H).

EXAMPLE 24

N-[trans-7-Chloro-5-(2,3-dimethoxyphenyl)-1-neopentyl-1,2,3,5-tetrahydro-4,1-benzoxazepine-3-acetyl]isonipecotic Acid 64% yield. MS (APCI): 559 (M+H$^+$). $^1$H NMR (400 MHz, CDCl$_3$) δ 7.15–7.00 (m, 4H), 6.90 (m, 1H), 6.62 (s, 1H), 6.43 (dd, 1H), 4.38 (br d, 1H), 4.20 (m, 1H), 3.85 (s, 3H), 3.67 (m, 3H), 3.48 (s, 3H), 3.15 (m, 2H), 2.77 (m, 2H), 2.54 (d, 1H), 2.48 (m, 1H), 2.38 (m, 1H), 1.86 (m, 2H), 1.58 (m, 2H), 0.93 (s, 9H).

EXAMPLE 24A

N-[trans-7-Methyl-5-(2,3-ethylenedioxyphenyl)-1-neopentyl-1,2,3,5-tetrahydro-4,1-benzoxazepine-3-acetyl]isonipecotic Acid 86% yield. MS (APCI): 537 (M+H$^+$). $^1$H NMR (400 MHz, CDCl$_3$) δ 7.05 (dd, 1H), 6.98 (s, 2H), 6.84 (m, 2H), 6.60 (d, 1H), 6.32 (d, 1H), 4.40 (m, 1H), 4.11 (m, 5H), 3.90 (m, 1H), 3.67 (d, 1H), 3.53 (td, 1H), 3.10 (m, 2H), 2.85 (m, 1H), 2.70 (m, 1H), 2.54 (br d, 2H), 2.35 (td, 1H), 2.09 (s, 3H), 1.90 (m, 2H), 1.62 (m, 2H), 0.92 (s, 9H).

EXAMPLE 24B

N-[trans-7-Methyl-9-chloro-5-(2,3-ethylenedioxyphenyl)-1-neopentyl-1,2,3,5-tetrahydro-4,1-benzoxazepine-3-acetyl]isonipecotic Acid 90% yield. MS (APCI): 571 (M+H$^+$). $^1$H NMR (400 MHz, CDCl$_3$) δ 7.06 (s, 1H), 6.99 (d, 1H), 6.84 (m, 3H), 6.20 (d, 1H), 4.40 (m, 1H), 4.18 (m, 2H), 4.07 (s, 2H), 3.91 (m, 2H), 3.77 (dd, 1H), 3.32 (m, 2H), 3.10 (m, 1H), 2.86 (t, 1H), 2.74 (m, 2H), 2.52 (m, 1H), 2.26 (d, 1H), 2.08 (s, 3H), 1.95 (m, 1H), 1.85 (m, 1H), 1.61 (m, 2H), 0.94 (s, 9H).

EXAMPLE 25

Ethyl Ester of N-[trans-7-Chloro-5-(2,3-dimethoxyphenyl)-1-neopentyl-2-oxo-1,2,3,5-tetrahydro-4,1-benzothiazepin-3-acetyl]isonipecotic Acid

EXAMPLE 25A (5-Chloro-2-neopentylamino)phenyl-(2,3-dimethoxyphenyl)methylthiosuccinic Acid A mixture of 9.38 g (26 mmol) (5-chloro-2-neopentylamino)phenyl-(2,3-dimethoxyphenyl)methanol, 7.75 g (52 mmol) mercaptosuccinic acid and 90 ml acetic acid was heated at 55° C. overnight. The reaction was cooled to room temperature, diluted with 900 ml water and the resulting mixture was extracted with 3×400 ml ethyl acetate. The combined ethyl acetate extracts were washed with 4×500 ml water, dried over anhydrous sodium sulfate, filtered and concentrated in vacuo to yield the title compound as a brown oil (4.68 g, 37% yield) which was used in the next step without further purification.

EXAMPLE 25B

Methyl Ester of trans-7-Chloro-5-(2,3-dimethoxyphenyl)-1-neopentyl-2-oxo-1,2,3,5-tetrahydro-4,1-benzothiazepin-3-acetic Acid A mixture of 4.68 g (9.4 mmol) of (5-chloro-2-neopentylamino)phenyl-(2,3-dimethoxyphenyl)methylthiosuccinic acid and 0.18 g (0.94 mmol) p-toluenesulphonic acid in 70 ml chlorobenzene was heated to reflux under nitrogen, removing the water formed with a Soxhlet apparatus containing 3 Å molecular sieves. After heating overnight, the reaction solution was cooled to room temperature and washed with 3×35 ml water, dried over anhydrous sodium sulfate, filtered and concentrated in vacuo. The crude product (5.6 g) was chromatographed on 200 g of silica gel, eluting with 1:1 hexane-ethyl acetate to remove non-polar impurities, followed by 9:1 chloroform-methanol to yield a mixture of the cis- and trans-isomers of the acids of the title compound (2.97 g). The cis/trans acid mixture was converted to the methyl esters by refluxing a methanolic solution (25 ml) containing 5 drops of concentrated sulfuric acid overnight under nitrogen. The reaction solution was cooled to room temperature, basified with 5 ml of saturated aqueous sodium bicarbonate solution and the methanol was removed in vacuo. The residue was taken up in 50 ml ethyl acetate and the resulting solution was washed sequentially with 30 ml saturated sodium bicarbonate solution, 2×30 ml water and 30 ml brine. The ethyl acetate solution was dried over anhydrous sodium sulfate, filtered and concentrated in vacuo to yield a mixture of the methyl esters of the cis- and trans-isomers of the title compound (2.83 g). The cis/trans ester mixture was chromatographed on 400 g silica gel, eluting with 85:15 hexane-ethyl acetate to yield 0.96 g (31% yield) of the methyl ester of the title compound and 1.04 g (34% yield) of the methyl ester of the cis isomer of the title compound.

$^1$H NMR (CDCl$_3$) (trans isomer) δ 0.99 (s, 9H); 2.41 (q, 1H); 3.12 (q, 1H); 3.23 (d, 1H); 3.65 (s, 3H); 3.72 (s, 3H) and 3.73 (m) (total 4H); 3.89 (s, 3H); 4.45 (d, 1H); 6.29 (s, 1H); 6.83 (s, 1H); 6.98 (d, 1H); 7.19 (t, 1H); 7.29 (s, 2H); 7.37 (d, 1H).

EXAMPLE 25C trans-7-Chloro-5-(2,3-dimethoxyphenyl)-1-neopentyl-2-oxo-1,2,3,5-tetrahydro-4,1-benzothiazepin-3-acetic Acid A mixture of 0.96 g (1.94 mmol) of the methyl ester of the title compound and 0.54 g (3.88 mmol) of potassium carbonate in a solution containing 50 ml methanol and 25 ml water was heated at 60° C. overnight. The reaction solution was cooled to room temperature and the methanol was removed in vacuo. The residue was partitioned between 30 ml 1N aqueous hydrochloric solution and 30 ml ethyl acetate. The aqueous phase was extracted with 2×30 ml ethyl acetate and the combined ethyl acetate extracts were washed sequentially with 70 ml water and 70 ml brine, dried over anhydrous sodium sulfate, filtered and concentrated to dryness in vacuo, yielding 0.92 g (99% yield, 11% overall yield) of the title compound as a white solid.

$^1$H NMR (CDCl$_3$) δ 0.99 (s, 9H); 2.53 (q, 1H); 3.09 (q, 1H); 3.23 (d, 1H); 3.69 (q, 1H); 3.73 (s, 3H); 3.89 (s, 3H); 4.46 (d, 1H); 6.29 (s, 1H); 6.83 (s, 1H); 8.98 (d, 1H); 7.2 (t, 1H); 7.28 (s, 2H); 7.33 (q, 1H).

EXAMPLE 25D

Ethyl Ester of N-[trans-7-Chloro-5-(2,3-dimethoxyphenyl)-1-neopentyl-2-oxo-1,2,3,5-tetrahydro-4,1-benzothiazepin-3-acetyl]isonipecotic Acid To a solution of 150 mg (0.31 mmol) N-trans-7-chloro-5-(2,3-dimethoxyphenyl)-1-neopentyl-2-oxo-1,2,3,5-tetrahydro-4,1-benzothiazepin-3-acetic acid and 0.053 ml (0.34 mmol) ethyl isonipecotate in 10 ml dimethylformamide cooled to 0° C. was added 0.052 ml (0.34 mmol) diethyl cyanophosphonate followed by 0.048 ml (0.34 mmol) triethylamine. The reaction solution was stirred at room temperature for 1 h, then poured into 50 ml ice water.

The resulting mixture was extracted with 3×40 ml ethyl acetate and the combined ethyl acetate extracts were washed sequentially with 50 ml 1N aqueous hydrochloric solution, 50 ml saturated sodium bicarbonate, 3×50 ml water and 50 ml brine. The ethyl acetate solution was then dried over anhydrous sodium sulfate, filtered and concentrated in vacuo to a white solid (0.193 g). Trituration of the white solid with 7:3 hexane-ethyl acetate and filtration yielded 0.159 g (82% yield) of the title compound.

$^1$H NMR (CDCl$_3$) δ 0.98 (S, 9H); 1.26 (t, 3H); 1.5–2.0 (c, 4H); 2.3 (q, 1H); 2.5 (c, 1H); 2.8 (c, 1H); 3.0–3.3 (c, 3H); 3.7–3.9 [c, including 3.71 (s, 3H) and 3.89 (s, 3H), total 8H]; 4.12 (q, 2H); 4.28 (c, 1H); 4.45 (q, 1H); 6.29 (s, 1H); 6.81 (d, 1H); 6.97 (d, 1H); 7.2 (t, 1H); 7.24–7.42 (m and c, 3H).

The title compounds of Examples 26–36A were prepared according to procedure analogous to those described in Example 25.

EXAMPLE 26

Ethyl Ester of N-[trans-7-Chloro-5-(2,3-dimethoxyphenyl)-1-neopentyl-2-oxo-1,2,3,5-tetrahydro-4,1-benzothiazepin-3-acetyl]nipecotic Acid 51% yield. $^1$H NMR (CDCl$_3$) δ 0.99 (s, 9H); 1.25 (c, 3H); 1.3–2.15 (c, 5H); 2.25–3.3 [c and d (3.21), total 6H], 3.7–3.95 [c, including 3.72 (s, 3H) and 3.89 (s, 3H), total 8H]; 4.06–4.2 (m, 2H); 4.5 (c, 1H); 6.29 (s, 1H); 6.8 (s, 1H); 6.98 (d, 1H); 7.19 (t, 1H); 7.23–7.42 (m and c, 3H).

EXAMPLE 27

Ethyl Ester of N-[trans-7-Methyl-5-(2,3-dimethoxyphenyl)-1-neopentyl-2-oxo-1,2,3,5-tetrahydro-4,1-benzothiazepin-3-acetyl]isonipecotic Acid 68% yield. $^1$H NMR (CDCl$_3$) δ 0.99 (s, 9H); 1.25 (m, 3H); 1.46–2.0 (c, 4H); 2.17 (s, 3H); 2.29 (d, 1H); 2.5 (c, 1H); 2.8 (c, 1H); 3.0–3.3 (c and m, 3H); 3.7 (s, 3H); 3.78–3.93 [c and s (3.88, 3H), total 5H]; 4.13 (m, 2H); 4.3 (m, 1H); 4.44 (q, 1H); 6.31 (s, 1H); 6.61 (s, 1H); 6.95 (d, 1H); 7.07 (d, 1H); 7.17 (t, 1H); 7.26 (m, 1H); 7.41 (d, 1H).

EXAMPLE 28

Ethyl Ester of N-[trans-7-Chloro-5-(2-methoxyphenyl)-1-neopentyl-2-oxo-1,2,3,5-tetrahydro-4,1-benzothiazepin-3-acetyl]isonipecotic Acid 69% yield. $^1$H NMR (CDCl$_3$) δ 0.98 (s, 9H); 1.24 (m, 3H); 1.45–2.0 (c, 4H); 2.3 (q, 1H); 2.5 (c, 1H); 2.8 (c, 1H); 3.02–3.27 (c, 3H); 3.68 (s, 3H); 3.82 (c, 2H); 4.13 (m, 2H); 4.27 (c; 1H); 4.46 (q, 1H); 6.33 (s, 1H); 6.79 (s, 1H); 6.91 (d 1H); 7.08 (t, 1H); 7.22–7.4 (m, 3H); 7.73 (d, 1H).

EXAMPLE 29

Ethyl Ester of N-[trans-7-Chloro-5-(2,3-ethylenedioxyphenyl)-1-neopentyl-2-oxo-1,2,3,5-tetrahydro-4,1-benzothiazepin-3-acetyl]isonipecotic Acid 82% yield. $^1$H NMR (CDCl$_3$) δ 0.95 (s, 9H); 1.25 (m, 3H); 1.5–2.0 (c, 4H); 2.3 (q, 1H); 2.5 (c, 1H); 2.8 (c, 1H); 3.02–3.27 (c, 3H); 3.82 (c, 2H); 4.04–4.35 (c and m, 7H); 4.45 (q, 1H); 6.23 (s, 1H); 6.85–7.0 (m, 3H); 7.24–7.37 (m, 3H).

EXAMPLE 30

Ethyl Ester of N-[trans-7-Methyl-5-(2,3-ethylenedioxyphenyl)-1-neopentyl-2-oxo-1,2,3,5-tetrahydro-4,1-benzothiazepin-3-acetyl]isonipecotic Acid 76% yield. $^1$H NMR (CDCl$_3$) δ 0.96 (s, 9h); 1.26 (m, 3H); 1.5–2.0 (c, 4H); 2.21 (s, 3H); 2.28 (m, 1H); 2.5 (c, 1H); 2.8 (c, 1H); 3.0–3.3 (c and m, 3H); 3.82 (m, 2H); 4.02–4.38 (c and m, 7H); 4.44 (q, 1H); 6.26 (s, 1H); 6.68 (s, 1H); 6.87–6.7.0 (m, 2H); 7.1 (d, 1H); 7.247.34 (m, 2H).

EXAMPLE 31

Ethyl Ester of N-[trans-7-Methyl-5-(2,3-ethylenedioxyphenyl)-1-neopentyl-2-oxo-1,2,3,5-tetrahydro-4,1-benzothiazepin-3-acetyl]nipecotic Acid 70% yield. $^1$H NMR (CDCl$_3$) δ 0.98 (s, 9H); 1.25 (m, 3H); 1.3–2.13 (c, 5H); 2.2–2.82 [c and s (2.21, 3H), total 6H]; 2.9–3.3 [c and d (3.25), total 3H]; 3.7–3.9 (c, 2H); 4.02–4.22 (c and m, 6H); 4.44 (m, 1H); 6.27 (s, 1H); 6.68 (s, 1H); 6.87–7.0 (m, 2H); 7.09 (d, 1H); 7.25–7.35 (m, 2H).

EXAMPLE 32

Ethyl Ester of N-[trans-7-Chloro-5-(2-methoxyphenyl)-1-neopentyl-2-oxo-1,2,3,5-tetrahydro-4,1-benzothiazepin-3-acetyl]nipecotic Acid 73% yield. $^1$H NMR (CDCl$_3$) δ 0.98 (s, 9H); 1.25 (c, 3H); 1.3–2.15 (c, 5H); 2.25–3.3 [c and d (3.23), total 6H]; 3.65–3.88 [c and s (3.69, 3H), total 5H]; 4.24 (m, 2H); 4.47 (m, 1H); 6.33 (s, 1H); 6.79 (d, 1H); 6.91 (d, 1H); 7.08 (t, 1H); 7.2–7.4 (m, 3H); 7.73 (m, 1H).

EXAMPLE 33

Ethyl Ester of N-[trans-7-Chloro-5-(2,3-ethylenedioxyphenyl)-1-neopentyl-2-oxo-1,2,3,5-tetrahydro-4,1-benzothiazepin-3-acetyl]nipecotic Acid 76% yield. $^1$H NMR (CDCl$_3$) δ 0.95 (s, 9H); 1.26 (m, 3H); 1.3–2.15 (c, 5H); 2.25–3.3 [c and d (3.22), total 6H]; 3.7–3.85 (c, 2H); 4.04–4.25 (m, 6H); 4.45 (m, 1H); 6.23 (s, 1H); 6.86–7.0 (m, 3H); 7.25–7.38 (m, 3H).

EXAMPLE 34

Ethyl Ester of N-[trans-7-Methyl-5-(2,3-dimethoxyphenyl)-1-neopentyl-2-oxo-1,2,3,5-tetrahydro-4,1-benzothiazepin-3-acetyl]nipecotic Acid 73% yield. $^1$H NMR (CDCl$_3$) δ 0.99 (s, 9H); 1.25 (m, 3H); 1.3–2.14 (c, 5H); 2.17 (s, 3H); 2.23–3.3 [c and d (3.26), total 6H]; 3.7–3.95 [c, s (3.7, 3H) and s (3.88, 3H), total 8H]; 4.12 (m, 2H); 4.44 (m, 1H); 6.31 (s, 1H); 6.61 (s, 1H); 6.95 (d, 1H); 7.08 (d, 1H); 7.18 (t, 1H); 7.26 (m, 1H); 7.41 (d, 1H).

EXAMPLE 35

Ethyl Ester of N-[trans-7-Methylthio-5-(2,3-dimethoxyphenyl)-1-neopentyl-2-oxo-1,2,3,5-tetrahydro-4,1-benzothiazepin-3-acetyl]isonipecotic Acid 80% yield. $^1$H NMR (CDCl$_3$) δ 0.99 (s, 3H); 1.25 (m, 3H); 1.4–2.0 (c, 4H); 2.25–2.34 [c and s (2.3, 3H), total 4H];

2.5 (c, 1H); 2.8 (c, 1H); 3.0–3.3 [c and d (3.24), total 3H]; 3.71 (s, 3H); 3.78–3.94 [c and s (3.88, 3H), total 5H]; 4.13 (m, 2H); 4.28 (c, 1H); 4.44 (q, 1H); 6.31 (s, 1H); 6.72 (d, 1H); 6.95 (d, 1H); 7.17 (m, 2H); 7.31 (d, 1H), 7.4 (d, 1H).

EXAMPLE 36

Ethyl Ester of N-[trans-7-Methylthio-5-(2,3-dimethoxyphenyl)-1-neopentyl-2-oxo-1,2,3,5-tetrahydro-4,1-benzothiazepin-3-acetyl]nipecotic Acid 71% yield. $^1$H NMR (CDCl$_3$) δ 0.99 (s, 9H); 1.25 (m, 3H); 1.3–2.14 (c, 5H); 2.2–3.3 [c, s (2.3, 3H) and d (3.23), total 9H]; 3.7–3.94 [c, s (3.71, 3H) and s (3.88, 3H). total 8H]; 4.13 (m, 2H); 4.44 (m, 1H); 6.31 (s, 1H); 6.72 (d, 1H); 6.96 (d, 1H); 7.17 (m, 2H); 7.31 (d, 1H); 7.4 (d, 1H).

EXAMPLE 36A

Ethyl Ester of N-[trans-7-Chloro-5-(3,4-ethylenedioxyphenyl)-1-neopentyl-2-oxo-1,2,3,5-tetrahydro-4,1-benzothiazepin-3-acetyl]isonipecotic Acid 46% yield. $^1$H NMR (CDCl$_3$) δ 0.95 (s, 9H); 1.25 (m, 3H); 4.12 (m, 2H); 4.3 (s, 4H); 4.43 (q, 1H); 5.81 (s, 1H).

EXAMPLE 37

N-[trans-7-Chloro-5-(2,3-dimethoxyphenyl)-1-neopentyl-2-oxo-1,2,3,5-tetrahydro-4,1-benzothiazepin-3-acetyl]isonipecotic Acid A mixture of 159 mg (0.26 mmol) of the ethyl ester of trans-7-Chloro-5-(2,3-dimethoxyphenyl)-1-neopentyl-2-oxo-1,2,3,5-tetrahydro-4,1-benzothiazepin-3-acetyl] isonipecotic acid and 71 mg (0.52 mmol) of potassium carbonate in 20 ml methanol and 10 ml water was heated at 60° C. overnight. The reaction mixture was cooled to room temperature and the methanol removed in vacuo. The residue was partitioned between 40 ml 1N aqueous hydrochloric acid and 40 ml ethyl acetate. The aqueous phase was extracted with 2×40 ml ethyl acetate and the combined ethyl acetate extracts were washed sequentially with 60 ml water and 60 ml brine, dried over anhydrous sodium sulfate, filtered and concentrated in vacuo to yield the title compound as a white solid (0.6 g, 39% yield).

$^1$H NMR (CDCl$_3$) δ 0.98 (s, 9H); 1.5–2.05 (c, 4H); 2.3 (d, 1H); 2.57 (c, 1H); 2.85 (c, 1H); 3.04–3.28 (c, 3H); 3.71 (s, 3H); 3.75–3.9 (total 5H) including 3.89 (s, 3H); 4.28 (c, 1H); 4.45 (q, 1H); 6.29 (s, 1H); 6.8 (d, 1H); 6.97 (d, 1H); 7.2 (t, 1H); 7.23–7.4 (m and c, 3H).

The title compounds of Examples 38–51 were prepared according to procedure analogous to those described in Example 37.

EXAMPLE 38

N-[trans-7-Chloro-5-(2,3-dimethoxyphenyl)-1-neopentyl-2-oxo-1,2,3,5-tetrahydro-4,1-benzothiazepin-3-acetyl]nipecotic Acid 98% yield. $^1$H NMR (CDCl$_3$) δ 0.98 (s, 9H); 1.35–3.3 [c and d (3.23, 1H), total 11H]; 3.7–3.9 [c, s (3.72, 3H) and s (3.89, 3H), total 8H]; 4.44 (d, 1H); 6.29 (s, 1H); 6.8 (s, 1H); 6.97 d, 1H); 7.18 (t, 1H); 7.22–7.41 (c and m, 3H).

EXAMPLE 39

N-[trans-7-Methyl-5-(2,3-dimethylphenyl)-1-neopentyl-2-oxo-1,2,3,5-tetrahydro-4,1-benzothiazepin-3-acetyl]isonipecotic Acid 75% yield. $^1$H NMR (CDCl$_3$) δ 0.99 (s, 9H); 1.47–2.04 (c, 4H); 2.17 (s, 3H); 2.3 (d, 1H); 2.56 (c, 1H); 2.8 (c, 1H); 3.0–3.3 (c and m, 3H); 3.7 (s, 3H); 3.78–4.03 [c and s (3.88, 3H), total 5H]; 4.3 (c, 1H); 4.44 (q, 1H); 6.31 (s, 1H); 6.6 (s, 1H); 6.96 (d, 1H); 7.08 (d, 1H); 7.18 (t, 1H); 7.27 (m, 1H); 7.41 (d, 1H).

EXAMPLE 40

N-[trans-7-Chloro-5-(2-methoxyphenyl)-1-neopentyl-2-oxo-1,2,3,5-tetrahydro-4,1-benzothiazepin-3-acetyl]isonipecotic Acid 96% yield. $^1$H NMR (CDCl$_3$) δ 0.98 (s, 9H); 1.5–2.05 (c, 4H); 2.3 (m, 1H); 2.55 (c, 1H); 2.84 (c, 1H); 3.02–3.28 (c, 3H); 3.69 (s, 3H); 3.82 (c, 2H); 4.28 (c, 1H); 4.46 (q, 1H); 6.33 (s, 1H); 6.8 (d, 1H); 6.91 (d, 1H); 7.08 (t, 1H); 7.22–7.4 (m, 3H); 7.73 (d, 1H).

EXAMPLE 41

N-[trans-7-Chloro-5-(2,3-ethylenedioxyphenyl)-1-neopentyl-2-oxo-1,2,3,5-tetrahydro-4,1-benzothiazepin-3-acetyl]isonipecotic Acid 68% yield. $^1$H NMR (CDCl$_3$) δ 0.93 (s, 9H); 1.48–2.0 (c, 4H); 2.28 (d, 1H); 2.47 (c, 1H); 2.84 (c, 1H); 3.02–3.25 (m, 3H); 3.78 (m, 2H); 4.0–4.3 (m, 5H); 4.43 (q, 1H); 6.21 (s, 1H); 6.82–6.97 (m, 3H); 7.22–7.34 (m, 3H).

EXAMPLE 42

N-[trans-7-Methyl-5-(2,3-ethylenedioxyphenyl)-1-neopentyl-2-oxo-1,2,3,5-tetrahydro-4,1-benzothiazepin-3-acetyl]isonipecotic Acid 87% yield. $^1$H NMR (CDCl$_3$) δ 0.96 (s, 9H); 1.5–2.02 (c, 4H); 2.21 (s, 3H); 2.28 (q, 1H); 2.55 (c, 1H); 2.82 (c, 1H); 3.0–3.3 (c and m, 3H); 3.85 (c, 2H); 4.02–4.36 (c, 5H); 4.44 (q, 1H); 6.26 (s, 1H); 6.68 (s, 1H); 6.87–7.0 (m, 2H); 7.09 (d, 1H); 7.24–7.34 (m, 2H).

EXAMPLE 43

N-[trans-7-Methyl-5-(2,3-ethylenedioxyphenyl)-1-neopentyl-2-oxo-1,2,3,5-tetrahydro-4,1-benzothiazepin-3-acetyl]nipecotic Acid 90% yield. $^1$H NMR (CDCl$_3$) δ 0.95 (s, 9H); 1.35–3.3 [c, s (2.21, 3H) and d (3.26, 1H), total 14H]; 3.7–3.9 (c, 2H); 4.0–4.3 (m, 4H); 4.43 (m, 1H); 6.25 (d, 1H); 6.68 (s, 1H); 6.92 (m, 2H); 7.1 (d, 1H); 7.25–7.35 (m, 2H).

EXAMPLE 44

N-[trans-7-Chloro-5-(2-methoxyphenyl)-1-neopentyl-2-oxo-1,2,3,5-tetrahydro-4,1-benzothiazepin-3-acetyl]nipecotic Acid 96% yield. $^1$H NMR (CDCl$_3$) δ 0.98 (s, 9H); 1.35–3.3 [c and d (3.23, 1H), total 11H]; 3.68–3.9 [c and s (3.68, 3H), total 5H]; 4.46 (m, 1H); 6.32 (s, 1H); 6.8 (d, 1H); 6.91 (d, 1H); 7.08 (t, 1H); 7.24–7.4 (c and m, 3H); 7.73 (d, 1H).

EXAMPLE 45

N-[trans-7-Chloro-5-(2,3-ethylenedioxyphenyl)-1-neopentyl-2-oxo-1,2,3,5-tetrahydro-4,1-benzothiazepin-3-acetyl]nipecotic Acid 90% yield. $^1$H NMR (CDCl$_3$) δ 0.95 (s, 9H); 1.3–2.16 (c, 5H); 2.25–3.28 [c and d (3.23), total 6H]; 3.7–3.9 (c, 2H); 4.0–4.28 (m, 4H); 4.45 (m, 1H); 6.22 (d, 1H); 6.86–7.0 (m, 3H); 7.23–7.38 (m, 3H).

EXAMPLE 46

N-[trans-7-Methyl-5-(2,3-dimethoxyphenyl)-1-neopentyl-2-oxo-1,2,3,5-tetrahydro-4,1-benzothiazepin-3-acetyl]nipecotic Acid 93% yield. $^1$H NMR (CDCl$_3$) δ 0.99 (s, 9H); 1.3–2.14 (c, 5H); 2.17 (s, 3H); 2.23–3.3 [c and d (3.26), total 6H]; 3.7–3.98 [c, s (3.71, 3H) and s (3.88, 3H), total 8H]; 4.43 (m, 1H); 6.31 (d, 1H); 6.6 (s, 1H); 6.95 (d, 1H); 7.08 (d, 1H); 7.18 (t, 1H); 7.26 (m, 1H); 7.4 (d, 1H).

EXAMPLE 47

N-[trans-7-Methylthio-5-(2,3-dimethoxyphenyl)-1-neopentyl-2-oxo-1,2,3,5-tetrahydro-4,1-benzothiazepin-3-acetyl]isonipecotic Acid 90% yield. $^1$H NMR (CDCl$_3$) δ 0.99 (s, 9H); 1.46–2.02 (c, 4H); 2.25–2.34 [c and s (2.3, 3H). total 4H]; 2.54 (c, 1H); 2.84 (c, 1H); 3.02–3.3 [c and d (3.24 ), total 3H]; 3.71 (s, 3H); 3.78–3.94 [c and s (3.88, 3H), total 5H]; 4.3 (c, 1H); 4.44 (q, 1H); 6.31 (s, 1H); 6.72 (d, 1H); 6.95 (d, 1H); 7.17 (m, 2H); 7.31 (d, 1H);, 7.4 (d, 1H).

EXAMPLE 48

N-[trans-7-Methylthio-5-(2,3-dimethoxyphenyl)-1-neopentyl-2-oxo-1,2,3,5-tetrahydro-4,1-benzothiazepin-3-acetyl]nipecotic Acid 93% yield. $^1$H NMR (CDCl$_3$) δ 0.99 (s, 9H); 1.3–2.17 (c, 5H); 2.23–3.5 [c, s (2.3, 3H) and d (3.24), total 9H]; 3.7–3.95 [c, s (3.71, 3H) and s (3.88, 3H), total 8H]; 4.45 (m, 1H); 6.3 (d, 1H); 6.71 (d, 1H); 6.95 (d, 1H); 7.17 (t, 2H); 7.31 (d, 1H); 7.4 (d, 1H).

EXAMPLE 49

N-[trans-7-Methyl-5-(2,4-dimethoxy-3-methylphenyl)-1-neopentyl-2-oxo-1,2,3,5-tetrahydro-4,1-benzthiazepine-3-acetyl]isonipecotic Acid Quantitative yield. MS (APCI): 583 (M+H$^+$). $^1$H NMR (400 MHz, CDCl$_3$) δ 7.62 (d, 1H), 7.25 (m, 1H), 7.07 (d, 1H), 6.76 (d, 1H), 6.62 (s, 1H), 6.20 (s, 1H), 4.41 (m, 1H), 4.28 (m, 1H), 3.88 (s, 3H), 3.81 (m, 2H), 3.58 (s, 3H), 3.26 (d, 1H), 3.18 (m, 2H), 2.85 (m, 1H), 2.54 (m, 1H), 2.28 (m, 1H), 2.17 (s, 3H), 2.14 (s, 3H), 1.92 (m, 2H), 1.65 (m, 2H), 0.99 (s, 9H).

EXAMPLE 50

N-[trans-7-Methyl-5-(2,4-dimethoxy-3-methylphenyl)-1-neopentyl-2-oxo-1,2,3,5-tetrahydro-4,1-benzthiazepine-3-acetyl]nipecotic Acid 90% yield. MS (APCI): 583 (M+H$^+$). $^1$H NMR (400 MHz, CDCl3, diasteromeric mixture) δ 7.61 (m, 1H), 7.07 (d, 1H), 6.76 (d, 1h), 6.62 (s, 1H), 6.20 (m, 1H), 3.88 (s, 3H), 3.58 (s, 3H), 3.26 (d, 1H), 2.17 (s, 3H), 2.14 (s, 3H), 0.99 (s, 9H).

EXAMPLE 51

N-[trans-7-Chloro-5-(3,4-ethylenedioxyphenyl)-1-neopentyl-2-oxo-1,2,3,5-tetrahydro-4,1-benzothiazepin-3-acetyl]isonipecotic Acid 99% yield. $^1$H NMR (CDCl$_3$) δ 0.95 (s, 9H); 4.3 (s, 4H); 4.45 (q, 1H); 5.81 (s, 1H).

It should be understood that the invention is not limited to the particular embodiments shown and described herein, but that various changes and modifications may be made without departing from the spirit and scope of this novel concept as defined by the following claims.

What is claimed is:

1. A compound of Formula I

FORMULA I

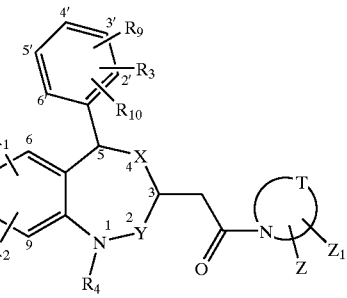

or the pharmaceutically acceptable cationic and anionic salts or stereoisomers thereof wherein X is oxy, thio, —S(O)— or —S(O)$_2$—;

Y is carbonyl or methylene;

R$_1$ and R$_2$ are each independently hydrogen, halo, hydroxyl, trifluoromethyl, (C$_1$–C$_4$)alkyl, fluorinated (C$_1$–C$_4$)alkyl having from 1 to 9 fluorines, (C$_1$–C$_4$)alkoxy, fluorinated (C$_1$–C$_4$)alkoxy having from 1 to 9 fluorines, (C$_1$–C$_4$)alkylthio, (C$_1$–C$_4$)alkylsulfinyl, (C$_1$–C$_4$)alkylsulfonyl, phenyl, amino, mono-N- or di-N,N-(C$_1$–C$_4$)alkylamino, carboxyl, (C$_1$–C$_4$)alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from 1 to 9 fluorines, (C$_1$–C$_6$)alkanoyl, (C$_1$–C$_6$)alkanoyl(C$_1$–C$_6$) alkyl, oxazolyl, thiazolyl, isoxazolyl, pyrazolyl or isothiazolyl wherein said preceding heterocycles are carbon linked or wherein R$_1$ and R$_2$ can be taken together to form a five, six or seven membered carbocyclic ring or can be taken together to form methylenedioxyl, ethylenedioxyl or propylenedioxyl and such rings formed by taking R$_1$ and R$_2$ together are fused at the 7 and 8 positions;

R$_3$, R$_9$ and R$_{10}$ are each independently hydrogen, halo, hydroxyl, trifluoromethyl, (C$_1$–C$_4$)alkyl, fluorinated (C$_1$–C$_4$)alkyl having from 1 to 9 fluorines, (C$_1$–C$_4$) alkoxy, fluorinated (C$_1$–C$_4$)alkoxy having from 1 to 9 fluorines, (C$_1$–C$_4$)alkylthio, (C$_1$–C$_4$)alkylsulfinyl, (C$_1$–C$_4$)alkylsulfonyl, phenyl, amino, mono-N- or di-N,N-(C$_1$–C$_4$)alkylamino, carboxyl, (C$_1$–C$_4$) alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from 1 to 9 fluorines, (C$_1$–C$_6$)alkanoyl, (C$_1$–C$_6$)alkanoyl(C$_1$–C$_6$) alkyl, oxazolyl, thiazolyl, isoxazolyl, pyrazolyl or isothiazolyl wherein said preceding heterocycles are carbon linked or wherein R$_3$ and R$_9$ can be taken together to form methylenedioxyl, ethylenedioxyl or propylenedioxyl and such rings formed by taking R$_3$ and R$_9$ together are fused at the 2' and 3' or 3' and 4' positions;

$R_4$ is $(C_1-C_7)$alkyl, $(C_1-C_7)$alkenyl or $(C_3-C_4)$ cycloalkylmethyl or said $(C_1-C_7)$alkyl, $(C_1-C_7)$alkenyl or $(C_3-C_4)$cycloalkylmethyl is optionally mono-, di-, or tri-substituted wherein the substituents are independently chosen from hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$ alkylthio, $(C_1-C_4)$alkylsulfinyl, $(C_1-C_4)$alkylsulfonyl, mono-N- or di-N,N-$(C_1-C_4)$alkylamino, mono-N- or di-N,N-$(C_1-C_4)$alkylaminocarbonyl, mono-N- or di-N, N-$(C_1-C_4)$alkylaminosulfonyl; or $R_4$ is $(C_1-C_7)$alkyl substituted with 1 to 15 fluorines or $(C_3-C_4)$cycloalkylmethyl substituted with 1 to 9 fluorines; or $R_4$ is het$(C_1-C_6)$alkyl wherein het is a 4–7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;

Z is carboxyl, $(C_1-C_4)$alkoxycarbonyl, mono-N- or di-N, N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$_{12}$)CONR$_{13}$R$_{14}$, N(R$_{12}$)CO$_2$ $(C_1-C_4)$alkyl or N(R$_{12}$)COR$_{15}$;

$Z_1$ is H, carboxyl, hydroxyl, $(C_1-C_4)$alkoxy or $(C_1-C_4)$ alkoxycarbonyl;

$R_{12}$, $R_{13}$ and $R_{14}$ are each independently H or $(C_1-C_4)$ alkyl;

$R_{15}$ is $(C_1-C_4)$alkyl;

$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$ alkylamino, carboxyl, $(C_1-C_4)$alkoxycarbonyl, carbamoyl or mono-N- or di-N,N-$(C_1-C_4)$ alkylcarbamoyl; or $R_5$ is phenyl optionally mono- or di-substituted independently with methyl, methoxyl, fluoro, trifluoromethoxyl, carboxyl, $(C_1-C_4)$ alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R_5$ is thiazolyl, isothiazolyl, thienyl, furyl, pyridinyl or any of said heterocycles optionally mono-substituted by carboxyl, or mono- or di-substituted with methyl; and T forms a four to seven membered mono-aza, saturated ring, said ring optionally containing thio or oxo and said ring optionally mono-substituted on carbon with hydroxyl, $(C_1-C_4)$alkoxy or carboxyl with the proviso that the compound of Formula I is not N-[(3R,5S)-7-chloro-5-(2,3-dimethoxyphenyl)-1-(3-hydroxyl-2,2-dimethylpropyl)-2-oxo-1,2,3,5-tetrahydro-4,1-benzoxazepine-3-acetyl]piperidine-4-carboxylic acid.

2. A compound as recited in claim 1 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$, $R_9$ and $R_{10}$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_3$ and $R_9$ taken together form an $(C_1-C_3)$ alkylenedioxy ring;

X is oxy;

Y is carbonyl;

Z is carboxyl or tetrazol-5-yl; and $Z_1$ is H or carboxyl.

3. A compound as recited in claim 2 wherein $Z_1$ is H;

T forms a piperidin-1-yl ring; and $R_3$ and $R_9$ are each independently $(C_1-C_4)$alkoxy or taken together form a $(C_1-C_3)$alkylenedioxy ring.

4. A compound as recited in claim 3 wherein $R_4$ is neopentyl;

$R_1$ is 7-chloro;

$R_2$ is H;

$R_{10}$ is H;

$R_3$ is 2'-methoxy;

$R_9$ is 3'-methoxy; and

Z is 4-carboxyl.

5. A compound as recited in claim 3 wherein $R_4$ is neopentyl;

$R_1$ is 7-methyl;

$R_2$ is H;

$R_{10}$ is H;

$R_3$ is 2'-methoxy;

$R_9$ is 3'-methoxy; and

Z is 4-carboxyl.

6. A compound as recited in claim 3 wherein $R_4$ is neopentyl;

$R_1$ is 7-methyl;

$R_2$ is H;

$R_{10}$ is H;

$R_3$ is 2'-methoxy;

$R_9$ is 3'-methoxy; and

Z is 3-carboxyl.

7. A compound as recited in claim 3 wherein $R_4$ is neopentyl;

$R_1$ is 7-chloro;

$R_2$ is H;

$R_{10}$ is H;

$R_3$ is 2'-methoxy;

$R_9$ is 3'-methoxy; and

Z is 3-carboxyl.

8. A compound as recited in claim 3 wherein $R_4$ is neopentyl;

$R_1$ is 7-chloro;

$R_2$ is H;

$R_{10}$ is H;

$R_3$ and $R_9$ are taken together to form 2', 3'-ethylenedioxyl; and

Z is 3-carboxyl.

9. A compound as recited in claim 3 wherein $R_4$ is neopentyl;

$R_1$ is 7-chloro;

$R_2$ is H;

$R_{10}$ is H;

$R_3$ and $R_9$ are taken together to form 2', 3'-ethylenedioxyl; and

Z is 4-carboxyl.

10. A compound as recited in claim 2 wherein

T forms a pyrrolidin-1-yl ring;

$R_4$ is neopentyl;

$R_1$ is 7-chloro;

$R_2$ is H;

$R_{10}$ is H;

$R_3$ is 2'-methoxy;

$R_9$ is 3'-methoxy;

Z is 2-carboxyl; and $Z_1$ is H.

11. A compound as recited in claim 2 wherein

T forms a pyrrolidin-1-yl ring;

$R_4$ is neopentyl;

$R_1$ is 7-chloro;

$R_2$ is H;

$R_{10}$ is H;

$R_3$ and $R_9$ are taken together to form 2', 3'-ethylenedioxyl;

Z is 2-carboxyl; and $Z_1$ is H.

12. A compound as recited in claim 2 wherein

T forms a piperidin-1-yl ring;

$R_4$ is neopentyl;

$R_1$ is 7-chloro;

$R_2$ is H;

$R_{10}$ is H;

$R_3$ is 2'-methoxy;

$R_9$ is 3'-methoxy;

Z is 4-carboxyl; and $Z_1$ is 2-carboxyl.

13. A compound as recited in claim 1 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$, $R_9$ and $R_{10}$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_3$ and $R_9$ taken together form an $(C_1-C_3)$ alkylenedioxy ring;

X is oxy;

Y is methylene;

Z is carboxyl or tetrazol-5-yl; and $Z_1$ is H.

14. A compound as recited in claim 13 wherein

T forms a piperidin-1-yl ring; and $R_3$ and $R_9$ are each independently $(C_1-C_4)$alkoxy or taken together form a $(C_1-C_3)$alkylenedioxy ring.

15. A compound as recited in claim 14 wherein $R_4$ is neopentyl;

$R_1$ is 7-chloro;

$R_2$ is H;

$R_{10}$ is H;

$R_3$ and $R_9$ are taken together to form 2', 3'-ethylenedioxyl; and

Z is 3-carboxyl.

16. A compound as recited in claim 14 wherein $R_4$ is neopentyl;

$R_1$ is 7-chloro;

$R_2$ is H;

$R_{10}$ is H;

$R_3$ and $R_9$ are taken together to form 2', 3'-ethylenedioxyl; and

Z is 4-carboxyl.

17. A compound as recited in claim 14 wherein $R_4$ is neopentyl;

$R_1$ is 7-chloro;

$R_2$ is H;

$R_{10}$ is H;

$R_3$ is 2'-methoxy;

$R_9$ is 3'-methoxy; and

Z is 4-carboxyl.

18. A compound as recited in claim 1 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$, $R_9$ and $R_{10}$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_3$ and $R_9$ taken together form an $(C_1-C_3)$ alkylenedioxy ring;

X is thio;

Y is carbonyl;

Z is carboxyl or tetrazol-5-yl; and $Z_1$ is H.

19. A compound as recited in claim 18 wherein

T forms a piperidin-1-yl ring; and $R_3$ and $R_9$ are each independently $(C_1-C_4)$alkoxy or taken together form a $(C_1-C_3)$alkylenedioxy ring.

20. A compound as recited in claim 19 wherein $R_4$ is neopentyl;

$R_1$ is 7-methyl;

$R_2$ is H;

$R_{10}$ is H;

$R_3$ is 2'-methoxy;

$R_9$ is 3'-methoxy; and

Z is 3-carboxyl.

21. A compound as recited in claim 19 wherein $R_4$ is neopentyl;

$R_1$ is 7-methylthio;

$R_2$ is H;

$R_{10}$ is H;

$R_3$ is 2'-methoxy;

$R_9$ is 3'-methoxy; and

Z is 4-carboxyl.

22. A compound as recited in claim 19 wherein $R_4$ is neopentyl;

$R_1$ is 7-methylthio;

R$_2$ is H;
R$_{10}$ is H;
R$_3$ is 2'-methoxy;
R$_9$ is 3'-methoxy; and
Z is 3-carboxyl.
23. A compound as recited in claim 19 wherein
R$_4$ is neopentyl;
R$_1$ is 7-methyl;
R$_2$ is H;
R$_{10}$ is H;
R$_3$ and R$_9$ are taken together to form 2', 3'-ethylenedioxyl; and
Z is 3-carboxyl.
24. A compound as recited in claim 2 wherein
Z$_1$ is H;
T forms a piperidin-1-yl ring; and
R$_3$ and R$_9$ are each independently H, (C$_1$–C$_4$)alkoxy, trifluoromethoxy, or taken together form a (C$_1$–C$_3$) alkylenedioxy ring.
25. A compound as recited in claim 24 wherein
R$_4$ is neopentyl;
R$_1$ is 7-chloro;
R$_2$ is H;
R$_{10}$ is H;
R$_3$ is 2-methoxy;
R$_9$ is 4-methoxy; and
Z is 4-carboxyl.
26. A compound as recited in claim 24 wherein
R$_4$ is neopentyl;
R$_1$ is 7-methyl;
R$_2$ is H;
R$_{10}$ is H;
R$_3$ and R$_9$ are taken together form a 2,3-ethylenedioxy ring; and
Z is 4-carboxyl.
27. A compound as recited in claim 24 wherein
R$_4$ is neopentyl;
R$_1$ is 7-methyl;
R$_2$ is H;
R$_{10}$ is H;
R$_3$ and R$_9$ are taken together form a 2,3-ethylenedioxy ring; and
Z is 3-carboxyl.
28. A compound as recited in claim 24 wherein
R$_4$ is neopentyl;
R$_1$ is 7-chloro;
R$_2$ is H;
R$_{10}$ is H;
R$_3$ is 2-methoxy;
R$_9$ is H; and
Z is 4-carboxyl.
29. A compound as recited in claim 24 wherein
R$_4$ is neopentyl;
R$_1$ is 7-chloro;
R$_2$ is H;
R$_{10}$ is H;
R$_3$ is 2-trifluoromethoxy;
R$_9$ is H; and
Z is 4-carboxyl.
30. A compound as recited in claim 24 wherein
R$_4$ is neopentyl;
R$_1$ is 7-chloro;
R$_2$ is H;
R$_{10}$ is H;
R$_3$ is 2-methoxy; and
R$_9$ is H; and
Z is 3-carboxyl.
31. A compound as recited in claim 24 wherein
R$_4$ is neopentyl;
R$_1$ is 7-chloro;
R$_2$ is H;
R$_{10}$ is H;
R$_3$ and R$_9$ are taken together form a 2,3-methylenedioxy ring; and
Z is 4-carboxyl.
32. A compound as recited in claim 24 wherein
R$_4$ is neopentyl;
R$_1$ is 7-chloro;
R$_2$ is H;
R$_{10}$ is H;
R$_3$ and R$_9$ are taken together form a 2,3-methylenedioxy ring; and
Z is 3-carboxyl.
33. A compound as recited in claim 24 wherein
R$_4$ is neopentyl;
R$_1$ is 7-methyl;
R$_2$ is H;
R$_{10}$ is H;
R$_3$ and R$_9$ are taken together form a 2,3-methylenedioxy ring; and
Z is 4-carboxyl.
34. A compound as recited in claim 24 wherein
R$_4$ is neopentyl;
R$_1$ is 7-methyl;
R$_2$ is H;
R$_{10}$ is H;
R$_3$ and R$_9$ are taken together form a 2,3-methylenedioxy ring; and
Z is 3-carboxyl.
35. A compound as recited in claim 24 wherein
R$_4$ is neopentyl;
R$_1$ is 7-methoxy;
R$_2$ is H;
R$_{10}$ is H;
R$_3$ is 2-methoxy;
R$_9$ is 3-methoxy; and
Z is 3-carboxyl.
36. A compound as recited in claim 24 wherein
R$_4$ is neopentyl;
R$_1$ is 7-trifluoromethoxy;
R$_2$ is H;
R$_{10}$ is H;
R$_3$ is 2-methoxy;
R$_9$ is 3-methoxy; and
Z is 3-carboxyl.
37. A compound as recited in claim 24 wherein R₄ is neopentyl;
R₁ is 7-trifluoromethoxy;
R₂ is H;
R₁₀ is H;
R₃ is 2-methoxy;
R₉ is 3-methoxy; and
Z is 4-carboxyl.

38. A compound as recited in claim 24 wherein
R₄ is neopentyl;
R₁ is 7-trifluoromethoxy:
R₂ is H;
R₁₀ is H;
R₃ and R₉ are taken together form a 2,3-ethylenedioxy ring; and
Z is 4-carboxyl.

39. A compound as recited in claim 24 wherein
R₄ is neopentyl;
R₁ is 7-trifluoromethoxy;
R₂ is H;
R₁₀ is H;
R₃ and R₉ are taken together form a 2,3-ethylenedioxy ring; and
Z is 3-carboxyl.

40. A compound as recited in claim 24 wherein
R₄ is neopentyl;
R₁ is 7-trifluoromethoxy;
R₂ is H;
R₁₀ is H;
R₃ and R₉ are taken together form a 2,3-methylenedioxy ring; and
Z is 4-carboxyl.

41. A compound as recited in claim 24 wherein
R₄ is neopentyl;
R₁ is 7-trifluoromethoxy;
R₂ is H;
R₁₀ is H;
R₃ and R₉ are taken together form a 2,3-methylenedioxy ring; and
Z is 3-carboxyl.

42. A compound as recited in claim 24 selected from
a. (−)-N-[Trans-7-chloro-5-(2,4-dimethoxyphenyl)-1-neopentyl-2-oxo-1,2,3,5-tetrahydro-4,1-benzoxazepin-3-acetyl]isonipecotic acid;
b. (−)-N-[Trans-7-methyl-5-(2,3-ethylenedioxyphenyl)-1-neopentyl-2-oxo-1,2,3,5-tetrahydro-4,1-benzoxazepin-3-acetyl]isonipecotic acid;
c. (−)-N-[Trans-7-methyl-5-(2,3-ethylenedioxyphenyl)-1-neopentyl-2-oxo-1,2,3,5-tetrahydro-4,1-benzoxazepin-3-acetyl]nipecotic acid;
d. (−)-N-[Trans-7-chloro-5-(2-methoxyphenyl)-1-neopentyl-2-oxo-1,2,3,5-tetrahydro-4,1-benzoxazepin-3-acetyl]isonipecotic acid; and
e. (−)-N-[Trans-7-chloro-5-(2-trifluoromethoxyphenyl)-1-neopentyl-2-oxo-1,2,3,5-tetrahydro-4,1-benzoxazepin-3-acetyl]isonipecotic acid.

43. A compound as recited in claim 24 selected from
a. (−)-N-[Trans-7-chloro-5-(2-methoxyphenyl)-1-neopentyl-2-oxo-1,2,3,5-tetrahydro-4,1-benzoxazepin-3-acetyl]nipecotic acid;
b. (−)-N-[Trans-7-chloro-5-(2,3-methylenedioxyphenyl)-1-neopentyl-2-oxo-1,2,3,5-tetrahydro-4,1-benzoxazepin-3-acetyl]isonipecotic acid;
c. (−)-N-[Trans-7-chloro-5-(2,3-methylenedioxyphenyl)-1-neopentyl-2-oxo-1,2,3,5-tetrahydro-4,1-benzoxazepin-3-acetyl]nipecotic acid;
d. (−)-N-[Trans-7-methyl-5-(2,3-methylenedioxyphenyl)-1-neopentyl-2-oxo-1,2,3,5-tetrahydro-4,1-benzoxazepin-3-acetyl]isonipecotic acid; and
e. (−)-N-[Trans-7-methyl-5-(2,3-methylenedioxyphenyl)-1-neopentyl-2-oxo-1,2,3,5-tetrahydro-4,1-benzoxazepin-3-acetyl]nipecotic acid.

44. A compound as recited in claim 24 selected from
a. (−)-N-[trans-7-methoxy-5-(2,3-dimethoxyphenyl))-1-neopentyl-2-oxo-1,2,3,5-tetrahydro-4,1-benzoxazepin-3-acetyl]nipecotic acid;
b. (−)-N-[Trans-7-trifluoromethoxy-5-(2,3-dimethoxyphenyl)-1-neopentyl-2-oxo-1,2,3,5-tetrahydro-4,1-benzoxazepin-3-acetyl]nipecotic acid;
c. (−)-N-[Trans-7-trifluoromethoxy-5-(2,3-dimethoxyphenyl)-1-neopentyl-2-oxo-1,2,3,5-tetrahydro-4,1-benzoxazepin-3-acetyl]isonipecotic acid;
d. (−)-N-[Trans-7-trifluoromethoxy-5-(2,3-ethylenedioxyphenyl)-1-neopentyl-2-oxo-1,2,3,5-tetrahydro-4,1-benzoxazepin-3-acetyl]isonipecotic acid; and
e. (−)-N-[Trans-7-trifluoromethoxy-5-(2,3-ethylenedioxyphenyl)-1-neopentyl-2-oxo-1,2,3,5-tetrahydro-4,1-benzoxazepin-3-acetyl]nipecotic acid.

45. A compound as recited in claim 24 selected from
a. (−)-N-[Trans-7-trifluoromethoxy-5-(2,3-methylenedioxyphenyl)-1-neopentyl-2-oxo-1,2,3,5-tetrahydro-4,1-benzoxazepin-3-acetyl]isonipecotic acid and
b. (−)-N-[Trans-7-trifluoromethoxy-5-(2,3-methylenedioxyphenyl)-1-neopentyl-2-oxo-1,2,3,5-tetrahydro-4,1-benzoxazepin-3-acetyl]nipecotic acid.

46. A compound as recited in claim 1 selected from
a. (−)-N-[Trans-7-chloro-5-(2,3-ethylenedioxyphenyl)-1-neopentyl-2-oxo-1,2,3,5-tetrahydro-4,1-benzoxazepin-3-acetyl]isonipecotic acid;
b. (−)-N-[Trans-7-chloro-5-(2,3-dimethoxyphenyl)-1-neopentyl-2-oxo-1,2,3,5-tetrahydro-4,1-benzoxazepin-3-acetyl]-L-proline;
c. (−)-N-[Trans-7-chloro-5-(2,3-ethylenedioxyphenyl)-2-oxo-1,2,3,5-tetrahydro-4,1-benzoxazepin-3-acetyl]-L-proline;
d. (−)-N-[Trans-7-chloro-5-(2,3-dimethoxyphenyl)-1-neopentyl-2-oxo-1,2,3,5-tetrahydro-4,1-benzoxazepin-3-acetyl]-cis-2,4-piperidinedicarboxylic acid; and
e. (−)-N-[Trans-7-methyl-5-(2,3-dimethoxyphenyl)-1-neopentyl-2-oxo-1,2,3,5-tetrahydro-4,1-benzothiazepin-3-acetyl]nipecotic acid.

47. A compound as recited in claim 1 selected from
a. (−)-N-[Trans-7-methylthio-5-(2,3-dimethoxyphenyl)-1-neopentyl-2-oxo-1,2,3,5-tetrahydro-4,1-benzothiazepin-3-acetyl]isonipecotic acid;
b. (−)-N-[Trans-7-methylthio-5-(2,3-dimethoxyphenyl)-1-neopentyl-2-oxo-1,2,3,5-tetrahydro-4,1-benzothiazepin-3-acetyl]nipecotic acid; and
c. (−)-N-[Trans-7-methyl-5-(2,3-ethylenedioxyphenyl)-1-neopentyl-2-oxo-1,2,3,5-tetrahydro-4,1-benzothiazepin-3-acetyl]nipecotic acid.

48. A compound as recited in claim 1 wherein the compound is
(−)-N-[trans-7-chloro-5-(2,3-ethylenedioxyphenyl)-1-neopentyl-1,2,3,5-tetrahydro-2-oxo-4,1-benzoxazepine-3-acetyl]isonipecotic acid, (−)-N-[Trans-7-chloro-5-(2,3-dimethoxyphenyl)-1-neopentyl-2-oxo-1,2,3,5-tetrahydro-4,1-benzoxazepin-3-acetyl]isonipecotic acid, (−)-N-[Trans-7-chloro-5-(2,3-dimethoxyphenyl)-1-neopentyl-2-oxo-1,2,3,5-tetrahydro-4,1-benzoxazepin-3-acetyl]nipecotic acid, (−)-N-[Trans-7-chloro-5-(2,3-dimethoxyphenyl)-1-neopentyl-2-oxo-1,2,3,5-tetrahydro-4,1-benzoxazepin-3-acetyl]-L-proline, (−)-N-[Trans-7-methyl-5-(2,3-dimethoxyphenyl)-1-neopentyl-2-oxo-1,2,3,5-tetrahydro-4,1-benzoxazepin-3-acetyl]isonipecotic acid, (−)-N-[Trans-7-methyl-5-(2,3-dimethoxyphenyl)-1-neopentyl-2-oxo-1,2,3,5-tetrahydro-4,1-benzoxazepin-3-acetyl]nipecotic acid, or (−)-N-[trans-7-chloro-5-(2,3-ethylenedioxyphenyl)-1-neopentyl-2-oxo-1,2,3,5-tetrahydro-4,1-benzoxazepin-3-acetyl]nipecotic acid.

49. A compound as recited in claim 1 selected from
a. (−)-N-[Trans-7-chloro-5-(2,3-dimethoxyphenyl)-1-neopentyl-2-oxo-1,2,3,5-tetrahydro-4,1-benzoxazepin-3-acetyl]isonipecotic acid;
b. (−)-N-[Trans-7-methyl-5-(2,3-dimethoxyphenyl)-1-neopentyl-2-oxo-1,2,3,5-tetrahydro-4,1-benzoxazepin-3-acetyl]isonipecotic acid;
c. (−)-N-[Trans-7-chloro-5-(2,3-dimethoxyphenyl)-1-neopentyl-2-oxo-1,2,3,5-tetrahydro-4,1-benzoxazepin-3-acetyl]nipecotic acid; and
d. (−)-N-[Trans-7-chloro-5-(2,3-ethylenedioxyphenyl)-1-neopentyl-2-oxo-1,2,3,5-tetrahydro-4,1-benzoxazepin-3-acetyl]nipecotic acid.

50. A compound of Formula I

FORMULA I

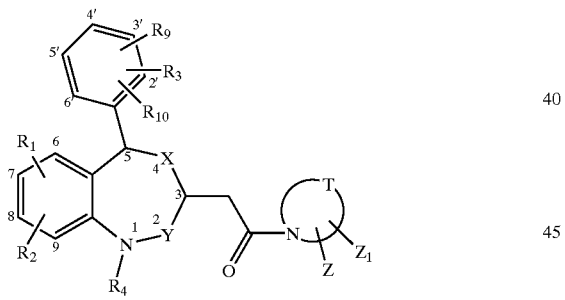

or the pharmaceutically acceptable cationic and anionic salts or stereoisomers thereof wherein X is oxy, thio, —S(O)— or —S(O)$_2$—;

Y is carbonyl or methylene;

$R_1$ or $R_2$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$alkyl, oxazolyl, thiazolyl, isoxazolyl, pyrazolyl or isothiazolyl wherein said preceding heterocycles are carbon linked or wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_3$, $R_9$ and $R_{10}$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$alkyl, oxazolyl, thiazolyl, isoxazolyl, pyrazolyl or isothiazolyl wherein said preceding heterocycles are carbon linked or wherein $R_3$ and $R_9$ can be taken together to form methylenedioxyl, ethylenedioxyl or propylenedioxyl and such rings formed by taking $R_3$ and $R_9$ together are fused at the 2' and 3' or 3' and 4' positions;

$R_4$ is $(C_1-C_7)$alkyl, $(C_1-C_7)$alkenyl or $(C_3-C_4)$cycloalkylmethyl or said $(C_1-C_7)$alkyl, $(C_1-C_7)$alkenyl or $(C_3-C_4)$cycloalkylmethyl is optionally mono-, di-, or tri-substituted wherein the substituents are independently chosen from hydroxyl, oxo, $(C_1-C_4)$alkyl, amino, carboxy, thiol, $(C_1-C_4)$alkoxy, $(C_1-C_4)$alkoxycarbonyl, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, mono-N- or di-N,N-$(C_1-C_4)$alkylamino, mono-N- or di-N,N-$(C_1-C_4)$alkylaminocarbonyl, mono-N-or di-N,N-$(C_1-C_4)$alkylaminosulfonyl; or $R_4$ is $(C_1-C_7)$alkyl substituted with 1 to 15 fluorines or $(C_3-C_4)$cycloalkylmethyl substituted with 1 to 9 fluorines; or $R_4$ is het$(C_1-C_6)$alkyl wherein het is a 4–7 member saturated or unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;

Z is carboxyl, $(C_1-C_4)$alkoxycarbonyl, mono-N- or di-N,N-$(C_1-C_4)$alkylaminocarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, $N(R_{12})CONR_{13}R_{14}$, $N(R_{12})CO_2(C_1-C_4)$alkyl or $N(R_{12})COR_{15}$;

$Z_1$ is H, carboxyl, hydroxyl, $(C_1-C_4)$alkoxy or $(C_1-C_4)$alkoxycarbonyl;

$R_{12}$, $R_{13}$ and $R_{14}$ are each independently H or $(C_1-C_4)$alkyl;

$R_{15}$ is $(C_1-C_4)$alkyl;

$R_5$ is amino or mono-N- or di-N,N-$(C_1-C_4)$alkylamino; or $R_5$ is $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; or $R_5$ is phenyl optionally mono- or di-substituted independently with methyl, methoxyl, fluoro, trifluoromethoxyl, carboxyl, ($C_1$–$C_4$) alkoxycarbonyl, methylthio, methylsulfinyl, methylsulfonyl, ($C_1$–$C_4$)alkylsulfonylamino or mono-N- or di-N,N-($C_1$–$C_4$)alkylaminosulfonyl; or $R_5$ is thiazolyl, isothiazolyl, thienyl, furyl, pyridinyl or any of said heterocycles optionally mono-substituted by carboxyl, or mono- or di-substituted with methyl; and T forms a four to seven membered mono-aza, saturated ring, said ring optionally containing thio or oxo and said ring optionally mono-substituted on carbon with hydroxyl, ($C_1$–$C_4$)alkoxy or carboxyl with the proviso that the compound of Formula I is not N-[(3R,5S)-7-chloro-5-(2,3-dimethoxyphenyl)-1-(3-hydroxy-2,2-dimethylpropyl)-2-oxo-1,2,3,5-tetrahydro-4,1-benzoxazepine-3-acetyl]piperidine-4-carboxylic acid.

51. A pharmaceutical composition which comprises a compound of claim 1 or the pharmaceutically acceptable cationic and anionic salts or stereoisomers thereof and a pharmaceutically acceptable carrier.

52. A method of treating hypercholesterolemia which comprises administering to a mammal in need of such treatment a hypercholesterolemic treating amount of a compound of claim 1 or the pharmaceutically acceptable cationic and anionic salts or stereoisomers thereof.

53. A method of treating hypertriglyceridemia which comprises administering to a mammal in need of such treatment a hypertriglyceridemic treating amount of a compound of claim 1 or the pharmaceutically acceptable cationic and anionic salts or stereoisomers thereof.

54. A method of treating atherosclerosis which comprises administering to a mammal in need of such treatment an atherosclerosis treating amount of a compound of claim 1 or the pharmaceutically acceptable cationic and anionic salts or stereoisomers thereof.

55. A method for the treatment of a fungal infection in a mammal in need of such treatment which comprises administering to the mammal an antifungal treating effective amount of a compound of claim 1 or the pharmaceutically acceptable cationic and anionic salts or stereoisomers thereof.

56. A method for the treatment of Alzheimer's disease in a mammal in need of such treatment which comprises administering to the mammal an Alzheimer's disease treating amount of a compound of claim 1 or the pharmaceutically acceptable cationic and anionic salts or stereoisomers thereof.

57. A method for the treatment of acne in a mammal in need of such treatment which comprises administering to the mammal an acne treating amount of a compound of claim 1 or the pharmaceutically acceptable cationic and anionic salts or stereoisomers thereof.

* * * * *